(12) United States Patent
Kim

(10) Patent No.: US 9,289,475 B2
(45) Date of Patent: Mar. 22, 2016

(54) TREATMENT OF CHRONIC INFLAMMATORY RESPIRATORY DISORDERS

(75) Inventor: Jean Kim, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 13/127,876

(22) PCT Filed: Nov. 6, 2009

(86) PCT No.: PCT/US2009/063584
§ 371 (c)(1),
(2), (4) Date: May 5, 2011

(87) PCT Pub. No.: WO2010/054221
PCT Pub. Date: May 14, 2010

(65) Prior Publication Data
US 2011/0305689 A1 Dec. 15, 2011

Related U.S. Application Data

(60) Provisional application No. 61/111,767, filed on Nov. 6, 2008, provisional application No. 61/143,488, filed on Jan. 9, 2009, provisional application No. 61/242,158, filed on Sep. 14, 2009.

(51) Int. Cl.
| | | |
|---|---|---|
| *A61K 39/00* | (2006.01) | |
| *C07K 16/28* | (2006.01) | |
| *C07K 16/22* | (2006.01) | |
| *A61K 31/7072* | (2006.01) | |
| *A61K 31/713* | (2006.01) | |

(52) U.S. Cl.
CPC .............. *A61K 39/00* (2013.01); *A61K 31/7072* (2013.01); *A61K 31/713* (2013.01)

(58) Field of Classification Search
CPC .............. C07K 16/2863; C07K 16/22; C07K 2316/96; C07K 2317/54; C07K 2317/55; C07K 14/71; C07K 16/28; C07K 2317/76; A61K 39/00; A61K 2039/505; A61K 2039/543; A61K 2039/544; A61K 39/395; A61K 2039/507; A61K 9/0043; A61K 9/0075
See application file for complete search history.

(56) References Cited

U.S. PATENT DOCUMENTS

| | | | |
|---|---|---|---|
| 6,350,747 B1 * | 2/2002 | Glennon et al. ............ | 514/232.5 |
| 2004/0014667 A1 * | 1/2004 | Daly et al. ................ | 514/12 |
| 2005/0222066 A1 * | 10/2005 | Richards et al. ............ | 514/44 |
| 2006/0134111 A1 | 6/2006 | Agarwal | |
| 2009/0155266 A1 * | 6/2009 | Elias ....................... | 424/134.1 |

FOREIGN PATENT DOCUMENTS

| | | | |
|---|---|---|---|
| WO | WO 99/29729 | * | 6/1999 |
| WO | WO-2007/056470 A2 | | 5/2007 |

OTHER PUBLICATIONS

Yu et al., Investigative Ophthalmology & Visual Science 49(2): 522-527, Feb. 2008.*
Witte et al., Cancer and Metastasis Reviews 17: 155-161, 1998.*
Stancovski et al., Proceedings of the National Academy of Science USA 88: 8691-8695, 1991.*
Tol et al, N Engl J Med. 5;360(6):563-72, Feb. 2009.*
Boguslawski et al., J Biol Chem 279: 5716-5724, Feb. 13, 2004.*
Barr et al., British J of Cancer 92: 328-333, 2005.*
Elenbaas et al., Genes Dev 15: 50-65, 2001.*
Hu et al., International J of Pediatric Otorhinolaryngology 71: 23-28, 2007.*
Matsune et al., The Laryngoscope 115: 1953-1956, Nov. 2005.*
Skolnick et al., Trends in Biotechnology, 18: 34-39, 2000.*
Jones et al., Pharmacogenomics Journal, 1:126-134, 2001.*
Tosatto et al., Current Pharmaceutical Design, 12:2067-2086, 2006.*
Coste et al., Eur. Respir J 15: 367-372, 2000.*
Psarras et al., J Allergy Clin Immunol 117: 291-297, 2006.*
Brown et al., Am J Physiol Lung Cell Mol. Physiol 281: L1001-L1010, 2001.*
Karen, R.S. et al. "VEGF induces airway epithelial cell proliferation in human fetal lunch in vitro." Am. J. Physiol. Lung Cell Mol. Physiol., 2001, vol. 281, pp. 1001-1010.
Lee, Y.C. et al., "Contribution of Vascular Endothelial Growth Factor to Airway Hyperresponsiveness and Inflammation in a Murine Model of Toluene Diisocyanate-Induced Asthma." J. Immunol., 2002, vol. 168, pp. 3595-3600.
Chetta, A. et al., "Vascular endothelial growth factor up-regulation and bronchial wall remodelling in asthma." Exp. Allergy, 2005, vol. 35, pp. 1437-1442.
Gosepath et al., "Expression, Localization, and Significance of Vascular Permeability/Vascular Endothelial Growth Factor in Nasal Polyps," American Journal of Rhinology 2005, vol. 19 No. 1, pp. 7-13.
Lee et al., "Vascular endothelial growth factor (VEGF) induces remodeling and enhances TH2-mediated sensitization and inflammation in the lung," Nature Medicine 2004, vol. 10. No. 10, pp. 1095-1103.
Lee et al., "Vascular Endothelial Growth Factor Drives Autocrine Epithelial Cell Proliferation and Survival in Chronic Rhinosinusitis with Nasal Polyposis," American Journal of Respiratory and Critical Care Medicine 2009, vol. 180, pp. 1056-1067.

(Continued)

*Primary Examiner* — Phuong Huynh
(74) *Attorney, Agent, or Firm* — Venable LLP; Keith G. Haddaway; Miguel A. Lopez

(57) ABSTRACT

This invention relates, e.g., to a method for treating a subject having a chronic inflammatory respiratory disorder, comprising administering to the subject an effective amount of an inhibitor of the expression of and/or the activity of VEGF-A and/or VEGFR1 and/or VEGFR2 and/or NP1, or a combination thereof. Also described are screening assays for agents for treating a subject having a chronic inflammatory respiratory disorder, and kits for performing one of the methods of the invention.

7 Claims, 8 Drawing Sheets

(56) References Cited

OTHER PUBLICATIONS

Otto et al., "The role of cytokines in chronic rhinosinusitis with nasal polyps," Current Opinion in Otolaryngology & Head and Neck Surgery 2008, vol. 16, 270-274.

Ramanathan et al., "Th2 cytokines associated with chronic rhinosinusitis with polyps down-regulate the antimicrobial immune function of human sinonasal epithelial cells," Am. J. Rhinol. 2008, vol. 22 No. 2, pp. 115-121.

Von Wronski, et al., "Enhanced Inhibition of VEGF Binding and Activity by Mixtures of Neuropilin-1-binding and VEGFR-2-binding Peptides," American Association for Cancer Research, Proceedings of the Annual Meeting, US, vol. 46, Apr. 1, 2005, p. 915.

Jia et al., "Characteristics of a Bicyclic Peptide Neuropilin-1 (NP-1) Antagonist (EG3287) Reveals Importance of Vascular Endothelial Growth Factor Exon 8 for NP-1 Binding and Role of NP-1 in KDP Signaling," Journal of Biological Chemistry, American Society of Biochemistry and Molecular Biology, US, vol. 281, No. 19, May 12, 2006.

Tachibana et al., "Generation and Characterization of a Monoclonal Antibody Against NPI-1 Subfamily of Importin [alpha]," Hydrodoma, vol. 27, No. 4, Aug. 1, 2008.

Li et al., "Pancreatic Carcinoma Cells Express Neurophilins and Vascular Endothelial Growth Factor, but not Vascular Endothelial Growth Factor Receptors," American Cancer Society, Philadelphia, PA, US, vol. 101, No. 10, Nov. 15, 2004.

Extended European Search Report issued in European Patent Application No. 13187584.1 on Apr. 8, 2014.

* cited by examiner

SEQUENCE LISTING

<160> NUMBER OF SEQ ID NOS: 35

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ccacauuuca caagaagauu gugca                                         25

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2

-continued ugcacaaucu ucuugugaaa ugugg                                       25

<210> SEQ ID NO 3
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gccaggauac gaaggugaag gagaa                                       25

<210> SEQ ID NO 4
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uucuccuuca ccuucguauc cuggc                                       25

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ucugucgcua cgaccggcua gaaau                                       25

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
auuucuagcc ggucguagcg acaga                                       25

<210> SEQ ID NO 7
<211> LENGTH: 3665
<212> TYPE: DNA
<213> ORGANISM: Homo sapiens

<400> SEQUENCE: 7
ggcttggggc agccgggtag ctcggaggtc gtggcgctgg gggctagcac cagcgctctg    60
tcgggaggcg cagcggttag gtggaccggt cagcggactc accggccagg gcgctcggtg   120
ctggaatttg atattcattg atccgggttt tatccctctt ctttttttctt aaacattttt   180 ttttaaaact gtattgtttc tcgttttaat ttattttttgc ttgccattcc ccacttgaat   240
cgggccgacg gcttgggag attgctctac ttccccaaat cactgtggat tttgaaaacc    300
agcagaaaga ggaaagaggt agcaagagct ccagagagaa gtcgaggaag agagagacgg   360
ggtcagagag agcgcgcggg cgtgcgagca gcgaaagcga caggggcaaa gtgagtgacc   420
tgcttttggg ggtgacgcc ggagcgcggc gtgagccctc cccttggga tcccgcagct     480 gaccagtcgc gctgacggac agacagacag acaccgcccc cagccccagc taccacctcc   540

```
tccccggccg gcggcggaca gtggacgcgg cggcgagccg cgggcagggg ccggagcccg    600
cgcccggagg cggggtggag ggggtcgggg ctcgcggcgt cgcactgaaa cttttcgtcc    660
aacttctggg ctgttctcgc ttcggaggag ccgtggtccg cgcggggaa gccgagccga    720 gcggagccgc gagaagtgct agctcggcc gggaggagcc gcagccgag gagggggagg    780 aggaagaaga gaaggaagag gagaggggc cgcagtggcg actcggcgct cggaagccgg    840
gctcatggac gggtgaggcg gcggtgtgcg cagacagtgc tccagccgcg cgcgctcccc    900
aggccctggc ccgggcctcg ggccggggag gaagagtagc tcgccgaggc gccgaggaga    960
gcgggccgcc ccacagcccg agccggagag ggagcgcgag ccgcgccggc cccggtcggg   1020
cctccgaaac catgaacttt ctgctgtctt gggtgcattg gagccttgcc ttgctgctct   1080
acctccacca tgccaagtgg tcccaggctg cacccatggc agaaggagga gggcagaatc   1140
atcacgaagt ggtgaagttc atggatgtct atcagcgcag ctactgccat ccaatcgaga   1200
ccctggtgga catcttccag gagtaccctg atgagatcga gtacatcttc aagccatcct   1260
gtgtgcccct gatgcgatgc ggggctgct gcaatgacga gggcctggag tgtgtgccca   1320
ctgaggagtc caacatcacc atgcagatta tgcggatcaa acctcaccaa ggccagcaca   1380
taggagagat gagcttccta cagcacaaca aatgtgaatg cagaccaaag aaagatagag   1440
caagacaaga aaaaaaatca gttcgaggaa agggaaaggg gcaaaaacga aagcgcaaga   1500
aatcccggta taagtcctgg agcgtgtacg ttggtgcccg ctgctgtcta atgccctgga   1560
gcctccctgg cccccatccc tgtgggcctt gctcagagcg gagaaagcat ttgtttgtac   1620
aagatccgca gacgtgtaaa tgttcctgca aaaacacaga ctcgcgttgc aaggcgaggc   1680
agcttgagtt aaacgaacgt acttgcagat gtgacaagcc gaggcggtga gccgggcagg   1740
aggaaggagc ctccctcagg gtttcgggaa ccagatctct caccaggaaa gactgataca   1800
gaacgatcga tacagaaacc acgctgccgc caccacacca tcaccatcga cagaacagtc   1860
cttaatccag aaacctgaaa tgaaggaaga ggagactctg cgcagagcac tttgggtccg   1920
gagggcgaga ctccggcgga agcattcccg ggcgggtgac ccagcacggt ccctcttgga   1980
attggattcg ccattttatt tttcttgctg ctaaatcacc gagcccggaa gattagagag   2040
ttttatttct gggattcctg tagacacacc cacccacata catacattta tatatatata   2100
tattatatat atataaaaat aaatatctct attttatata tataaaatat atatattctt   2160
tttttaaatt aacagtgcta atgttattgg tgtcttcact ggatgtattt gactgctgtg   2220
gacttgagtt gggagggaa tgttcccact cagatcctga cagggaagag gaggagatga   2280
gagactctgg catgatcttt ttttgtccc acttggtggg gccagggtcc tctcccctgc   2340
ccaggaatgt gcaaggccag gcatggggg caaatatgac ccagttttgg gaacaccgac   2400
aaacccagcc ctggcgctga gcctctctac cccaggtcag acggacagaa agacagatca   2460
caggtacagg gatgaggaca ccggctctga ccaggagttt ggggagcttc aggacattgc   2520
tgtgctttgg ggattccctc cacatgctgc acgcgcatct cgcccccagg ggcactgcct   2580
ggaagattca ggagcctggg cggccttcgc ttactctcac ctgcttctga gttgcccagg   2640
agaccactgg cagatgtccc ggcgaagaga agagacacat tgttggaaga agcagcccat   2700
gacagctccc cttcctggga ctcgccctca tcctcttcct gctcccctc ctggggtgca   2760 gcctaaaagg acctatgtcc tcacaccatt gaaaccacta gttctgtccc ccaggagac   2820 ctggttgtgt gtgtgtgagt ggttgacctt cctccatccc ctggtccttc ccttcccttc   2880
```

| | |
|---|---|
| ccgaggcaca gagagacagg gcaggatcca cgtgcccatt gtggaggcag agaaaagaga | 2940 |
| aagtgtttta tatacggtac ttatttaata tcccttttta attagaaatt aaaacagtta | 3000 |
| atttaattaa agagtagggt ttttttttcag tattcttggt taatatttaa tttcaactat | 3060 |
| ttatgagatg tatcttttgc tctctcttgc tctcttattt gtaccggttt ttgtatataa | 3120 |
| aattcatgtt tccaatctct ctctccctga tcggtgacag tcactagctt atcttgaaca | 3180 |
| gatatttaat tttgctaaca ctcagctctg ccctccccga tccctggct ccccagcaca | 3240 |
| cattcctttg aaataaggtt tcaatataca tctacatact atatatatat ttggcaactt | 3300 |
| gtatttgtgt gtatatatat atatatatgt ttatgtatat atgtgattct gataaaatag | 3360 |
| acattgctat tctgtttttt atatgtaaaa acaaaacaag aaaaaataga gaattctaca | 3420 |
| tactaaatct ctctccttt ttaattttaa tattgttat catttattta ttggtgctac | 3480 |
| tgtttatccg taataattgt ggggaaaaga tattaacatc acgtctttgt ctctagtgca | 3540 |
| gttttttcgag atattccgta gtacatattt ttttttaaac aacgacaaag aaatacagat | 3600 |
| atatcttaaa aaaaaaaaag cattttgtat taaagaattt aattctgatc tcaaaaaaaa | 3660 |
| aaaaa | 3665 |

<210> SEQ ID NO 8
<211> LENGTH: 3542
<212> TYPE: DNA
<213> ORGANISM: Homo sapiens

<400> SEQUENCE: 8

| | |
|---|---|
| ggcttggggc agccgggtag ctcggaggtc gtggcgctgg gggctagcac cagcgctctg | 60 |
| tcggaggcg cagcggttag gtggaccggt cagcggactc accggccagg gcgctcggtg | 120 |
| ctggaatttg atattcattg atccgggttt tatccctctt ctttttttctt aaacattttt | 180 |
| ttttaaaact gtattgtttc tcgttttaat ttatttttgc ttgccattcc ccacttgaat | 240 |
| cgggccgacg gcttggggag attgctctac ttccccaaat cactgtggat tttggaaacc | 300 |
| agcagaaaga ggaaagaggt agcaagagct ccagagagaa gtcgaggaag agagagacgg | 360 |
| ggtcagagag agcgcgcggg cgtgcgagca gcgaaagcga caggggcaaa gtgagtgacc | 420 |
| tgcttttggg ggtgaccgcc ggagcgcggc gtgagccctc cccccttggga tcccgcagct | 480 |
| gaccagtcgc gctgacggac agacagacag acaccgcccc cagccccagc taccacctcc | 540 |
| tccccggccg gcggcggaca gtggacgcgg cggcgagccg cgggcagggg ccggagcccg | 600 |
| cgcccggagg cggggtggag ggggtcgggg ctcgcggcgt cgcactgaaa cttttcgtcc | 660 |
| aacttctggg ctgttctcgc ttcggaggag ccgtggtccg cgcggggaa gccgagccga | 720 |
| gcggagccgc gagaagtgct agctcgggcc gggaggagcc gcagccggag gaggggggagg | 780 |
| aggaagaaga gaaggaagag gagaggggc cgcagtggcg actcggcgct cggaagccgg | 840 |
| gctcatggac gggtgaggcg gcggtgtgcg cagacagtgc tccagccgcg cgcgctcccc | 900 |
| aggccctggc ccgggcctcg ggccggggag gaagagtagc tcgccgaggc gccgaggaga | 960 |
| gcgggccgcc ccacagcccg agccggagag ggagcgcgag ccgcgccggc cccggtcggg | 1020 |
| cctccgaaac catgaacttt ctgctgtctt ggtgcattg gagccttgcc ttgctgctct | 1080 |
| acctccacca tgccaagtgg tcccaggctg cacccatggc agaaggagga gggcagaatc | 1140 |
| atcacgaagt ggtgaagttc atggatgtct atcagcgcag ctactgccat ccaatcgaga | 1200 |
| ccctggtgga catcttccag gagtaccctg atgagatcga gtacatcttc aagccatcct | 1260 |
| gtgtgcccct gatgcgatgc gggggctgct gcaatgacga gggcctggag tgtgtgccca | 1320 |

```
ctgaggagtc caacatcacc atgcagatta tgcggatcaa acctcaccaa ggccagcaca    1380
taggagagat gagcttccta cagcacaaca aatgtgaatg cagaccaaag aaagatagag    1440
caagacaaga aaatccctgt gggccttgct cagagcggag aaagcatttg tttgtacaag    1500
atccgcagac gtgtaaatgt tcctgcaaaa acacagactc gcgttgcaag gcgaggcagc    1560
ttgagttaaa cgaacgtact tgcagatgtg acaagccgag gcggtgagcc gggcaggagg    1620
aaggagcctc cctcagggtt tcgggaacca gatctctcac caggaaagac tgatacagaa    1680
cgatcgatac agaaaccacg ctgccgccac cacaccatca ccatcgacag aacagtcctt    1740
aatccagaaa cctgaaatga aggaagagga gactctgcgc agagcacttt gggtccggag    1800
ggcgagactc cggcggaagc attcccgggc gggtgaccca gcacggtccc tcttggaatt    1860
ggattcgcca ttttattttt cttgctgcta aatcaccgag cccggaagat tagagagttt    1920
tatttctggg attcctgtag acacacccac ccacatacat acatttatat atatatatat    1980
tatatatata taaaaataaa tatctctatt ttatatatat aaaatatata tattcttttt    2040
ttaaattaac agtgctaatg ttattggtgt cttcactgga tgtatttgac tgctgtggac    2100
ttgagttggg aggggaatgt tcccactcag atcctgacag ggaagaggag gagatgagag    2160
actctggcat gatctttttt ttgtcccact tggtggggcc agggtcctct cccctgccca    2220
ggaatgtgca aggccagggc atggggcaa atatgaccca gttttgggaa caccgacaaa    2280
cccagccctg gcgctgagcc tctctacccc aggtcagacg gacagaaaga cagatcacag    2340
gtacagggat gaggacaccg gctctgacca ggagtttggg gagcttcagg acattgctgt    2400
gctttgggga ttccctccac atgctgcacg cgcatctcgc cccagggggc actgcctgga    2460
agattcagga gcctgggcgg ccttcgctta ctctcacctg cttctgagtt gcccaggaga    2520
ccactggcag atgtcccggc gaagagaaga gacacattgt tggaagaagc agcccatgac    2580
agctccccctt cctgggactc gccctcatcc tcttcctgct ccccttcctg gggtgcagcc    2640
taaaaggacc tatgtcctca caccattgaa accactagtt ctgtcccccc aggagacctg    2700
gttgtgtgtg tgtgagtggt tgaccttcct ccatcccctg gtccttccct tcccttcccg    2760
aggcacagag agacagggca ggatccacgt gcccattgtg gaggcagaga aaagagaaag    2820
tgttttatat acggtactta tttaatatcc cttttaatt agaaattaaa acagttaatt    2880
taattaaaga gtagggtttt ttttcagtat tcttggttaa tatttaattt caactattta    2940
tgagatgtat cttttgctct ctcttgctct cttatttgta ccggttttg tatataaaat    3000
tcatgtttcc aatctctctc tccctgatcg gtgacagtca ctagcttatc ttgaacagat    3060
atttaatttt gctaacactc agctctgccc tccccgatcc cctggctccc cagcacacat    3120
tcctttgaaa taaggtttca atatacatct acatactata tatatatttg gcaacttgta    3180
tttgtgtgta tatatatata tatgtttta tgtatatatg tgattctgat aaaatagaca    3240
ttgctattct gttttttata tgtaaaaaca aacaagaaa aaatagagaa ttctacatac    3300
taaatctctc tccttttttta attttaatat ttgttatcat ttatttattg gtgctactgt    3360
ttatccgtaa taattgtggg gaaaagatat taacatcacg tctttgtctc tagtgcagtt    3420
tttcgagata ttccgtagta catatttatt tttaaacaac gacaaagaaa tacagatata    3480
tcttaaaaaa aaaaaagcat tttgtattaa agaatttaat tctgatctca aaaaaaaaa    3540
aa                                                                   3542
```

<210> SEQ ID NO 9

<211> LENGTH: 3410
<212> TYPE: DNA
<213> ORGANISM: Homo sapiens

<400> SEQUENCE: 9

```
ggcttgggc agccgggtag ctcggaggtc gtggcgctgg gggctagcac cagcgctctg      60
tcgggaggcg cagcggttag gtggaccggt cagcggactc accggccagg gcgctcggtg     120
ctggaatttg atattcattg atccgggttt tatccctctt cttttttctt aaacattttt     180
ttttaaaact gtattgtttc tcgttttaat ttattttgc ttgccattcc ccacttgaat      240
cgggccgacg gcttgggag attgctctac ttccccaaat cactgtggat tttggaaacc     300
agcagaaaga ggaaagaggt agcaagagct ccagagagaa gtcgaggaag agagagacgg    360
ggtcagagag agcgcgcggg cgtgcgagca gcgaaagcga caggggcaaa gtgagtgacc    420
tgcttttggg ggtgaccgcc ggagcgcggc gtgagccctc ccccttggga tcccgcagct    480
gaccagtcgc gctgacggac agacagacag acaccgcccc cagccccagc taccacctcc    540
tccccggccg gcggcggaca gtggacgcgg cggcgagccg cgggcagggg ccggagcccg    600
cgcccgagg cggggtggag ggggtcgggg ctcgcggcgt cgcactgaaa ctttcgtcc      660
aacttctggg ctgttctcgc ttcggaggag ccgtggtccg cgcggggaa gccgagccga     720
gcggagccgc gagaagtgct agctcgggcc gggaggagcc gcagccggag gaggggagg    780
aggaagaaga gaaggaagag gagaggggc cgcagtggcg actcggcgct cggaagccgg    840
gctcatggac gggtgaggcg gcggtgtgcg cagacagtgc tccagccgcg cgcgctcccc   900
aggccctggc ccgggcctcg ggccggggag gaagagtagc tcgccgaggc gccgaggaga   960
gcgggccgcc ccacagcccg agccggagag ggagcgcgag ccgcgccggc cccggtcggg  1020
cctccgaaac catgaacttt ctgctgtctt gggtgcattg gagccttgcc ttgctgctct  1080
acctccacca tgccaagtgg tcccaggctg cacccatggc agaaggagga gggcagaatc  1140
atcacgaagt ggtgaagttc atggatgtct atcagcgcag ctactgccat ccaatcgaga  1200
ccctggtgga catcttccag gagtaccctg atgagatcga gtacatcttc aagccatcct  1260
gtgtgcccct gatgcgatgc ggggctgct gcaatgacga gggcctggag tgtgtgccca   1320
ctgaggagtc caacatcacc atgcagatta tgcggatcaa acctcaccaa ggccagcaca   1380
taggagagat gagcttccta cagcacaaca aatgtgaatg cagaccaaag aaagatagag  1440
caagacaaga aaatgtgac aagccgaggc ggtgagccgg gcaggaggaa ggagcctccc    1500
tcagggtttc gggaaccaga tctctcacca ggaaagactg atacgaacg atcgatacag    1560
aaaccacgct gccgccacca caccatcacc atcgacagaa cagtccttaa tccagaaacc    1620
tgaaatgaag gaagaggaga ctctgcgcag agcactttgg gtccggaggg cgagactccg   1680
gcggaagcat tcccgggcgg gtgacccagc acggtccctc ttggaattgg attcgccatt   1740
ttatttttct tgctgctaaa tcaccgagcc cggaagatta gagagttta tttctgggat   1800
tcctgtagac acacccaccc acatacatac atttatatat atatatatta tatatatata   1860
aaaataaata tctctatttt atatatataa aatatatata ttctttttttt aaattaacag   1920
tgctaatgtt attggtgtct tcactggatg tatttgactg ctgtggactt gagttgggag    1980
gggaatgttc ccactcagat cctgacaggg aagaggagga gatgagagac tctggcatga    2040
tcttttttttt gtcccacttg gtggggccag ggtcctctcc cctgcccagg aatgtgcaag   2100
gccagggcat gggggcaaat atgacccagt ttggggaaca ccgacaaacc cagccctggc    2160
gctgagcctc tctaccccag gtcagacgga cagaaagaca gatcacaggt acaggatga    2220
```

```
ggacaccggc tctgaccagg agtttgggga gcttcaggac attgctgtgc tttggggatt    2280
ccctccacat gctgcacgcg catctcgccc ccaggggcac tgcctggaag attcaggagc    2340
ctgggcggcc ttcgcttact ctcacctgct tctgagttgc ccaggagacc actggcagat    2400
gtcccggcga agagaagaga cacattgttg gaagaagcag cccatgacag ctccccttcc    2460
tgggactcgc cctcatcctc ttcctgctcc ccttcctggg gtgcagccta aaaggaccta    2520
tgtcctcaca ccattgaaac cactagttct gtccccccag gagacctggt tgtgtgtgtg    2580
tgagtggttg accttcctcc atccctggt  ccttcccttc ccttcccgag gcacagagag    2640
acagggcagg atccacgtgc ccattgtgga ggcagagaaa agagaaagtg ttttatatac    2700
ggtacttatt taatatccct ttttaattag aaattaaaac agttaattta attaaagagt    2760
agggttttt  ttcagtattc ttggttaata tttaatttca actatttatg agatgtatct    2820
tttgctctct cttgctctct tatttgtacc ggttttgta  tataaaattc atgtttccaa    2880
tctctctctc cctgatcggt gacagtcact agcttatctt gaacagatat ttaattttgc    2940
taacactcag ctctgccctc cccgatcccc tggctcccca gcacacattc ctttgaaata    3000
aggtttcaat atacatctac atactatata tatatttggc aacttgtatt tgtgtgtata    3060
tatatatata tatgtttatg tatatatgtg attctgataa aatagacatt gctattctgt    3120
ttttatatg  taaaaacaaa acaagaaaaa atagagaatt ctacatacta aatctctctc    3180
cttttttaat tttaatattt gttatcattt atttattggt gctactgttt atccgtaata    3240
attgtgggga aaagatatta acatcacgtc tttgtctcta gtgcagtttt tcgagatatt    3300
ccgtagtaca tatttatttt taaacaacga caaagaaata cagatatatc ttaaaaaaaa    3360
aaaagcattt tgtattaaag aatttaattc tgatctcaaa aaaaaaaaaa               3410

<210> SEQ ID NO 10
<211> LENGTH: 5895
<212> TYPE: DNA
<213> ORGANISM: Homo sapiens

<400> SEQUENCE: 10
gcagttggtg aaactcctct gtctcccgct catcttttca ttgctcgttc ccctccttcc      60
cgcagacacc cggacctccc ctgggcgcca gctccgcggc tccaacgggt ccagaaacaa     120
gccggatttt tttttttttct tcctggaaat tggcttggt gtgtgttgcc ctacctccct     180
cctcccctc  ccacccacag ccccccccg  gcctttttt  ttttttttt  ttttttgag     240
acatggcccg ggcagtggct cctggaagag gaacaagtgt gggaaagggg agaggaagcc     300
ggagctaaat gacaggatgc aggcgacttg agacacaaaa agagaagcgt tcctctcgga     360
tccaggcatt gcctcgctgc tttctttttct ccaagacggg ctgaggattg tacagctcta     420
ggcggagttg gggctcttcg gatcgcttag attctcctct ttgctgcatt tccccccacg     480
tcctcgttct cccgcgtctg cctgcggacc cggagaaggg agaatggaga ggggctgcc     540
gctcctctgc gccgtgctcg ccctcgtcct cgcccggcc  ggcgcttttc gcaacgataa     600
atgtggcgat actataaaaa ttgaaagccc cgggtacctt acatctcctg gttatcctca     660
ttcttatcac ccaagtgaaa aatgcgaatg gctgattcag gctccggacc cataccagag     720
aattatgatc aacttcaacc ctcacttcga tttggaggac agagactgca agtatgacta     780
cgtggaagtc ttcgatggag aaaatgaaaa tggacatttt aggggaaagt ctctgtggaaa    840
gatagcccct cctcctgttg tgtcttcagg gccatttctt tttatcaaat ttgtctctga     900
```

```
ctacgaaaca catggtgcag gattttccat acgttatgaa attttcaaga gaggtcctga    960
atgttcccag aactacacaa cacctagtgg agtgataaag tcccccggat tccctgaaaa   1020
atatcccaac agccttgaat gcacttatat tgtctttgcg ccaaagatgt cagagattat   1080
cctggaattt gaaagctttg acctggagcc tgactcaaat cctccagggg ggatgttctg   1140
tcgctacgac cggctagaaa tctgggatgg attccctgat gttggccctc acattgggcg   1200
ttactgtgga cagaaaacac caggtcgaat ccgatcctca tcgggcattc tctccatggt   1260
tttttacacc gacagcgcga tagcaaaaga aggtttctca gcaaactaca gtgtcttgca   1320
gagcagtgtc tcagaagatt tcaaatgtat ggaagctctg gcatggaat caggagaaat    1380
tcattctgac cagatcacag cttcttccca gtatagcacc aactggtctg cagagcgctc   1440
ccgcctgaac taccctgaga atgggtggac tcccggagag gattcctacc gagagtggat   1500
acaggtagac ttgggccttc tgcgctttgt cacggctgtc gggacacagg gcgccatttc   1560
aaaagaaacc aagaagaaat attatgtcaa gacttacaag atcgacgtta gctccaacgg   1620
ggaagactgg atcaccataa agaaggaaa caaacctgtt ctctttcagg aaacaccaa     1680
ccccacagat gttgtggttg cagtattccc caaaccactg ataactcgat tgtccgaat    1740
caagcctgca acttgggaaa ctggcatatc tatgagattt gaagtatacg gttgcaagat   1800
aacagattat ccttgctctg gaatgttggg tatggtgtct ggacttattt ctgactccca   1860
gatcacatca tccaaccaag gggacagaaa ctggatgcct gaaaacatcc gcctggtaac   1920
cagtcgctct ggctgggcac ttccacccgc acctcattcc tacatcaatg agtggctcca   1980
aatagacctg ggggaggaga agatcgtgag gggcatcatc attcagggtg ggaagcaccg   2040
agagaacaag gtgttcatga ggaagttcaa gatcgggtac agcaacaacg gctcggactg   2100
gaagatgatc atggatgaca gcaaacgcaa ggcgaagtct tttgagggca acaacaacta   2160
tgatacacct gagctgcgga cttttccagc tctctccacg cgattcatca ggatctaccc   2220
cgagagagcc actcatggcg gactgggggct cagaatggag ctgctgggct gtgaagtgga   2280
agcccctaca gctggaccga ccactcccaa cgggaacttg gtggatgaat gtgatgacga   2340
ccaggccaac tgccacagtg gaacaggtga tgacttccag ctcacaggtg gcaccactgt   2400
gctggccaca gaaaagccca cggtcataga cagcaccata caatcagagt ttccaacata   2460
tggttttaac tgtgaatttg gctggggctc tcacaagacc ttctgccact gggaacatga   2520
caatcacgtg cagctcaagt ggagtgtgtt gaccagcaag acgggaccca ttcaggatca   2580
cacaggagat ggcaacttca tctattccca agctgacgaa aatcagaagg caaagtggc    2640
tcgcctggtg agccctgtgg tttattccca gaactctgcc cactgcatga ccttctggta   2700
tcacatgtct gggtcccacg tcggcacact cagggtcaaa ctgcgctacc agaagccaga   2760
ggagtacgat cagctggtct ggatggccat tggacaccaa ggtgaccact ggaaggaagg   2820
gcgtgtcttg ctccacaagt ctctgaaact ttatcaggtg attttcgagg gcgaaatcgg   2880
aaaaggaaac cttggtggga ttgctgtgga tgacattagt attaataacc acatttcaca   2940
agaagattgt gcaaaaccag cagacctgga taaaagaac ccagaaatta aaattgatga    3000
aacagggagc acgccaggat acgaaggtga aggagaaggt gacaagaaca tctccaggaa   3060
gccaggcaat gtgttgaaga ccttagaccc catcctcatc accatcatag ccatgagtgc   3120
cctgggggtc ctcctggggg ctgtctgtgg ggtcgtgctg tactgtgcct gttggcataa   3180
tgggatgtca gaaagaaact tgtctgccct ggagaactat aactttgaac ttgtggatgg   3240
tgtgaagttg aaaaaagaca aactgaatac acagagtact tattcggagg catgaaggca   3300
```

```
gacagagatg aaaagacagt caaaggacgg aagtggaagg acgggagtga gctggggagc    3360
tgttgatctt tcactataca ggctgggaag tgtgttgatg accactgagc caggcttttc    3420
tcaggagctt caatgagtat ggccgacaga catggacaag gagctgtgtt caccatcgga    3480
ctcatgtgca gtcagctttt ttcctgttgg tttcatttga ataatcagat gctggtgttg    3540
agaccaagta tgattgacat aatcattcat ttcgaccccc cctgcccctc tctctctctc    3600
tcctctcccc tttgtggatt ctttttggaa actgagcgaa atccaagatg ctggcaccaa    3660
gcgtattccg tgtggcccct tggatggaca tgctacctga acccagtgc ccagaatata    3720 ctagaatcac cgcatttcag tggactcctg aagttgtact tgtgtataat tgcccgcgtc    3780
gtgcataggc aaagaaggat taggctgttt tcttttaaa gtactgtagc ctcagtactg    3840
gtgtagtgtg tcagctctgt ttacgaagca atactgtcca gttttcttgc tgttttccg    3900 gtgttgtact aaacctcgtg cttgtgaact ccatacagaa aacggtgcca tccctgaaca    3960
cggctggcca ctgggtatac tgctgacaac cgcaacaaca aaaacacaaa tccttggcac    4020
tggctagtct atgtcctctc aagtgccttt tgtttgtac tggttcattg tgttacatta    4080
acgacccact ctgcttcttg ctggtgaaag ccctgctctt taatcaaact ctggtggccc    4140
actgactaag aagaaagttt attttcgtgt gagatgccag cccctccggg caggcaaggg    4200
ctctgaagat ttgcaacgt ggcttaattg ttctgctttt tctgtagttc aatttcatgt    4260
ttcttgaccc ttttgtataa agctacaata ttctctctta ttgttctttc atatggaatg    4320
tattttcaaa tgtaaactct cttctctttc tctctcctat ctctctgtct tttttctctc    4380
ttagaattgg aggatttgcc attgtccagg aaagaaactt gcagctttaa cctgctggga    4440
atggcaaacg attttactag actttatgtt taaaaataaa taataaggg aaattcctaa    4500 cttttgccctc caaagtctaa ctttggtttt cttgttaact ggttaaagtg acagtatctt    4560
ttttccttat ctattctatt caaaatgacc tttgatagaa atgttggcat ttagtagaaa    4620
tagtgataag ttgaggaaag aaataataca aattggcttt caagtgagac ccaaaggaag    4680
aactggataa atcttccaa atccaaaagc atgagatttt tctatccaaa tatgcaaaaa    4740
tgacccaaga gaactttctt attttgctac tgagtcacac aagggaagtg gaaggaagaa    4800
cagttaattt aagaatgaaa ctataaatcc tgatgcctgg gggtcaagta ttttaagata    4860
agagggggaa aaacacataa agtcaaacaa atgttttaaa aattcataac agcaaccttg    4920
aaaaaataga cttaaatgaa tgcttctaga aacttccagc ggctcacaaa gaataagcct    4980
gccttagggc tggcaacatc taagcctcta acagcacagg gaagcaaata tcttaccagg    5040
cagcctatga attaacccaa agaagctttg gttggttttg gtggattttt atcatgccat    5100
gttggacatg agattttta gatcttcctt cccacattgc tagacgtctc actcaaagac    5160
atttgttggg agtcacattt gcatcataga cgagacagtc cattcatctt agttaaattg    5220
gattgagaat gccttttgtt tccaggaaaa tattgatcac catgaaagaa gaatagtttt    5280
ttgtccccag agacattcat ttagttgata taatcctacc agaaggaaag cactaagaaa    5340
cactcgtttg ttgttttaa aggcaacaga cttaaagttg tcctcagcca aggaaaaatg    5400
atactgcaac tttaaaattt aaagtatctt gcactgataa atatatttaa aaattatatg    5460
tttataaagt tattaatttg taaaggcagt gttacaaaat gttcagttta tattgtttta    5520
gattgttttg taattttta aggtgtaaaa taacatattt tttctttatg gaatctata    5580 aaactttctg tagtaaaatg ttttcatttt actggtatat tattgcttca tgttttgtac    5640
```

-continued

| | |
|---|---:|
| catcataaga ttttgtgcag attttttttta cagaaattat tattttctat gacaatatga | 5700 |
| cacttgtaaa ttgttgtttc aaaatgaaca gcgaagcctt aactttaaat gacatttgta | 5760 |
| ttctcagaca ctgagtagca taaaaaccac atagaactga actgtaactt aaattccaaa | 5820 |
| ctatgactac tacattccaa agaaacagtt gaattaaaca ttttcataaa atatcccaca | 5880 |
| aaaaaaaaaa aaaaa | 5895 |

<210> SEQ ID NO 11
<211> LENGTH: 7123
<212> TYPE: DNA
<213> ORGANISM: Homo sapiens

<400> SEQUENCE: 11

| | |
|---|---:|
| atcgaggtcc gcgggaggct cggagcgcgc caggcggaca ctcctctcgg ctcctccccg | 60 |
| gcagcggcgg cggctcggag cgggctccgg ggctcgggtg cagcggccag cgggcgcctg | 120 |
| gcggcgagga ttaccggggg aagtggttgt ctcctggctg gagccgcgag acgggcgctc | 180 |
| agggcgcggg gccggcggcg gcgaacgaga ggacggactc tggcggccgg gtcgttggcc | 240 |
| gcggggagcg cgggcaccgg gcgagcaggc cgcgtcgcgc tcaccatggt cagctactgg | 300 |
| gacaccgggg tcctgctgtg cgcgctgctc agctgtctgc ttctcacagg atctagttca | 360 |
| ggttcaaaat taaagatcc tgaactgagt ttaaaaggca cccagcacat catgcaagca | 420 |
| ggccagacac tgcatctcca atgcaggggg aagcagccc ataaatggtc tttgcctgaa | 480 |
| atggtgagta aggaaagcga aaggctgagc ataactaaat ctgcctgtgg aagaaatggc | 540 |
| aaacaattct gcagtacttt aaccttgaac acagctcaag caaaccacac tggcttctac | 600 |
| agctgcaaat atctagctgt acctacttca aagaagaagg aaacagaatc tgcaatctat | 660 |
| atatttatta gtgatacagg tagacctttc gtagagatgt acagtgaaat ccccgaaatt | 720 |
| atacacatga ctgaaggaag ggagctcgtc attccctgcc gggttacgtc acctaacatc | 780 |
| actgttactt aaaaaagtt tccacttgac actttgatcc ctgatggaaa acgcataatc | 840 |
| tgggacagta gaaagggctt catcatatca aatgcaacgt acaaagaaat agggcttctg | 900 |
| acctgtgaag caacagtcaa tgggcatttg tataagacaa actatctcac acatcgacaa | 960 |
| accaatacaa tcatagatgt ccaaataagc acaccacgcc cagtcaaatt acttagaggc | 1020 |
| catactcttg tcctcaattg tactgctacc actcccttga acacgagagt tcaaatgacc | 1080 |
| tggagttacc ctgatgaaaa aaataagaga gcttccgtaa ggcgacgaat tgaccaaagc | 1140 |
| aattcccatg ccaacatatt ctacagtgtt cttactattg acaaaatgca gaacaaagac | 1200 |
| aaaggacttt atacttgtcg tgtaaggagt ggaccatcat tcaaatctgt taacacctca | 1260 |
| gtgcatatat atgataaagc attcatcact gtgaaacatc gaaaacagca ggtgcttgaa | 1320 |
| accgtagctg gcaagcggtc ttaccggctc tctatgaaag tgaaggcatt ccctcgccg | 1380 |
| gaagttgtat ggtaaaaga tgggttacct gcgactgaga aatctgctcg ctatttgact | 1440 |
| cgtggctact cgttaattat caaggacgta actgaagagg atgcagggaa ttatacaatc | 1500 |
| ttgctgagca taaaacagtc aaatgtgttt aaaaaacctca ctgccactct aattgtcaat | 1560 |
| gtgaaacccc agatttacga aaaggccgtg tcatcgtttc cagacccggc tctctaccca | 1620 |
| ctgggcagca gacaaatcct gacttgtacc gcatatggta tccctcaacc tacaatcaag | 1680 |
| tggttctggc acccctgtaa ccataatcat tccgaagcaa ggtgtgactt tgttccaat | 1740 |
| aatgaagagt cctttatcct ggatgctgac agcaacatgg aaacagaat tgagagcatc | 1800 |
| actcagcgca tggcaataat agaaggaaag aataagatgg ctagcacctt ggttgtggct | 1860 |

```
gactctagaa tttctggaat ctacatttgc atagcttcca ataaagttgg gactgtggga    1920
agaaacataa gcttttatat cacagatgtg ccaaatgggt ttcatgttaa cttggaaaaa    1980
atgccgacgg aaggagagga cctgaaactg tcttgcacag ttaacaagtt cttatacaga    2040
gacgttactt ggattttact gcggacagtt aataacagaa caatgcacta cagtattagc    2100
aagcaaaaaa tggccatcac taaggagcac tccatcactc ttaatcttac catcatgaat    2160
gtttccctgc aagattcagg cacctatgcc tgcagagcca ggaatgtata cacaggggaa    2220
gaaatcctcc agaagaaaga aattacaatc agagatcagg aagcaccata cctcctgcga    2280
aacctcagtg atcacacagt ggccatcagc agttccacca ctttagactg tcatgctaat    2340
ggtgtccccg agcctcagat cacttggttt aaaaacaacc acaaaataca acaagagcct    2400
ggaattattt taggaccagg aagcagcacg ctgtttattg aaaagagtca c agaagaggat    2460 gaaggtgtct atcactgcaa agccaccaac cagaagggct ctgtggaaag ttcagcatac    2520
ctcactgttc aaggaacctc ggacaagtct aatctggagc tgatcactct aacatgcacc    2580
tgtgtggctg cgactctctt ctggctccta ttaaccctct ttatccgaaa aatgaaaagg    2640
tcttcttctg aaataaagac tgactaccta tcaattataa tggacccaga tgaagttcct    2700
ttggatgagc agtgtgagcg gctcccttat gatgccagca gtgggagtt tgcccgggag    2760 agacttaaac tgggcaaatc acttggaaga ggggcttttg aaaagtggt tcaagcatca    2820 gcatttggca ttaagaaatc acctacgtgc cggactgtgg ctgtgaaaat gctgaaagag    2880
ggggccacgg ccagcgagta caaagctctg atgactgagc taaaaatctt gacccacatt    2940
ggccaccatc tgaacgtggt taacctgctg ggagcctgca ccaagcaagg agggcctctg    3000
atggtgattg ttgaatactg caaatatgga aatctctcca actacctcaa gagcaaacgt    3060
gacttatttt ttctcaacaa ggatgcagca ctacacatgg agcctaagaa agaaaaaatg    3120
gagccaggcc tggaacaagg caagaaacca agactagata gcgtcaccag cagcgaaagc    3180
tttgcgagct ccggctttca ggaagataaa agtctgagtg atgttgagga agaggaggat    3240
tctgacggtt tctacaagga gcccatcact atggaagatc tgatttctta cagttttcaa    3300
gtggccagag gcatggagtt cctgtcttcc agaaagtgca ttcatcggga cctggcagcg    3360
agaaacattc ttttatctga gaacaacgtg gtgaagattt gtgattttgg ccttgcccgg    3420
gatatttata agacccccga ttatgtgaga aaggagata ctcgacttcc tctgaaatgg    3480
atggctcctg aatctatctt tgacaaaatc tacagcacca agagcgacgt gtggtcttac    3540
ggagtattgc tgtgggaaat cttctcctta ggtgggtctc catacccagg agtacaaatg    3600
gatgaggact tttgcagtcg cctgagggaa ggcatgagga tgagagctcc tgagtactct    3660
actcctgaaa tctatcagat catgctggac tgctggcaca gagacccaaa agaaaggcca    3720
agatttgcag aacttgtgga aaaactaggt gatttgcttc aagcaaatgt acaacaggat    3780
ggtaaagact acatcccaat caatgccata ctgacaggaa atagtgggtt tacatactca    3840
actcctgcct tctctgagga cttcttcaag gaaagtattt cagctccgaa gtttaattca    3900
ggaagctctg atgatgtcag atacgtaaat gctttcaagt tcatgagcct ggaaagaatc    3960 aaaaccttg aagaactttt accgaatgcc acctccatgt ttgatgacta ccagggcgac    4020
agcagcactc tgttggcctc tccatgctg aagcgcttca cctggactga cagcaaaccc    4080
aaggcctcgc tcaagattga cttgagagta accagtaaaa gtaaggagtc ggggctgtct    4140
gatgtcagca ggcccagttt ctgccattcc agctgtgggc acgtcagcga aggcaagcgc    4200
```

```
aggttcacct acgaccacgc tgagctggaa aggaaaatcg cgtgctgctc cccgccccca    4260
gactacaact cggtggtcct gtactccacc ccacccatct agagtttgac acgaagcctt    4320
atttctagaa gcacatgtgt atttataccc ccaggaaact agcttttgcc agtattatgc    4380
atatataagt ttacacccttt atcttttccat gggagccagc tgcttttgt gattttttta    4440 atagtgcttt ttttttttg actaacaaga atgtaactcc agatagagaa atagtgacaa    4500
gtgaagaaca ctactgctaa atcctcatgt tactcagtgt tagagaaatc cttcctaaac    4560
ccaatgactt ccctgctcca accccgcca cctcagggca cgcaggacca gtttgattga    4620
ggagctgcac tgatcaccca atgcatcacg tacccactg ggccagccct gcagcccaaa    4680
acccagggca acaagcccgt tagccccagg gatcactggc tggcctgagc aacatctcgg    4740
gagtcctcta gcaggcctaa gacatgtgag gaggaaaagg aaaaaaagca aaaagcaagg    4800
gagaaaagag aaaccgggag aaggcatgag aaagaatttg agacgcacca tgtgggcacg    4860 gaggggggacg gggctcagca atgccatttc agtggcttcc cagctctgac ccttctacat    4920
ttgagggccc agccaggagc agatggacag cgatgagggg acattttctg gattctggga    4980
ggcaagaaaa ggacaaatat ctttttttgga actaaagcaa attttagaac tttacctatg    5040
gaagtggttc tatgtccatt ctcattcgtg gcatgtttttg atttgtagca ctgagggtgg    5100
cactcaactc tgagcccata ctttttggctc ctctagtaag atgcactgaa aacttagcca    5160
gagttaggtt gtctccaggc catgatggcc ttacactgaa aatgtcacat tctattttgg    5220
gtattaatat atagtccaga cacttaactc aatttcttgg tattattctg ttttgcacag    5280
ttagttgtga aagaaagctg agaagaatga aaatgcagtc ctgaggagag gagttttctc    5340
catatcaaaa cgagggctga tggaggaaaa aggtcaataa ggtcaaggga aaaccccgtc    5400
tctataccaa ccaaaccaat tcaccaacac agttgggacc caaaacacag gaagtcagtc    5460
acgtttcctt ttcatttaat ggggattcca ctatctcaca ctaatctgaa aggatgtgga    5520
agagcattag ctgcgcata ttaagcactt taagctcctt gagtaaaaag gtggtatgta    5580
atttatgcaa ggtatttctc cagttgggac tcaggatatt agttaatgag ccatcactag    5640
aagaaaagcc cattttcaac tgcttttgaaa cttgcctggg gtctgagcat gatgggaata    5700
gggagacagg gtaggaaagg gcgcctactc ttcagggtct aaagatcaag tgggccttgg    5760
atcgctaagc tggctctgtt tgatgctatt tatgcaagtt agggtctatg tatttatgat    5820
gtctgcacct tctgcagcca gtcagaagct ggagaggcaa cagtggattg ctgcttcttg    5880 gggagaaag tatgcttcct tttatccatg taatttaact gtagaacctg agctctaagt    5940
aaccgaagaa tgtatgcctc tgttcttatg tgccacatcc ttgtttaaag gctctctgta    6000
tgaagagatg ggaccgtcat cagcacattc cctagtgagc ctactggctc ctggcagcgg    6060
cttttgtgga agactcacta gccagaagag aggagtggga cagtcctctc caccaagatc    6120
taaatccaaa caaagcagg ctagagccag aagagaggac aaatctttgt tcttcctctt    6180
ctttacatac gcaaaccacc tgtgcacagct ggcaatttta taaatcaggt aactggaagg    6240
aggttaaaca cagaaaaag aagacctcag tcaattctct acttttttttt tttttttccaa    6300 atcagataat agcccagcaa atagtgataa caaataaaac cttagctatt catgtcttga    6360
tttcaataat taattcttaa tcattaagag accataataa atactccttt tcaagagaaa    6420
agcaaaacca ttagaattgt tactcagctc cttcaaactc aggtttgtag catacatgag    6480
tccatccatc agtcaaagaa tggttccatc tggagtctta atgtagaaag aaaaatggaa    6540
acttgtaata atgagctagt tacaaagtgc ttgttcatta aaatagcact gaaaattgaa    6600
```

```
acatgaatta actgataata ttccaatcat ttgccattta tgacaaaaat ggttggcact      6660
aacaaagaac gagcacttcc tttcagagtt tctgagataa tgtacgtgga acagtctggg      6720
tggaatgggg ctgaaaccat gtgcaagtct gtgtcttgtc agtccaagaa gtgacaccga      6780
gatgttaatt ttagggaccc gtgccttgtt tcctagccca caagaatgca aacatcaaac      6840
agatactcgc tagcctcatt taaattgatt aaaggaggag tgcatctttg gccgacagtg      6900
gtgtaactgt atgtgtgtgt gtgtgtgtgt gtgtgtgtgt gtgtgtgggt gtatgtgtgt      6960
tttgtgcata actatttaag gaaactggaa ttttaaagtt acttttatac aaaccaagaa      7020
tatatgctac agatataaga cagacatggt ttggtcctat atttctagtc atgatgaatg      7080
tattttgtat accatcttca tataataaac ttccaaaaac aca                       7123

<210> SEQ ID NO 12
<211> LENGTH: 6055
<212> TYPE: DNA
<213> ORGANISM: Homo sapiens

<400> SEQUENCE: 12
actgagtccc gggaccccgg gagagcggtc aatgtgtggt cgctgcgttt cctctgcctg        60
cgccgggcat cacttgcgcg ccgcagaaag tccgtctggc agcctggata tcctctccta       120
ccggcacccg cagcgcccc tgcagccgcg gtcggcgccc gggctcccta gcccgtgcg        180 ctcaactgtc ctgcgctgcg gggtgccgcg agttccacct ccgcgcctcc ttctctagac       240
aggcgctggg agaaagaacc ggctcccgag ttctgggcat ttcgcccggc tcgaggtgca       300
ggatgcagag caaggtgctg ctggccgtcg ccctgtggct ctgcgtggag acccgggccg       360
cctctgtggg tttgcctagt gtttctcttg atctgcccag gctcagcata caaaagaca        420 tacttacaat taaggctaat acaactcttc aaattacttg caggggacag agggacttgg       480
actggctttg gcccaataat cagagtggca gtgagcaaag ggtggaggtg actgagtgca       540
gcgatggcct cttctgtaag acactcacaa ttccaaaagt gatcggaaat gacactggag       600
cctacaagtg cttctaccgg gaaactgact tggcctcggt catttatgtc tatgttcaag       660
attacagatc tccattatt gcttctgtta gtgaccaaca tggagtcgtg tacattactg        720
agaacaaaaa caaaactgtg gtgattccat gtctcgggtc catttcaaat ctcaacgtgt       780
cactttgtgc aagatacca gaaaagagat ttgttcctga tggtaacaga atttcctggg        840
acagcaagaa gggctttact attcccagct acatgatcag ctatgctggc atggtcttct       900
gtgaagcaaa aattaatgat gaaagttacc agtctattat gtacatagtt gtcgttgtag       960
ggtataggat ttatgatgtg gttctgagtc cgtctcatgg aattgaacta tctgttggag      1020
aaaagcttgt cttaaattgt acagcaagaa ctgaactaaa tgtggggatt gacttcaact      1080
gggaataccc ttcttcgaag catcagcata agaaacttgt aaaccgagac ctaaaaaccc      1140
agtctgggag tgagatgaag aaatttttga gcaccttaac tatagatggt gtaacccgga      1200
gtgaccaagg attgtacacc tgtgcagcat ccagtgggct gatgaccaag aagaacagca      1260
catttgtcag ggtccatgaa aaaccttttg ttgcttttgg aagtggcatg gaatctctgg      1320
tggaagccac ggtgggggag cgtgtcagaa tcccctgcgaa gtaccttggt tacccacccc      1380
cagaaataaa atggtataaa aatggaatac cccttgagtc caatcacaca attaaagcgg      1440
ggcatgtact gacgattatg gaagtgagtg aaagagacac aggaaattac actgtcatcc      1500
ttaccaatcc catttcaaag gagaagcaga gccatgtggt ctctctggtt gtgtatgtcc      1560
```

```
caccccagat tggtgagaaa tctctaatct ctcctgtgga ttcctaccag tacggcacca    1620
ctcaaacgct gacatgtacg gtctatgcca ttcctccccc gcatcacatc cactggtatt    1680
ggcagttgga ggaagagtgc gccaacgagc ccagccaagc tgtctcagtg acaaacccat    1740
acccttgtga agaatggaga agtgtggagg acttccaggg aggaaataaa attgaagtta    1800
ataaaaatca atttgctcta attgaaggaa aaaacaaaac tgtaagtacc cttgttatcc    1860
aagcggcaaa tgtgtcagct tgtacaaat gtgaagcggt caacaaagtc gggagaggag     1920
agagggtgat ctccttccac gtgaccaggg gtcctgaaat tactttgcaa cctgacatgc    1980
agcccactga gcaggagagc gtgtctttgt ggtgcactgc agacagatct acgtttgaga    2040
acctcacatg gtacaagctt ggcccacagc ctctgccaat ccatgtggga gagttgccca    2100
cacctgtttg caagaacttg gatactcttt ggaaattgaa tgccaccatg ttctctaata    2160
gcacaaatga cattttgatc atggagctta agaatgcatc cttgcaggac caaggagact    2220
atgtctgcct tgctcaagac aggaagacca agaaaagaca ttgcgtggtc aggcagctca    2280
cagtcctaga gcgtgtggca cccacgatca caggaaacct ggagaatcag acgacaagta    2340
ttggggaaag catcgaagtc tcatgcacgg catctgggaa tccccctcca cagatcatgt    2400
ggtttaaaga taatgagacc cttgtagaag actcaggcat tgtattgaag gatgggaacc    2460
ggaacctcac tatccgcaga gtgaggaagg aggacgaagg cctctacacc tgccaggcat    2520
gcagtgttct tggctgtgca aaagtggagg catttttcat aatagaaggt gcccaggaaa    2580
agacgaactt ggaaatcatt attctagtag gcacggcggt gattgccatg ttcttctggc    2640
tacttcttgt catcatccta cggaccgtta agcgggccaa tggagggga ctgaagacag     2700 gctacttgtc catcgtcatg gatccagatg aactcccatt ggatgaacat tgtgaacgac    2760
tgccttatga tgccagcaaa tgggaattcc ccagagaccg gctgaagcta ggtaagcctc    2820
ttggccgtgg tgcctttggc caagtgattg aagcagatgc ctttggaatt gacaagacag    2880
caacttgcag gacagtagca gtcaaaatgt tgaaagaagg agcaacacac agtgagcatc    2940
gagctctcat gtctgaactc aagatcctca ttcatattgg tcaccatctc aatgtggtca    3000
accttctagg tgcctgtacc aagccaggag ggccactcat ggtgattgtg gaattctgca    3060
aatttggaaa cctgtccact tacctgagga gcaagagaaa tgaatttgtc ccctacaaga    3120 ccaaggggc acgattccgt caagggaaag actacgttgg agcaatccct gtggatctga    3180
aacggcgctt ggacagcatc accagtagcc agagctcagc cagctctgga tttgtggagg    3240
agaagtccct cagtgatgta gaagaagagg aagctcctga agatctgtat aaggacttcc    3300
tgaccttgga gcatctcatc tgttacagct tccaagtggc taagggcatg gagttcttgg    3360
catcgcgaaa gtgtatccac agggacctgg cggcacgaaa tatcctctta tcggagaaga    3420
acgtggttaa aatctgtgac tttggcttgg cccgggatat ttataaagat ccagattatg    3480
tcagaaaagg agatgctcgc ctcccttga aatggatggc cccagaaaca attttttgaca    3540 gagtgtacac aatccagagt gacgtctggt cttttggtgt tttgctgtgg gaaatatttt    3600
ccttaggtgc ttctccatat cctggggtaa agattgatga agaattttgt aggcgattga    3660
aagaaggaac tagaatgagg gcccctgatt atactacacc agaaatgtac cagaccatgc    3720
tggactgctg gcacggggag cccagtcaga gacccacgtt tcagagttg gtggaacatt     3780 tgggaaatct cttgcaagct aatgctcagc aggatggcaa agactacatt gttcttccga    3840
tatcagagac tttgagcatg gaagaggatt ctggactctc tctgcctacc tcacctgttt    3900
cctgtatgga ggaggaggaa gtatgtgacc ccaaattcca ttatgacaac acagcaggaa    3960
```

```
tcagtcagta tctgcagaac agtaagcgaa agagccggcc tgtgagtgta aaaacatttg    4020
aagatatccc gttagaagaa ccagaagtaa aagtaatccc agatgacaac cagacggaca    4080
gtggtatggt tcttgcctca gaagagctga aaactttgga agacagaacc aaattatctc    4140
catcttttgg tggaatggtg cccagcaaaa gcagggagtc tgtggcatct gaaggctcaa    4200
accagacaag cggctaccag tccggatatc actccgatga cacagacacc accgtgtact    4260
ccagtgagga agcagaactt ttaaagctga tagagattgg agtgcaaacc ggtagcacag    4320
cccagattct ccagcctgac tcggggacca cactgagctc tcctcctgtt taaaaggaag    4380
catccacacc cccaactcct ggacatcaca tgagaggtgc tgctcagatt ttcaagtgtt    4440
gttctttcca ccagcaggaa gtagccgcat ttgattttca tttcgacaac agaaaaagga    4500
cctcggactg cagggagcca gtcttctagg catatcctgg aagaggcttg tgacccaaga    4560
atgtgtctgt gtcttctccc agtgttgacc tgatcctctt tttcattcat ttaaaaagca    4620
tttatcatgc cccctgctgc gggtctcacc atgggtttag aacaaagacg ttcaagaaat    4680
ggccccatcc tcaaagaagt agcagtacct ggggagctga cacttctgta aaactagaag    4740
ataaaccagg caatgtaagt gttcgaggtg ttgaagatgg gaaggatttg cagggctgag    4800
tctatccaag aggctttgtt taggacgtgg gtcccaagcc aagcttaag tgtggaattc     4860 ggattgataa gaaaggaagac taacgttacc ttgctttgga gagtactgga gcctgcaaat    4920
gcattgtgtt tgctctggtg gaggtgggca tggggtctgt tctgaaatgt aaagggttca    4980
gacggggttt ctggttttag aaggttgcgt gttcttcgag ttgggctaaa gtagagttcg    5040
ttgtgctgtt tctgactcct aatgagagtt ccttccagac cgttacgtgt ctcctggcca    5100
agccccagga aggaaatgat gcagctctgg ctccttgtct cccaggctga tcctttattc    5160
agaataccac aaagaaagga cattcagctc aaggctccct gccgtgttga agagttctga    5220
ctgcacaaac cagcttctgg tttcttctgg aatgaatacc ctcatatctg tcctgatgtg    5280
atatgtctga gactgaatgc gggaggttca atgtgaagct gtgtgtggtg tcaaagtttc    5340
aggaaggatt ttaccctttt gttcttcccc ctgtccccaa cccactctca ccccgcaacc    5400
catcagtatt ttagttattt ggcctctact ccagtaaacc tgattgggtt tgttcactct    5460
ctgaatgatt attagccaga cttcaaaatt attttatagc ccaaattata acatctattg    5520
tattatttag acttttaaca tatagagcta tttctactga ttttgccct tgttctgtcc      5580 ttttttttcaa aaagaaaat gtgttttttg tttggtacca tagtgtgaaa tgctgggaac    5640
aatgactata agacatgcta tggcacatat atttatagtc tgtttatgta gaaacaaatg    5700
taatatatta aagccttata tataatgaac tttgtactat tcacattttg tatcagtatt    5760
atgtagcata acaaaggtca taatgctttc agcaattgat gtcattttat taagaacat      5820 tgaaaaactt gaaggaatcc ctttgcaagg ttgcattact gtacccatca tttctaaaat    5880
ggaagagggg gtggctgggc acagtggccg acacctaaaa acccagcact tggggggcc     5940 aaggtgggag gatcgcttga gcccaggagt tcaagaccag tctggccaac atggtcagat    6000
tccatctcaa agaaaaaagg taaaaataaa ataaaatgga gaagaaggaa tcaga          6055
```

<210> SEQ ID NO 13
<211> LENGTH: 3665
<212> TYPE: DNA
<213> ORGANISM: Homo sapiens
<400> SEQUENCE: 13

-continued

```
ggcttggggc agccgggtag ctcggaggtc gtggcgctgg gggctagcac cagcgctctg      60
tcgggaggcg cagcggttag gtggaccggt cagcggactc accggccagg gcgctcggtg     120
ctggaatttg atattcattg atccgggttt tatccctctt ctttttttctt aaacattttt    180
ttttaaaact gtattgtttc tcgttttaat ttattttttgc ttgccattcc ccacttgaat    240
cgggccgacg gcttggggag attgctctac ttccccaaat cactgtggat tttggaaacc    300
agcagaaaga ggaaagaggt agcaagagct ccagagagaa gtcgaggaag agagagacgg    360
ggtcagagag agcgcgcggg cgtgcgagca gcgaaagcga caggggcaaa gtgagtgacc    420
tgcttttggg ggtgaccgcc ggagcgcggc gtgagccctc cccccttggga tcccgcagct   480
gaccagtcgc gctgacggac agacagacag acaccgcccc cagccccagc taccacctcc    540
tccccggccg gcggcggaca gtggacgcgg cggcgagccg cgggcagggg ccggagcccg    600
cgcccggagg cggggtggag ggggtcgggg ctcgcggcgt cgcactgaaa ctttttcgtcc   660
aacttctggg ctgttctcgc ttcggaggag ccgtggtccg cgcgggggaa gccgagccga    720
gcggagccgc gagaagtgct agctcgggcc gggaggagcc gcagccggag gaggggggagg   780
aggaagaaga gaaggaagag gagaggggggc cgcagtggcg actcggcgct cggaagccgg   840
gctcatggac gggtgaggcg gcggtgtgcg cagacagtgc tccagccgcg cgcgctcccc    900
aggccctggc ccgggcctcg ggccggggag gaagagtagc tcgccgaggc gccgaggaga    960
gcgggccgcc ccacagcccg agccggagag ggagcgcgag ccgcgccggc cccggtcggg   1020
cctccgaaac catgaacttt ctgctgtctt gggtgcattg gagccttgcc ttgctgctct   1080
acctccacca tgccaagtgg tcccaggctg cacccatggc agaaggagga gggcagaatc   1140
atcacgaagt ggtgaagttc atggatgtct atcagcgcag ctactgccat ccaatcgaga   1200
ccctggtgga catcttccag gagtaccctg atgagatcga gtacatcttc aagccatcct   1260
gtgtgccct gatgcgatgc gggggctgct gcaatgacga gggcctggag tgtgtgccca    1320
ctgaggagtc caacatcacc atgcagatta tgcggatcaa acctcaccaa ggccagcaca   1380
taggagagat gagcttccta cagcacaaca aatgtgaatg cagaccaaag aaagatagag   1440
caagacaaga aaaaaaatca gttcgaggaa agggaaaggg gcaaaaacga aagcgcaaga   1500
aatcccggta taagtcctgg agcgtgtacg ttggtgcccg ctgctgtcta atgccctgga   1560
gcctccctgg cccccatccc tgtgggcctt gctcagagcg gagaaagcat tgtttgtac   1620
aagatccgca gacgtgtaaa tgttcctgca aaaacacaga ctcgcgttgc aaggcgaggc   1680
agcttgagtt aaacgaacgt acttgcagat gtgacaagcc gaggcggtga gccgggcagg   1740
aggaaggagc ctccctcagg gtttcgggaa ccagatctct caccaggaaa gactgataca   1800
gaacgatcga tacagaaacc acgctgccgc caccacacca tcaccatcga cagaacagtc   1860
cttaatccag aaacctgaaa tgaaggaaga ggagactctg cgcagagcac tttgggtccg   1920
gagggcgaga ctcggcggga agcattcccg ggcgggtgac ccagcacggt ccctcttgga   1980
attggattcg ccattttatt tttcttgctg ctaaatcacc gagcccggaa gattagagag   2040
ttttatttct gggattcctg tagacacacc cacccacata catacattta tatatatata   2100
tattatatat atataaaaat aaatatctct atttttatata tataaaatat atatattctt   2160
tttttaaatt aacagtgcta atgttattgg tgtcttcact ggatgtattt gactgctgtg   2220
gacttgagtt ggggaggggaa tgttcccact cagatcctga cagggaagag gaggagatga   2280
gagactctgg catgatcttt ttttttgtccc acttggtggg gccagggtcc tctcccctgc   2340
ccaggaatgt gcaaggccag ggcatggggg caaatatgac ccagttttgg gaacaccgac   2400
```

```
aaacccagcc ctggcgctga gcctctctac cccaggtcag acggacagaa agacagatca   2460
caggtacagg gatgaggaca ccggctctga ccaggagttt ggggagcttc aggacattgc   2520
tgtgctttgg ggattccctc cacatgctgc acgcgcatct cgcccccagg ggcactgcct   2580
ggaagattca ggagcctggg cggccttcgc ttactctcac ctgcttctga gttgcccagg   2640
agaccactgg cagatgtccc ggcgaagaga agagacacat tgttggaaga agcagcccat   2700
gacagctccc cttcctggga ctcgccctca tcctcttcct gctccccttc ctggggtgca   2760
gcctaaaagg acctatgtcc tcacaccatt gaaaccacta gttctgtccc cccaggagac   2820
ctggttgtgt gtgtgtgagt ggttgacctt cctccatccc ctggtccttc ccttcccttc   2880
ccgaggcaca gagagacagg gcaggatcca cgtgcccatt gtggaggcag agaaaagaga   2940
aagtgtttta tatacggtac ttatttaata tcccttttta attagaaatt aaaacagtta   3000
atttaattaa agagtagggt ttttttttcag tattcttggt taatatttaa tttcaactat   3060
ttatgagatg tatcttttgc tctctcttgc tctcttattt gtaccggttt ttgtatataa   3120
aattcatgtt tccaatctct ctctccctga tcggtgacag tcactagctt atcttgaaca   3180
gatatttaat tttgctaaca ctcagctctg ccctccccga tcccctggct ccccagcaca   3240
cattcctttg aaataaggtt tcaatataca tctacatact atatatatat ttggcaactt   3300
gtatttgtgt gtatatatat atatatatgt ttatgtatat atgtgattct gataaaatag   3360
acattgctat tctgtttttt atatgtaaaa acaaaacaag aaaaaataga gaattctaca   3420
tactaaatct ctctccttttt ttaattttaa tatttgttat catttattta ttggtgctac   3480
tgtttatccg taataattgt ggggaaaaga tattaacatc acgtctttgt ctctagtgca   3540 gttttttcgag atattccgta gtacatattt attttttaaac aacgacaaag aaatacagat   3600
atatcttaaa aaaaaaaaag cattttgtat taaagaattt aattctgatc tcaaaaaaaa   3660
aaaaa                                                                3665
```

<210> SEQ ID NO 14
<211> LENGTH: 1172
<212> TYPE: DNA
<213> ORGANISM: Homo sapiens

<400> SEQUENCE: 14

```
gcgatgcggg cgccccggc gggcggcccc ggcgggcacc atgagccctc tgctccgccg    60
cctgctgctc gccgcactcc tgcagctggc ccccgcccag gcccctgtct cccagcctga   120 tgccccctggc caccagagga aagtggtgtc atggatagat gtgtatactc gcgctacctg   180
ccagccccgg gaggtggtgg tgcccttgac tgtggagctc atgggcaccg tggccaaaca   240
gctggtgccc agctgcgtga ctgtgcagcg ctgtggtggc tgctgccctg acgatggcct   300
ggagtgtgtg cccactgggc agcaccaagt ccggatgcag atcctcatga tccggtaccc   360
gagcagtcag ctgggggaga tgtccctgga agaacacagc cagtgtgaat gcagacctaa   420
aaaaaaggac agtgctgtga agccagacag ggctgccact cccaccacc gtccccagcc   480 ccgttctgtt ccgggctggg actctgccca cggagcaccc tccccagctg acatcaccca   540
tcccactcca gccccaggcc cctctgccca cgctgcaccc agcaccacca cgcccctgac   600
ccccggacct gccgctgccg ctgccgacgc cgcagcttcc tccgttgcca agggcggggc   660
ttagagctca acccagacac ctgcaggtgc cggaagctgc gaaggtgaca catggctttt   720
cagactcagc agggtgactt gcctcagagg ctatatccca gtgggggaac aaagaggagc   780
```

| | |
|---|---|
| ctggtaaaaa acagccaagc ccccaagacc tcagcccagg cagaagctgc tctaggacct | 840 |
| gggcctctca gagggctctt ctgccatccc ttgtctccct gaggccatca tcaaacagga | 900 |
| cagagttgga agaggagact gggaggcagc aagagggtc acataccagc tcaggggaga | 960 |
| atggagtact gtctcagttt ctaaccactc tgtgcaagta agcatcttac aactggctct | 1020 |
| tcctcccctc actaagaaga cccaaacctc tgcataatgg gatttgggct ttggtacaag | 1080 |
| aactgtgacc cccaaccctg ataaaagaga tggaaggaaa aaaaaaaaa aaaaaaaaa | 1140 |
| aaaaaaaaa aaaaaaaaa aaaaaaaaa aa | 1172 |

<210> SEQ ID NO 15
<211> LENGTH: 2076
<212> TYPE: DNA
<213> ORGANISM: Homo sapiens

<400> SEQUENCE: 15

| | |
|---|---|
| cggggaaggg gagggaggag ggggacgagg gctctggcgg gtttggaggg gctgaacatc | 60 |
| gcggggtgtt ctggtgtccc ccgccccgcc tctccaaaaa gctacaccga cgcggaccgc | 120 |
| ggcggcgtcc tccctcgccc tcgcttcacc tcgcgggctc cgaatgcggg gagctcggat | 180 |
| gtccggtttc ctgtgaggct tttacctgac acccgccgcc tttccccggc actggctggg | 240 |
| agggcgccct gcaaagttgg gaacgcggag ccccggaccc gctcccgccg cctccggctc | 300 |
| gcccaggggg ggtcgccggg aggagcccgg gggagaggga ccaggagggg cccgcggcct | 360 |
| cgcaggggcg cccgcgcccc cacccctgcc cccgccagcg gaccggtccc ccaccccgg | 420 |
| tccttccacc atgcacttgc tgggcttctt ctctgtggcg tgttctctgc tcgccgctgc | 480 |
| gctgctcccg ggtcctcgcg aggcgcccgc cgccgccgcc gccttcgagt ccggactcga | 540 |
| cctctcggac gcggagcccg acgcgggcga ggccacggct tatgcaagca agatctggga | 600 |
| ggagcagtta cggtctgtgt ccagtgtaga tgaactcatg actgtactct acccagaata | 660 |
| ttggaaaatg tacaagtgtc agctaaggaa aggaggctgg caacataaca gagaacaggc | 720 |
| caacctcaac tcaaggacag aagagactat aaaatttgct gcagcacatt ataatacaga | 780 |
| gatcttgaaa agtattgata atgagtggag aaagactcaa tgcatgccac gggaggtgtg | 840 |
| tatagatgtg gggaaggagt ttggagtcgc gacaaacacc ttcttaaaac ctccatgtgt | 900 |
| gtccgtctac agatgtgggg gttgctgcaa tagtgagggg ctgcagtgca tgaacaccag | 960 |
| cacgagctac ctcagcaaga cgttatttga aattacagtg cctctctctc aaggccccaa | 1020 |
| accagtaaca atcagttttg ccaatcacac ttcctgccga tgcatgtcta actggatgt | 1080 |
| ttacagacaa gttcattcca ttattagacg ttccctgcca gcaacactac cacagtgtca | 1140 |
| ggcagcgaac aagacctgcc ccaccaatta catgtggaat aatcacatct gcagatgcct | 1200 |
| ggctcaggaa gattttatgt tttcctcgga tgctggagat gactcaacag atggattcca | 1260 |
| tgacatctgt ggaccaaaca aggagctgga tgaagagacc tgtcagtgtg tctgcagagc | 1320 |
| gggcttcgg cctgccagct gtggacccca caaagaacta gacagaaact catgccagtg | 1380 |
| tgtctgtaaa aacaaactct tccccagcca atgtgggcc aaccgagaat tgatgaaaaa | 1440 |
| cacatgccag tgtgtatgta aagaacctg ccccagaaat caaccctaa atcctggaaa | 1500 |
| atgtgcctgt gaatgtacag aaagtccaca gaaatgcttg ttaaaggaa agaagttcca | 1560 |
| ccaccaaaca tgcagctgtt acagacggcc atgtacgaac cgccagaagg cttgtgagcc | 1620 |
| aggattttca tatagtgaag aagtgtgtcg ttgtgtccct tcatattgga aaagaccaca | 1680 |
| aatgagctaa gattgtactg ttttccagtt catcgatttt ctattatgga aaactgtgtt | 1740 |

```
gccacagtag aactgtctgt gaacagagag acccttgtgg gtccatgcta acaaagacaa    1800
aagtctgtct ttcctgaacc atgtggataa ctttacagaa atggactgga gctcatctgc    1860
aaaaggcctc ttgtaaagac tggttttctg ccaatgacca aacagccaag attttcctct    1920
tgtgatttct ttaaaagaat gactatataa tttatttcca ctaaaaatat tgtttctgca    1980
ttcattttta tagcaacaac aattggtaaa actcactgtg atcaatattt ttatatcatg    2040
caaaatatgt ttaaaataaa atgaaaattg tattat                              2076

<210> SEQ ID NO 16
<211> LENGTH: 2128
<212> TYPE: DNA
<213> ORGANISM: Homo sapiens

<400> SEQUENCE: 16
caagacttct ctgcattttc tgccaaaatc tgtgtcagat ttaagacaca tgcttctgca     60
agcttccatg aaggttgtgc aaaaaagttt caatccagag ttgggttcca gctttctgta    120
gctgtaagca ttggtggcca caccacctcc ttacaaagca actagaacct gcggcataca    180
ttggagagat ttttttaatt ttctggacat gaagtaaatt tagagtgctt tctaatttca    240
ggtagaagac atgtccacct tctgattatt tttggagaac attttgattt ttttcatctc    300
tctctcccca cccctaagat tgtgcaaaaa aagcgtacct tgcctaattg aaataatttc    360
attggatttt gatcagaact gattatttgg ttttctgtgt gaagttttga ggtttcaaac    420
tttccttctg gagaatgcct tttgaaacaa ttttctctag ctgcctgatg tcaactgctt    480
agtaatcagt ggatattgaa atattcaaaa tgtacagaga gtgggtagtg gtgaatgttt    540
tcatgatgtt gtacgtccag ctggtgcagg gctccagtaa tgaacatgga ccagtgaagc    600
gatcatctca gtccacattg aacgatctg aacagcagat cagggctgct tctagtttgg    660
aggaactact tcgaattact cactctgagg actggaagct gtggagatgc aggctgaggc    720
tcaaaagttt taccagtatg gactctcgct cagcatccca tcggtccact aggtttgcgg    780
caactttcta tgacattgaa acactaaaag ttatagatga agaatggcaa agaactcagt    840
gcagccctag agaaacgtgc gtggaggtgg ccagtgagct ggggaagagt accaacacat    900
tcttcaagcc cccttgtgtg aacgtgttcc gatgtggtgg ctgttgcaat gaagagagcc    960
ttatctgtat gaacaccagc acctcgtaca tttccaaaca gctctttgag atatcagtgc   1020
ctttgacatc agtacctgaa ttagtgcctg ttaaagttgc caatcataca ggttgtaagt   1080
gcttgccaac agccccccgc catccatact caattatcag aagatccatc cagatccctg   1140
aagaagatcg ctgttcccat tccaagaaac tctgtcctat tgacatgcta tgggatagca   1200
acaaatgtaa atgtgttttg caggaggaaa atccacttgc tggaacagaa gaccactctc   1260
atctccagga accagctctc tgtgggccac acatgatgtt tgacgaagat cgttgcgagt   1320
gtgtctgtaa aacaccatgt cccaaagatc taatccagca ccccaaaaac tgcagttgct   1380
ttgagtgcaa agaaagtctg gagacctgct gccagaagca caagctattt cacccagaca   1440
cctgcagctg tgaggacaga tgccccttc ataccagacc atgtgcaagt ggcaaaacag   1500
catgtgcaaa gcattccgc tttccaaagg agaaagggc tgcccagggg ccccacagcc   1560
gaaagaatcc ttgattcagc gttccaagtt ccccatccct gtcatttta acagcatgct   1620 gctttgccaa gttgctgtca ctgttttttt cccaggtgtt aaaaaaaaaa tccatttta   1680 acagcaccac agtgaatcca gaccaacctt ccattcacac cagctaagga gtccctggtt   1740
```

| | |
|---|---|
| cattgatgga tgtcttctag ctgcagatgc ctctgcgcac caaggaatgg agaggagggg | 1800 |
| acccatgtaa tccttttgtt tagttttgtt tttgtttttt ggtgaatgag aaaggtgtgc | 1860 |
| tggtcatgga atggcaggtg tcatatgact tgattactcag agcagatgag gaaaactgta | 1920 |
| gtctctgagt cctttgctaa tcgcaactct tgtgaattat tctgattctt ttttatgcag | 1980 |
| aatttgattc gtatgatcag tactgacttt ctgattactg tccagcttat agtcttccag | 2040 |
| tttaatgaac taccatctga tgtttcatat ttaagtgtat ttaaagaaaa taaacaccat | 2100 |
| tattcaagcc aaaaaaaaaa aaaaaaaa | 2128 |

<210> SEQ ID NO 17
<211> LENGTH: 1758
<212> TYPE: DNA
<213> ORGANISM: Homo sapiens

<400> SEQUENCE: 17

| | |
|---|---|
| ctgctgtctg cggaggaaac tgcatcgacg gacggccgcc cagctacggg aggacctgga | 60 |
| gtggcactgg gcgcccgacg gaccatcccc gggacccgct gcccctcgg cgccccgccc | 120 |
| cgccgggccg ctccccgtcg ggttccccag ccacagcctt acctacgggc tcctgactcc | 180 |
| gcaaggcttc cagaagatgc tcgaaccacc ggccggggcc tcggggcagc agtgagggag | 240 |
| gcgtccagcc ccccactcag ctcttctcct cctgtgccag gggctccccg ggggatgagc | 300 |
| atggtggttt tccctcggag cccctggct cgggacgtct gagaagatgc cggtcatgag | 360 |
| gctgttccct tgcttcctgc agctcctggc cgggctggcg ctgcctgctg tgcccccca | 420 |
| gcagtgggcc ttgtctgctg ggaacggctc gtcagaggtg gaagtggtac ccttccagga | 480 |
| agtgtggggc cgcagctact gccgggcgct ggagaggctg gtggacgtcg tgtccgagta | 540 |
| ccccagcgag gtggagcaca tgttcagccc atcctgtgtc tccctgctgc gctgcaccgg | 600 |
| ctgctgcggc gatgagaatc tgcactgtgt gccggtggag acggccaatg tcaccatgca | 660 |
| gctcctaaag atccgttctg ggaccggcc ctcctacgtg gagctgacgt tctctcagca | 720 |
| cgttcgctgc gaatgccggc tctgcgggga gaagatgaag ccggaaagga ggagacccaa | 780 |
| gggcaggggg aagaggagga gagagaagca gagacccaca gactgccacc tgtgcggcga | 840 |
| tgctgttccc cggaggtaac ccacccttg gaggagagag accccgcacc cggctcgtgt | 900 |
| atttattacc gtcacactct tcagtgactc ctgctggtac ctgccctcta tttattagcc | 960 |
| aactgttttcc ctgctgaatg cctcgctccc ttcaagacga ggggcaggga aggacaggac | 1020 |
| cctcaggaat tcagtgcctt caacaacgtg agagaaagag agaagccagc cacagacccc | 1080 |
| tgggagcttc cgctttgaaa gaagcaagac acgtggcctc gtgaggggca agctaggccc | 1140 |
| cagaggccct ggaggtctcc aggggcctgc agaaggaaag aagggggccc tgctacctgt | 1200 |
| tcttgggcct caggctctgc acagacaagc agcccttgct ttcggagctc ctgtccaaag | 1260 |
| tagggatgcg gatcctgctg gggccgccac ggcctggctg gtgggaaggc cggcagcggg | 1320 |
| cggaggggat ccagccactt ccccctcttc ttctgaagat cagaacattc agctctggag | 1380 |
| aacagtggtt gcctgggggc ttttgccact ccttgtcccc cgtgatctcc cctcacactt | 1440 |
| tgccatttgc ttgtactggg acattgttct ttccggccaa ggtgccacca ccctgccccc | 1500 |
| cctaagagac acatacagag tgggcccgg gctggagaaa gagctgcctg gatgagaaac | 1560 |
| agctcagcca gtggggatga ggtcaccagg ggaggagcct gtgcgtccca gctgaaggca | 1620 |
| gtggcagggg agcaggttcc ccaagggccc tggcacccc acaagctgtc cctgcagggc | 1680 |
| catctgactg ccaagccaga ttctcttgaa taaagtattc tagtgtggaa aaaaaaaaa | 1740 |

```
aaaaaaaaaa aaaaaaaa                                                   1758

<210> SEQ ID NO 18
<211> LENGTH: 5672
<212> TYPE: DNA
<213> ORGANISM: Homo sapiens

<400> SEQUENCE: 18
aagcaccact gcagcagacc ttgttaattt ttttttttt tctttccaca caacagttgt      60
gcctcattat ccggtgcctg gctcggaatt ttttttttt ttttctttt tggagggttt      120
gaagtttctg tgcttcagtg actgttacag aagaagaggt gttagtgttg ccatgaggtc    180
ttgattgtct gcatttatga atgaaactga cctaaatcac ctgttacctc cagtttccag    240
attgtttgaa cttctctggc cgcacaatac aggaaggaag actaaagcag caaagggacc    300
tacagcgtct gcagcatggg ctggttaact aggattgtct gtcttttctg gggagtatta    360
cttacagcaa gagcaaacta tcagaatggg aagaacaatg tgccaaggct gaaattatcc    420
tacaaagaaa tgttggaatc aacaatgtg atcactttca atggcttggc caacagctcc     480
agttatcata ccttcctttt ggatgaggaa cggagtaggc tgtatgttgg agcaaaggat    540
cacatatttt cattcgacct ggttaatatc aaggattttc aaaagattgt gtggccagta    600
tcttacacca aagagatga atgcaagtgg gctggaaaag acatcctgaa agaatgtgct     660
aatttcatca aggtacttaa ggcatataat cagactcact tgtacgcctg tggaacgggg    720
gcttttcatc caatttgcac ctacattgaa attggacatc atcctgagga caatatttt    780
aagctggaga actcacattt tgaaaacggc cgtgggaaga gtccatatga ccctaagctg    840
ctgacagcat ccctttaat agatggagaa ttatactctg gaactgcagc tgattttatg    900
gggcgagact ttgctatctt ccgaactctt gggcaccacc acccaatcag gacagagcag    960
catgattcca ggtggctcaa tgatccaaag ttcattagtg cccacctcat ctcagagagt   1020
gacaatcctg aagatgacaa agtatacttt ttcttccgtg aaaatgcaat agatggagaa   1080
cactctggaa aagctactca cgctagaata ggtcagatat gcaagaatga ctttgggggg   1140
cacagaagtc tggtgaataa atggacaaca ttcctcaaag ctcgtctgat ttgctcagtg   1200
ccaggtccaa atggcattga cactcatttt gatgaactgc aggatgtatt cctaatgaac   1260
tttaaagatc ctaaaaatcc agttgtatat ggagtgttta cgacttccag taacattttc   1320
aagggatcag ccgtgtgtat gtatagcatg agtgatgtga aagggtgtt ccttggtcca    1380
tatgcccaca gggatggacc caactatcaa tgggtgcctt atcaaggaag agtccccctat 1440
ccacggccag gaacttgtcc cagcaaaaca tttggtggtt ttgactctac aaaggacctt   1500
cctgatgatg ttataacctt tgcaagaagt catccagcca tgtacaatcc agtgtttcct   1560
atgaacaatc gcccaatagt gatcaaaacg gatgtaaatt atcaatttac acaaattgtc   1620
gtagaccgag tggatgcaga agatggacag tatgatgtta tgtttatcgg aacagatgtt   1680
gggaccgttc ttaaagtagt ttcaattcct aaggagactt ggtatgattt agaagaggtt   1740
ctgctggaag aaatgacagt ttttcgggaa ccgactgcta tttcagcaat ggagctttcc   1800
actaagcagc aacaactata tattggttca acggctgggg ttgcccagct ccctttacac   1860
cggtgtgata tttacgggaa agcgtgtgct gagtgttgcc tcgcccgaga cccttactgt   1920
gcttgggatg ttctgcatg ttctcgctat ttccccactg caagagacg cacaagacga    1980
caagatataa gaatggaga cccactgact cactgttcag acttacacca tgataatcac   2040
```

```
catggccaca gccctgaaga gagaatcatc tatggtgtag agaatagtag cacattttg    2100
gaatgcagtc cgaagtcgca gagagcgctg gtctattggc aattccagag gcgaaatgaa   2160
gagcgaaaag aagagatcag agtggatgat catatcatca ggacagatca aggccttctg   2220
ctacgtagtc tacaacagaa ggattcaggc aattacctct gccatgcggt ggaacatggg   2280
ttcatacaaa ctcttcttaa ggtaaccctg gaagtcattg acacagagca tttggaagaa   2340
cttcttcata aagatgatga tggagatggc tctaagacca agaaatgtc caatagcatg    2400
acacctagcc agaaggtctg gtacagagac ttcatgcagc tcatcaacca ccccaatctc   2460
aacacaatgg atgagttctg tgaacaagtt tggaaaaggg accgaaaaca acgtcggcaa   2520
aggccaggac ataccccagg gaacagtaac aaatggaagc acttacaaga aaataagaaa   2580
ggtagaaaca ggaggaccca cgaatttgag agggcaccca ggagtgtctg agctgcatta   2640
cctctagaaa cctcaaacaa gtagaaactt gcctagacaa taactggaaa aacaaatgca   2700
atatacatga acttttttca tggcattatg tggatgttta caatggtggg aaattcagct   2760
gagttccacc aattataaat taaatccatg agtaactttc ctaataggct ttttttccta   2820
ataccaccac ctaacagaga acacaggtga atgcagatgt tcactttagc agacttaatg   2880
tttcctatga gatttcactg tacaggtttg tctttcttct ttgcctgaga aataaaaatg   2940
tcatttgcca tattgccatc taaaggagaa aaactgcatc agcaaagcca ttgtattgaa   3000
ctaaagttt aaaatgaact gcatggattt actaagctga tgaatattcc aaaacgtggt    3060
tggattcaag gatatatttt gtctaccggc cctcatgttt gtatgtactt gaggagtaaa   3120
atgagtaaaa tgatactgaa tgaaatgttc tgtggaaata ttaaaaaaaa aaaaaaacat   3180
aagccatcca tcatccagaa gaaaaatgga atacactgat ctactactga tgtcttcttt   3240
cagctttgat ctaaagatgt attttattaa aactataatt taaatgtacc atgaaaaata   3300
tgcagtaaaa attagttgtt ttctaagcta gagtaggatt tgtcttacaa ttattgtgct   3360
atgtagtttt tgttttaaaa attccaatgg tgtgctgctt tctttggaca ttttattttc   3420
aattctataa gagggataga tgacattgtt ctagaaacac atatacatca ttaagagtga   3480
atctctaaaa ccaggatata aattatgctt tatttctctg agaaaatcaa acaaatggaa   3540
gctgttcaca cctcccccttc tttaagcatt atctaaatta attttttactt gcataatgtt   3600
cttagaaaaa aaaacagaac atttaagcag gaaaaaagga agaaacaagt tgatttttaa   3660
gtgcattta ctataatgaa tcaatgaagg gaaaaggaac tgcatatttc atgaaaataa    3720
taagcattgt cttaatatac tgttaataga aaatgtgtct taattccgtg cttgaatccc   3780
tgcatgatat ttgagactaa gatctctctt atgattctac caagaattat atctgtgtca   3840
cttaattttt ttaaaagaga gagatcaata actattcaga gcaacatgtt aaaggcaaag   3900
tttccaatca tttacatctg tatcaggtgc ctcttacctt tccttattta agacaattat   3960
ttgtacaaga aacacatgac tcttttcata tcaatgggag ggactttct acaaagtatt     4020
ttccaggatg caacccacat ttaaacaatg taaaattctt tgtttcctgc aacaacttac   4080
aaaataaggt aaaagactaa aattcaagat ttgcttcctt cattgtccta agacgattcg   4140
ttgagaatca ctgactttga gatatttaaa actttcagca ttatactgtg gtttcttttg   4200
cactgcactc acctattcag gactcctccc ccaggttcct catcatgcac aaaaatgcaa   4260
agaaaacatc ttattagtaa ttaatgaagc aacattgaaa ttctaactct agctgtcttt   4320
ggattctaat taactcagca tcaatttctc acctcagact acagtgaatt tttatttcct   4380
atcagctgaa atatttcaca gatggaagct catgtttcag ttttaatgac tgccttgaat   4440
```

```
aaacaagttg ttgccacttg tttcaaacaa aagcctaaaa ataatctaca ttcaatttta    4500
ggctccattg actaatatgg tgttgctttt ggaagtactg tatatcctca catggaagcc    4560
aaattgttaa attatttgaa ggacacacca ctgtacagaa agtagtgttt caaatataaa    4620
tcgaagaaca aagagtgctc caaaaaatag gtcattcttt tattttcata aagtatctaa    4680
actgtactaa cattcagtgt tgtgtttcat tctaaatttg cagctgaaat aaatttattt    4740
gcgatagcag aaatatctta ttattcatcc tcagaaataa aggatttgaa gggatagaga    4800
ttatatgata aatttataga agactttcag aatttgaatg cattttgttt agtgttatga    4860
aatgacaata gaaaaagtc tcgacttcaa ttaaaagtta cacaaacaaa caaatctaca    4920
ggcatgtctt tatataccat caggtctaag ttttcaaaga aaattgtaga tataacttgc    4980
agataactca ttacagtcat aatctctgcc catgtgtatt gagaggggc agtttgcacg    5040 aaaaagaatt attggcccat ttaataattc agctttaaat agactttgtc atatgcatga    5100
atcatcagag atgaaactgt ttgagagact catgtgacct tacgaaaatt acaacagcag    5160
tcttaaagta tgaaaaagat gcatcacagc agagacatta tggcccagtt gatatcaaat    5220
gtaaaatgta aatgcatgta aatgcacact tcattttatg tattatttag taatttgcag    5280
tggtatgtgt ttaatatttt tgctacctac acattaggca aaaaaaagat gtaaataatt    5340
tgggagaaaa agaggaagaa cagtgtaaaa taaaactttc tataagtact ccatttcaat    5400
gtgttcaaca tcatcctaaa aggcaagatt ttcccacgca ggtgacaagg tggtttatgt    5460
actatttaag ggcggaaggt gcgtgcccgt tcaataagca tgttttttgc caggtaggaa    5520
atatgttcca tatctttact tatcattgca tttcagatgg gaactagaaa aactggagag    5580
aaaaatgtaa tgaaactgct gctgtaaatt attccttta gcatgtattc acttgctaaa    5640
tacacatttc ttcaaaataa aaaaaaaaaa aa                                 5672
```

<210> SEQ ID NO 19
<211> LENGTH: 5189
<212> TYPE: DNA
<213> ORGANISM: Homo sapiens

<400> SEQUENCE: 19

```
ggactgcgaa aggagcaggg ttgcggagct agggctccag cctgcggccg cgcattcttg     60
cgtctggcca gccgcgagct ctaagggtcg gccccgcccg gtccgccccc gcggctccct    120
gccaggctct cgcgggcgcg ctcggggtgg ggcctcgcgg ctggcggaga tgcggccggg    180
gctgcgcggt ggtgatgcga gcctgctggg cggcgcgccg gggcagccgg agccgcgcgc    240
cgcggcgctg taatcggaca ccaagagcgc tcgcccccgg cctccggcca ctttccattc    300
actccgaggt gcttgattga gcgacgcgga gaagagctcc gggtgccgcg gcactgcagc    360
gctgagattc ctttacaaag aaactcagag gaccgggaag aaagaatttc acctttgcga    420
cgtgctagaa aataaggtcg tctgggaaaa ggactggaga cacaagcgca tccaaccccg    480
gtagcaaact gatgactttt ccgtgctgat ttcttcaac ctcggtattt tcccttggat    540
attaacttgc atatctgaag aaatggcatt ccggacaatt tgcgtgttgg ttggagtatt    600
tatttgttct atctgtgtga aaggatcttc ccagccccaa gcaagagttt atttaacatt    660
tgatgaactt cgagaaacca agacctctga atacttcagc cttccccacc atcctttaga    720
ctacaggatt ttattaatgg atgaagatca ggaccggata tatgtgggaa gcaaagatca    780
cattctttcc ctgaatatta acaatataag tcaagaagct ttgagtgttt tctggccagc    840
```

```
atctacaatc aaagttgaag aatgcaaaat ggctggcaaa gatcccacac acggctgtgg    900
gaactttgtc cgtgtaattc agactttcaa tcgcacacat ttgtatgtct gtgggagtgg    960
cgctttcagt cctgtctgta cttacttgaa cagagggagg agatcagagg accaagtttt   1020
catgattgac tccaagtgtg aatctggaaa aggacgctgc tctttcaacc ccaacgtgaa   1080
cacggtgtct gttatgatca atgaggagct tttctctgga atgtatatag atttcatggg   1140
gacagatgct gctattttc gaagtttaac caagaggaat gcggtcagaa ctgatcaaca    1200
taattccaaa tggctaagtg aacctatgtt tgtagatgca catgtcatcc cagatggtac   1260
tgatccaaat gatgctaagg tgtacttctt cttcaaagaa aaactgactg acaataacag   1320
gagcacgaaa cagattcatt ccatgattgc tcgaatatgt cctaatgaca ctggtggact   1380
gcgtagcctt gtcaacaagt ggaccacttt cttaaaggcg aggctggtgt gctcggtaac   1440
agatgaagac ggcccagaaa cacactttga tgaattagag gatgtgtttc tgctggaaac   1500
tgataacccg aggacaacac tagtgtatgg catttttaca acatcaagct cagttttcaa   1560
aggatcagcc gtgtgtgtgt atcatttatc tgatatacag actgtgttta atgggccttt   1620
tgcccacaaa gaagggccca atcatcagct gatttcctat cagggcagaa ttccatatcc   1680
tcgccctgga acttgtccag gaggagcatt tacacccaat atgcgaacca ccaaggagtt   1740
cccagatgat gttgtcactt ttattcggaa ccatcctctc atgtacaatt ccatctaccc   1800
aatccacaaa aggccttga ttgttcgtat tggcactgac tacaagtata caagatagc    1860 tgtggatcga gtgaacgctg ctgatgggag ataccatgtc ctgtttctcg aacagatcg   1920 gggtactgtg caaaaagtgg ttgttcttcc tactaacaac tctgtcagtg gcgagctcat   1980
tctggaggag ctggaagtct ttaagaatca tgctcctata acaacaatga aaatttcatc   2040
taaaaagcaa cagttgtatg tgagttccaa tgaaggggtt tcccaggtat ctctgcaccg   2100
ctgccacatc tatggtacag cctgtgctga ctgctgcctg gcgcgggacc cttattgcgc   2160
ctgggatggc cattcctgtt ccagattcta cccaactggg aaacggagga gccgaagaca   2220
agatgtgaga catggaaacc cactgactca atgcagagga tttaatctaa aagcatacag   2280
aaatgcagct gaaattgtgc agtatggagt aaaaaataac accacttttc tggagtgtgc   2340
ccccaagtct ccgcaggcat ctatcaagtg gctgttacag aaagacaaag acaggaggaa   2400
agaggttaag ctgaatgaac gaataatagc cacttcacag ggactcctga tccgctctgt   2460
tcagggttct gaccaaggac tttatcactg cattgctaca gaaaatagtt tcaagcagac   2520
catagccaag atcaacttca agtttttaga ttcagaaatg gtggctgttg tgacggacaa   2580
atggtcccca tggacctggg ccagctctgt gagggcttta cccttccacc cgaaggacat   2640
catgggggca ttcagccact cagaaatgca atgattaac caatattgca aagacactcg    2700
gcagcaacat cagcagggag atgaatcaca gaaaatgaga ggggactatg gcaagttaaa   2760
ggccctcatc aatagtcgga aaagtagaaa caggaggaat cagttgccag agtcataata   2820
ttttcttatg tgggtcttat gcttccatta acaaatgctc tgtcttcaat gatcaaattt   2880
tgagcaaaga aacttgtgct ttaccaaggg gaattactga aaaggtgat tactcctgaa    2940 gtgagtttta cacgaactga aatgagcatg cattttcttg tatgatagtg actagcacta   3000
gacatgtcat ggtcctcatg gtgcatataa atatatttaa cttaacccag attttattta   3060
tatctttatt caccttttct tcaaaatcga tatggtggct gcaaaactag aattgttgca   3120
tccctcaatt gaatgagggc catatccctg tggtattcct ttcctgcttt ggggctttag   3180
aattctaatt gtcagtgatt ttgtatatga aaacaagttc caaatccaca gcttttacgt   3240
```

```
agtaaaagtc ataaatgcat atgacagaat ggctatcaaa agaaatgaaa aaggaagacg    3300
gcatttaaag ttgtataaaa acacgagtta ttcataaaga gaaaatgatg agtttttatg    3360
gttccaatga aatatgttgg ggttttttta agattgtaaa aataatcagt tactggtatc    3420
tgtcactgac ctttgtttcc ttattcagga agataaaaat cagtaaccta ccccatgaag    3480
atatttggtg ggagttatat cagtgaagca gtttggttta tattcttatg ttatcacctt    3540
ccaaacaaaa gcacttactt tttttggaag ttatttattt tagactcaaa gaatataatc    3600
ttgcactact cagttattac tgtttgttct cttattccct agtctgtgtg gcaaattaaa    3660
caatataaga aggaaaaatt tgaagtatta gacttctaaa taaggggtga aatcatcaga    3720
aagaaaaatc aaagtagaaa ctactaattt tttaagagga atttataaca aatatggcta    3780
gttttcaact tcagtactca aattcaatga ttcttccttt tattaaaacc agtctcagat    3840
atcatactga tttttaagtc aacactatat attttatgat cttttcagtg tgatggcaag    3900
gtgcttgtta tgtctagaaa gtaagaaaac aatatgagga gacattctgt ctttcaaaag    3960
gtaatggtac atacgttcac tggtctctaa gtgtaaaagt agtaaatttt gtgatgaata    4020
aaataattat ctcctaattg tatgttagaa taattttatt agaataattt catactgaaa    4080
ttattttctc caaataaaaa ttagatggaa aaatgtgaaa aaaattattc atgctctcat    4140
atatatttta aaaacactac ttttgctttt tatttaccct tttaagacat tttcatgctt    4200
ccaggtaaaa acagatattg taccatgtac ctaatccaaa tatcatataa acatttattt    4260
tatagttaat aatctatgat gaaggtaatt aaagtagatt atggccttt taagtattgc    4320
agtctaaaac ttcaaaaact aaaatcattg tcaaaattaa tatgattatt aatcagaata    4380
tcagaatatg attcactatt taaactatga taaattatga taatatatga ggaggcctcg    4440
ctatagcaaa aatagttaaa atgctgacat aacaccaaac ttcattttt aaaaaatctg    4500
ttgttccaaa tgtgtataat tttaaagtaa tttctaaagc agtttattat aatggtttgc    4560
ctgcttaaaa ggtataatta aacttctttt ctcttctaca ttgacacaca gaaatgtgtc    4620
aatgtaaagc caaaaccatc ttctgtgttt atggccaatc tattctcaaa gttaaaagta    4680
aaattgtttc agagtcacag ttccctttat ttcacataag cccaaactga tagacagtaa    4740
cggtgtttag ttttatacta tatttgtgct atttaattct ttctatttc acaattatta    4800
aattgtgtac actttcatta ctttaaaaa tgtagaaatt cttcatgaac ataactctgc    4860
tgaatgtaaa agaaaatttt ttttcaaaaa tgctgttaat gtatactact ggtggttgat    4920
tggttttatt ttatgtagct tgacaattca gtgacttaat atctattcca tttgtattgt    4980
acataaaatt ttctagaaat acactttttt ccaaagtgta agtttgtgaa tagattttag    5040
catgatgaaa ctgtcataat ggtgaatgtt caatctgtgt aagaaaacaa actaaatgta    5100
gttgtcacac taaaatttaa ttggatattg atgaaatcat tggcctggca aaataaaaca    5160
tgttgaattc cccaaaaaaa aaaaaaaaa                                    5189

<210> SEQ ID NO 20
<211> LENGTH: 3531
<212> TYPE: DNA
<213> ORGANISM: Homo sapiens

<400> SEQUENCE: 20
ccgcggcgcc gatcccggct gaggcgcagc ggcgagaggt cgcgggcagg gccatggccc      60 cgggggggccg ctagcgcgga ccggcccaac gggagccgct ccgtgccgcc gccgccgccc    120
```

```
gggcgcccag gccccgccgc tgcggaagag gtttctagag agtggagcct gcttcctggg      180
ccctaggccc ctcccacaat gcttgtcgcc ggtcttcttc tctgggcttc cctactgacc      240
ggggcctggc catccttccc cacccaggac cacctcccgg ccacgccccg ggtccggctc      300
tcattcaaag agctgaaggc cacaggcacc gcccacttct tcaacttcct gctcaacaca      360
accgactacc gaatcttgct caaggacgag gaccacgacc gcatgtacgt gggcagcaag      420
gactacgtgc tgtccctgga cctgcacgac atcaaccgcg agcccctcat tatacactgg      480
gcagcctccc cacagcgcat cgaggaatgc gtgctctcag gcaaggatgt caacggcgag      540
tgtgggaact tcgtcaggct catccagccc tggaaccgaa cacacctgta tgtgtgcggg      600
acaggtgcct acaaccccat gtgcacctat gtgaaccgcg gacgccgcgc ccaggccaca      660
ccatggaccc agactcaggc ggtcagaggc cgcggcagca gagccacgga tggtgccctc      720
cgcccgatgc ccacagcccc acgccaggat tacatcttct acctggagcc tgagcgactc      780
gagtcaggga agggcaagtg tccgtacgat cccaagctgg acacagcatc ggccctcatc      840
aatgaggagc tctatgctgg tgtgtacatc gattttatgg gcactgatgc agccatcttc      900
cgcacacttg gaaagcagac agccatgcgc acggatcagt acaactcccg gtggctgaac      960
gacccgtcgt tcatccatgc tgagctcatt cctgacagtg cggagcgcaa tgatgataag     1020
ctttacttct tcttccgtga gcggtcggca gaggcgccgc agagcccgc ggtgtacgcc     1080 cgcatcgggc gcatttgcct gaacgatgac ggtggtcact gttgcctggt caacaagtgg     1140
agcacattcc tgaaggcgcg gctcgtctgc tctgtcccgg gcgaggatgg cattgagact     1200
cactttgatg agctccagga cgtgtttgtc cagcagaccc aggacgtgag gaaccctgtc     1260
atttacgctg tctttacctc ctctggctcc gtgttccgag gctctgccgt gtgtgtctac     1320
tccatggctg atattcgcat ggtcttcaac gggccctttg cccacaaaga ggggcccaac     1380
taccagtgga tgcccttctc agggaagatg ccctaccca ggccgggcac gtgccctggt     1440
ggaaccttca cgccatctat gaagtccacc aaggattatc ctgatgaggt gatcaacttc     1500
atgcgcagcc acccactcat gtaccaggcc gtgtaccctc tgcagcggcg gcccctggta     1560
gtccgcacag gtgctcccta ccgccttacc actattgccg tggaccaggt ggatgcagcc     1620
gacgggcgct atgaggtgct tttcctgggc acagaccgcg ggacagtgca aaggtcatt     1680 gtgctgccca aggatgacca ggagttggag gagctcatgc tggaggaggt ggaggtcttc     1740
aaggatccag cacccgtcaa gaccatgacc atctcttcta agaggcaaca actctacgtg     1800
gcgtcagccg tgggtgtcac acacctgagc ctgcaccgct gccaggcgta tggggctgcc     1860
tgtgctgact gctgccttgc ccgggaccct tactgtgcct gggatggcca ggcctgctcc     1920
cgctatacag catcctccaa gaggcggagc cgccggcagg acgtccggca cggaaacccc     1980
atcaggcagt gccgtgggtt caactccaat gccaacaaga atgccgtgga gtctgtgcag     2040 tatgcgtgg ccggcagcgc agccttcctt gagtgccagc ccgctcgcc caagccact     2100 gttaagtggc tgttccagcg agatcctggt gaccggcgcc gagagattcg tgcagaggac     2160
cgcttcctgc gcacagagca gggcttgttg ctccgtgcac tgcagctcag cgatcgtggc     2220
ctctactcct gcacagccac tgagaacaac tttaagcacg tcgtcacacg agtgcagctg     2280
catgtactgg gccgggacgc cgtccatgct gccctcttcc caccactgtc catgagcgcc     2340
ccgccacccc caggcgcagg ccccccaacg cctccttacc aggagttagc ccagctgctg     2400
gcccagccaa aagtgggcct catccaccag tactgccagg ttactggcg ccatgtgccc     2460 cccagcccca gggaggctcc aggggcaccc cggtctcctg agccccagga ccagaaaaag     2520
```

```
cccccggaacc gccggcacca ccctccggac acatgaggcc agctgcctgt gcctgccatg    2580
ggccagccta gcccttgtcc cttttaatat aaaagatata tatatatata tatatatata    2640
aaatatctat attctataca caccctgccc ctgcaaagac agtatttatt ggtgggttga    2700
atatagcctg cctcagtggc agcatcctcc aaaacttaga cccatgctgg tcagagacgg    2760
cagaaaacag agcctgccta accaggccca gccagttggt ggggccaggc caggaccaca    2820
cagtccccag actcagctgg aagtctacct gctggacagc ctccgccaag atctacagga    2880
caaagggagg gagcaagccc tactcggatg gggcacggac tgtccacctt ttctgatgtg    2940
tgttgtcagc ctgtgctgtg gcatagacat ggatgcgagg accactttgg agactggggt    3000
ggcctcaaga gcacacagag aagggaagaa ggggccatca caggatgcca gcccctgcct    3060
gggttggggg cactcagcca cgaccagccc cttcctgggt atttattctc tatttattgg    3120
ggataggaga agaggcatcc tgcctggtg ggacagcctc ttcagcccct tctcccctcc    3180
ccgcctggcc agggcagggc caccccactc tacctcctta gctttccctg tgccactttg    3240
actcagaggc tgggagcata gcagaggggc caggcccagg cagagctgac gggaggcccc    3300
agctctgagg ggaggggtc cgtggtagag gcctggggcc ggtagaggct ccccagggct    3360
cccttatgtc caccacttca ggggatgggt gtggatgtaa ttagctctgg ggggcagttg    3420
ggtagatggg tggggctcc tggtggcctt ctgctgccca ggccacagcc gcctttgggt    3480
tccatcttgc taataaacac tggctctggg actagaaaaa aaaaaaaaaa a    3531

<210> SEQ ID NO 21
<211> LENGTH: 3879
<212> TYPE: DNA
<213> ORGANISM: Homo sapiens

<400> SEQUENCE: 21
atcagacgcg cagaggaggc ggggccgcgg ctggtttcct gccggggggc ggctctgggc      60
cgccgagtcc cctcctcccg cccctgagga ggaggagccg ccgccacccg ccgcgcccga     120
cacccgggag gccccgccag cccgcggag aggcccagcg ggagtcgcgg aacagcaggc     180
ccgagcccac cgcgccgggc cccggacgcc gcgcggaaaa gatgaattta caaccaattt     240
tctggattgg actgatcagt tcagtttgct gtgtgtttgc tcaaacagat gaaaatagat     300
gtttaaaagc aaatgccaaa tcatgtgag aatgtataca agcagggcca aattgtgggt     360
ggtgcacaaa ttcaacattt ttacaggaag gaatgcctac ttctgcacga tgtgatgatt     420
tagaagcctt aaaaaagaag ggttgccctc cagatgacat agaaaatccc agaggctcca     480
aagatataaa gaaaaataaa aatgtaacca accgtagcaa aggaacagca gagaagctca     540
agccagagga tattactcag atccaaccac agcagttggt tttgcgatta agatcagggg     600
agccacagac atttacatta aaattcaaga gagctgaaga ctatcccatt gacctctact     660 acctatgga cctgtcttac tcaatgaaag acgatttgga gaatgtaaaa agtcttggaa     720
cagatctgat gaatgaaatg aggaggatta cttcggactt cagaattgga tttggctcat     780
ttgtggaaaa gactgtgatg ccttacatta gcacaacacc agctaagctc aggaacccctt     840 gcacaagtga acagaactgc accagcccat ttagctacaa aaatgtgctc agtcttacta     900
ataaaggaga agtatttaat gaacttgttg aaaacagcg catatctgga aatttggatt     960
ctccagaagg tggtttcgat gccatcatgc aagttgcagt ttgtggatca ctgattggct    1020
ggaggaatgt tacacggctg ctggtgtttt ccacagatgc cggggtttcac tttgctggag    1080
```

```
atgggaaact tggtggcatt gttttaccaa atgatggaca atgtcacctg gaaaataata   1140
tgtacacaat gagccattat tatgattatc cttctattgc tcaccttgtc cagaaactga   1200
gtgaaaataa tattcagaca attttttgcag ttactgaaga atttcagcct gtttacaagg   1260
agctgaaaaa cttgatccct aagtcagcag taggaacatt atctgcaaat tctagcaatg   1320
taattcagtt gatcattgat gcatacaatt cccttttcctc agaagtcatt ttggaaaacg   1380
gcaaattgtc agaaggcgta acaataagtt acaaatctta ctgcaagaac ggggtgaatg   1440
gaacagggga aaatggaaga aaatgttcca atatttccat ggagatgag gttcaatttg    1500 aaattagcat aacttcaaat aagtgtccaa aaaggattc tgacagcttt aaaattaggc    1560
ctctgggctt tacggaggaa gtagaggtta ttcttcagta catctgtgaa tgtgaatgcc    1620
aaagcgaagg catccctgaa agtcccaagt gtcatgaagg aaatgggaca tttgagtgtg    1680
gcgcgtgcag gtgcaatgaa gggcgtgttg gtagacattg tgaatgcagc acagatgaag    1740
ttaacagtga agacatggat gcttactgca ggaaagaaaa cagttcagaa atctgcagta    1800
acaatggaga gtgcgtctgc ggacagtgtg tttgtaggaa gagggataat acaaatgaaa    1860
tttattctgg caaattctgc gagtgtgata atttcaactg tgatagatcc aatggcttaa    1920
tttgtggagg aaatggtgtt tgcaagtgtc gtgtgtgtga gtgcaaccccc aactacactg    1980 gcagtgcatg tgactgttct ttggatacta gtacttgtga agccagcaac ggacagatct    2040
gcaatggccg gggcatctgc gagtgtggtg tctgtaagtg tacagatccg aagtttcaag    2100
ggcaaacgtg tgagatgtgt cagacctgcc ttggtgtctg tgctgagcat aaagaatgtg    2160
ttcagtgcag agccttcaat aaaggagaaa agaaagacac atgcacacag gaatgttcct    2220
attttaacat taccaaggta gaaagtcggg acaaattacc ccagccggtc caacctgatc    2280
ctgtgtccca ttgtaaggag aaggatgttg acgactgttg gttctatttt acgtattcag    2340
tgaatgggaa caacgaggtc atggttcatg tgtgtggagaa tccagagtgt cccactggtc    2400
cagacatcat tccaattgta gctggtgtgg ttgctggaat tgttcttatt ggccttgcat    2460
tactgctgat atggaagctt ttaatgataa ttcatgacag aagggagttt gctaaatttg    2520
aaaaggagaa aatgaatgcc aaatgggaca cgggtgaaaa tcctatttat aagagtgccg    2580
taacaactgt ggtcaatccg aagtatgagg gaaaatgagt actgcccgtg caaatcccac    2640
aacactgaat gcaaagtagc aatttccata gtcacagtta ggtagcttta gggcaatatt    2700
gccatggttt tactcatgtg caggttttga aaatgtacaa tatgtataat ttttaaaatg    2760
ttttattatt ttgaaaataa tgttgtaatt catgccaggg actgacaaaa gacttgagac    2820
aggatggtta ctcttgtcag ctaaggtcac attgtgcctt tttgaccttt tcttcctgga    2880
ctattgaaat caagcttatt ggattaagtg atatttctat agcgattgaa agggcaatag    2940
ttaaagtaat gagcatgatg agagtttctg ttaatcatgt attaaaactg attttttagct   3000 ttacaaatat gtcagtttgc agttatgcag aatccaaagt aaatgtcctg ctagctagtt    3060
aaggattgtt ttaaatctgt tattttgcta tttgcctgtt agacatgact gatgacatat    3120
ctgaaagaca agtatgttga gagttgctgg tgtaaaatac gtttgaaata gttgatctac    3180
aaaggccatg ggaaaaattc agagagttag gaaggaaaaa ccaatagctt taaaacctgt    3240
gtgccatttt aagagttact taatgtttgg taactttttat gccttcactt tacaaattca    3300
agccttagat aaaagaaccg agcaattttc tgctaaaaag tccttgatttt agcactattt   3360 acatacaggc catactttac aaagtatttg ctgaatgggg accttttgag ttgaatttat    3420
tttattattt ttattttgtt taatgtctgg tgctttctgt cacctcttct aatctttaa     3480
```

-continued

| | |
|---|---|
| tgtatttgtt tgcaattttg gggtaagact ttttttatga gtacttttc tttgaagttt | 3540 |
| tagcggtcaa tttgccttttt taatgaacat gtgaagttat actgtggcta tgcaacagct | 3600 |
| ctcacctacg cgagtcttac tttgagttag tgccataaca gaccactgta tgtttacttc | 3660 |
| tcaccatttg agttgcccat cttgtttcac actagtcaca ttcttgtttt aagtgccttt | 3720 |
| agttttaaca gttcactttt tacagtgcta tttactgaag ttatttatta aatatgccta | 3780 |
| aaatacttaa atcggatgtc ttgactctga tgtatttat caggttgtgt gcatgaaatt | 3840 |
| tttatagatt aaagaagttg aggaaaagca aaaaaaaa | 3879 |

<210> SEQ ID NO 22
<211> LENGTH: 2217
<212> TYPE: DNA
<213> ORGANISM: Homo sapiens

<400> SEQUENCE: 22

| | |
|---|---|
| ccccgccgcc gccgcccttc gcgccctggg ccatctccct cccacctccc tccgcggagc | 60 |
| agccagacag cgagggcccc ggccggggc aggggggacg cccgtccgg ggcacccccc | 120 |
| cggctctgag ccgcccgcgg ggccggcctc ggcccggagc ggaggaagga gtcgccgagg | 180 |
| agcagcctga ggccccagag tctgagacga gccgccgccg ccccgccac tgcggggagg | 240 |
| aggggggagga ggagcgggag gagggacgag ctggtcggga gaagaggaaa aaaactttg | 300 |
| agacttttcc gttgccgctg ggagccggag gcgcggggac ctcttggcgc gacgctgccc | 360 |
| cgcgaggagg caggacttgg ggaccccaga ccgcctccct ttgccgccgg ggacgcttgc | 420 |
| tccctccctg cccctacac ggcgtccctc aggcgccccc attccggacc agccctcggg | 480 |
| agtcgccgac ccggcctccc gcaaagactt tccccagac ctcgggcgca ccccctgcac | 540 |
| gccgccttca tccccggcct gtctcctgag ccccgcgca tcctagaccc tttctcctcc | 600 |
| aggagacgga tctctctccg acctgccaca gatcccctat tcaagaccac ccaccttctg | 660 |
| gtaccagatc gcgcccatct aggttatttc cgtgggatac tgagacaccc ccggtccaag | 720 |
| cctcccctcc accactgcgc ccttctccct gaggacctca gctttccctc gaggccctcc | 780 |
| taccttttgc cgggagaccc ccagcccctg caggggcggg gcctcccac cacaccagcc | 840 |
| ctgttcgcgc tctcggcagt gccgggggc gccgcctccc ccatgccgcc ctccgggctg | 900 |
| cggctgctgc cgctgctgct accgctgctg tggctactgg tgctgacgcc tggccggccg | 960 |
| gccgcgggac tatccacctg caagactatc gacatggagc tggtgaagcg gaagcgcatc | 1020 |
| gaggccatcc gcgccagat cctgtccaag ctgcggctcg ccagcccccc gagccagggg | 1080 |
| gaggtgccgc ccggcccgct gcccgaggcc gtgctcgccc tgtacaacag cacccgcgac | 1140 |
| cgggtggccg gggagagtgc agaaccggag cccgagcctg aggccgacta ctacgccaag | 1200 |
| gaggtcaccc gcgtgctaat ggtggaaacc cacaacgaaa tctatgacaa gttcaagcag | 1260 |
| agtacacaca gcatatatat gttcttcaac acatcagagc tccgagaagc ggtacctgaa | 1320 |
| cccgtgttgc tctcccgggc agagctgcgt ctgctgaggc tcaagttaaa agtggagcag | 1380 |
| cacgtggagc tgtaccagaa atacagcaac aattcctggc gatacctcag caaccggctg | 1440 |
| ctggcaccca gcgactcgcc agagtggtta tcttttgatg tcaccggagt tgtgcggcag | 1500 |
| tggttgagcc gtggagggga aattgagggc tttcgcctta gcgcccactg ctcctgtgac | 1560 |
| agcagggata acacactgca gtggacatc aacgggttca ctaccggccg ccaggtgac | 1620 |
| ctggccacca ttcatggcat gaaccggcct ttcctgcttc tcatggccac cccgctggag | 1680 |

```
agggcccagc atctgcaaag ctcccggcac cgccgagccc tggacaccaa ctattgcttc    1740
agctccacgg agaagaactg ctgcgtgcgg cagctgtaca ttgacttccg caaggacctc    1800
ggctggaagt ggatccacga gcccaagggc taccatgcca acttctgcct cgggccctgc    1860
ccctacattt ggagcctgga cacgcagtac agcaaggtcc tggccctgta caaccagcat    1920
aacccgggcg cctcggcggc gccgtgctgc gtgccgcagg cgctggagcc gctgcccatc    1980
gtgtactacg tgggccgcaa gcccaaggtg agcagctgt ccaacatgat cgtgcgctcc    2040
tgcaagtgca gctgaggtcc cgccccgccc cgccccgccc cggcaggccc ggccccaccc    2100
cgccccgccc ccgctgcctt gcccatgggg gctgtattta aggacacccg tgccccaagc    2160
ccacctgggg ccccattaaa gatggagaga ggactgcgga aaaaaaaaa aaaaaaa       2217

<210> SEQ ID NO 23
<211> LENGTH: 6774
<212> TYPE: DNA
<213> ORGANISM: Homo sapiens

<400> SEQUENCE: 23
cggccccaga aacccgagc gagtagggggg cggcgcgcag gagggaggag aactgggggc      60
gcgggaggct ggtgggtgtg ggggtgtgag atgtagaaga tgtgacgccg cggcccggcg     120
ggtgccagat tagcggacgc ggtgcccgcg gttgcaacgg gatcccgggc gctgcagctt     180
gggaggcggc tctccccagg cggcgtccgc ggagacaccc atccgtgaac cccaggtccc     240
gggccgccgg ctcgccgcgc accaggggcc ggcggacaga gagcggccg agcggctcga     300 ggctggggga ccgcgggcgc ggccgcgcgc tgccgggcgg gaggctgggg ggccggggcc     360
ggggccgtgc cccggagcgg gtcggaggcc ggggccgggg ccggggacg gcggctcccc     420 gcgcggctcc agcggctcgg ggatcccggc cgggccccgc agggaccatg gcagccggga     480
gcatcaccac gctgcccgcc ttgcccgagg atggcggcag cggcgccttc ccgcccggcc     540
acttcaagga ccccaagcgg ctgtactgca aaaacggggg cttcttcctg cgcatccacc     600
ccgacggccg agttgacggg gtccgggaga agagcgaccc tcacatcaag ctacaacttc     660
aagcagaaga gagaggagtt gtgtctatca aaggagtgtg tgctaaccgt tacctggcta     720
tgaaggaaga tggaagatta ctggcttcta aatgtgttac ggatgagtgt ttcttttttg     780
aacgattgga atctaataac tacaatactt accggtcaag gaaatacacc agttggtatg     840
tggcactgaa acgaactggg cagtataaac ttggatccaa aacaggacct gggcagaaag     900
ctatactttt tcttccaatg tctgctaaga gctgatttta atggccacat ctaatctcat     960
ttcacatgaa agaagaagta tattttagaa atttgttaat gagagtaaaa gaaaataaat    1020
gtgtatagct cagtttggat aattggtcaa acaatttttt atccagtagt aaaatatgta    1080
accattgtcc cagtaaagaa aaataacaaa agttgtaaaa tgtatattct ccctttata    1140 ttgcatctgc tgttacccag tgaagcttac ctagagcaat gatctttttc acgcatttgc    1200
tttattcgaa aagaggcttt taaaatgtgc atgtttagaa acaaaatttc ttcatggaaa    1260
tcatatacat tagaaaatca cagtcagatg tttaatcaat ccaaaatgtc cactatttct    1320
tatgtcattc gttagtctac atgtttctaa acatataaat gtgaatttaa tcaattcctt    1380
tcatagtttt ataattctct ggcagttcct tatgatagag tttataaaac agtcctgtgt    1440
aaactgctgg aagttcttcc acagtcaggt caattttgtc aaaccttct ctgtacccat    1500 acagcagcag cctagcaact ctgctggtga tgggagttgt attttcagtc ttcgccaggt    1560
cattgagatc catccactca catcttaagc attcttcctg gcaaaaattt atggtgaatg    1620
```

```
aatatggctt taggcggcag atgatataca tatctgactt cccaaaagct ccaggatttg   1680
tgtgctgttg ccgaatactc aggacggacc tgaattctga ttttatacca gtctcttcaa   1740
aaacttctcg aaccgctgtg tctcctacgt aaaaaaagag atgtacaaat caataataat   1800
tacactttta gaaactgtat catcaaagat tttcagttaa agtagcatta tgtaaaggct   1860
caaaacatta ccctaacaaa gtaaagtttt caatacaaat tctttgcctt gtggatatca   1920
agaaatccca aaatattttc ttaccactgt aaattcaaga agcttttgaa atgctgaata   1980
tttctttggc tgctacttgg aggcttatct acctgtacat ttttggggtc agctcttttt   2040
aacttcttgc tgctctttt cccaaaaggt aaaaatatag attgaaaagt taaaacattt   2100
tgcatggctg cagttccttt gtttcttgag ataagattcc aaagaactta gattcatttc   2160
ttcaacaccg aaatgctgga ggtgtttgat cagttttcaa gaaacttgga atataaataa   2220
ttttataatt caacaaaggt tttcacattt tataaggttg attttccaat taaatgcaaa   2280
tttgtgtggc aggattttta ttgccattaa catatttttg tggctgcttt ttctacacat   2340
ccagatggtc cctctaactg ggctttctct aattttgtga tgttctgtca ttgtctccca   2400
aagtatttag gagaagccct ttaaaaagct gccttcctct accactttgc tggaaagctt   2460
cacaattgtc acagacaaag attttttgttc caatactcgt tttgcctcta tttttcttgt   2520
ttgtcaaata gtaaatgata tttgcccttg cagtaattct actggtgaaa acatgcaaa   2580 gaagaggaag tcacagaaac atgtctcaat tcccatgtgc tgtgactgta gactgtctta   2640
ccatagactc tcttacccat cccctggata tgctcttgtt ttttccctct aatagctatg   2700
gaaagatgca tagaaagagt ataatgtttt aaaacataag gcattcgtct gccatttttc   2760
aattacatgc tgacttccct tacaattgag atttgcccat aggttaaaca tggttagaaa   2820
caactgaaag cataaaagaa aaatctaggc cgggtgcagt ggctcatgcc tatattccct   2880
gcactttggg aggccaaagc aggaggatcg cttgagccca ggagttcaag accaacctgg   2940
tgaaaccccg tctctacaaa aaaacacaaa aaatagccag gcatggtggc gtgtacatgt   3000
ggtctcagat acttgggagg ctgaggtggg agggttgatc acttgaggct gagaggtcaa   3060
ggttgcagtg agccataatc gtgccactgc agtccagcct aggcaacaga gtgagacttt   3120
gtctcaaaaa aagagaaatt ttccttaata agaaaagtaa ttttactct gatgtgcaat   3180 acatttgtta ttaaatttat tatttaagat ggtagcacta gtcttaaatt gtataaaata   3240 tccccctaaca tgtttaaatg tccatttta ttcattatgc tttgaaaaat aattatgggg   3300
aaatacatgt ttgttattaa atttattatt aagatagta gcactagtct taaatttgat   3360
ataacatctc ctaacttgtt taaatgtcca ttttattct ttatgtttga aaataaatta   3420
tggggatcct atttagctct tagtaccact aatcaaaagt tcggcatgta gctcatgatc   3480
tatgctgttt ctatgtcgtg gaagcaccgg atgggggtag tgagcaaatc tgccctgctc   3540
agcagtcacc atagcagctg actgaaaatc agcactgcct gagtagtttt gatcagttta   3600
acttgaatca ctaactgact gaaaattgaa tgggcaaata agtgcttttg tctccagagt   3660
atgcgggaga cccttccacc tcaagatgga tatttcttcc ccaaggattt caagatgaat   3720
tgaatttttt aatcaagata gtgtgcttta ttctgttgta tttttatta ttttaatata   3780 ctgtaagcca aactgaaata acatttgctg ttttataggt tgaagaacaa taggaaaaac   3840
taagaggttt tgtttttatt tttgctgatg aagagatatg tttaaatatg ttgtattgtt   3900
ttgtttagtt acaggacaat aatgaaatgg agtttatatt tgttatttct attttgttat   3960
```

```
atttaataat agaattagat tgaaataaaa tataatggga aataatctgc agaatgtggg    4020
ttttcctggt gtttccctct gactctagtg cactgatgat ctctgataag gctcagctgc    4080
tttatagttc tctggctaat gcagcagata ctcttcctgc cagtggtaat acgattttt    4140
aagaaggcag tttgtcaatt ttaatcttgt ggatacctt atactcttag ggtattattt    4200
tatacaaaag ccttgaggat tgcattctat tttctatatg accctcttga tatttaaaaa    4260
acactatgga taacaattct tcatttacct agtattatga agaatgaag gagttcaaac     4320
aaatgtgttt cccagttaac tagggtttac tgtttgagcc aatataaatg tttaactgtt    4380
tgtgatggca gtattcctaa agtacattgc atgttttcct aaatacagag tttaaataat    4440
ttcagtaatt cttagatgat tcagcttcat cattaagaat atcttttgtt ttatgttgag    4500
ttagaaatgc cttcatatag acatagtctt tcagacctct actgtcagtt tcatttcta    4560
gctgctttca gggttttatg aattttcagg caaagcttta atttatacta agcttaggaa    4620
gtatggctaa tgccaacggc agttttttc ttcttaattc cacatgactg aggcatatat    4680
gatctctggg taggtgagtt gttgtgacaa ccacaagcac ttttttttt tttaaagaaa     4740
aaaaggtagt gaattttaa tcatctggac tttaagaagg attctggagt atacttaggc    4800
ctgaaattat atatatttgg cttggaaatg tgttttctt caattacatc tacaagtaag    4860
tacagctgaa attcagagga cccataagag ttcacatgaa aaaatcaat ttatttgaaa    4920
aggcaagatg caggagagag gaagccttgc aaacctgcag actgcttttt gcccaatata    4980
gattgggtaa ggctgcaaaa cataagctta attagctcac atgctctgct ctcacgtggc    5040
accagtggat agtgtgagag aattaggctg tagaacaaat ggccttctct ttcagcattc    5100
acaccactac aaaatcatct tttatatcaa cagaagaata agcataaact aagcaaaagg    5160
tcaataagta cctgaaacca agattggcta gagatatatc ttaatgcaat ccattttctg    5220
atggattgtt acgagttggc tatataatgt atgtatggta ttttgatttg tgtaaaagtt    5280
ttaaaaatca agctttaagt acatggacat ttttaaataa aatatttaaa gacaatttag    5340
aaaattgcct taatatcatt gttggctaaa tagaataggg gacatgcata ttaaggaaaa    5400
ggtcatggag aaataatatt ggtatcaaac aaatacattg atttgtcatg atacacattg    5460
aatttgatcc aatagtttaa ggaataggta ggaaaatttg gtttctattt ttcgatttcc    5520
tgtaaatcag tgacataaat aattcttagc ttattttata tttccttgtc ttaaatactg    5580
agctcagtaa gttgtgttag gggattattt ctcagttgag actttcttat atgacatttt    5640
actatgtttt gacttcctga ctattaaaaa taaatagtag atacaatttt cataaagtga    5700
agaattatat aatcactgct ttataactga ctttattata tttatttcaa agttcattta    5760
aaggctacta ttcatcctct gtgatggaat ggtcaggaat ttgttttctc atagtttaat    5820
tccaacaaca atattagtcg tatccaaaat aacctttaat gctaaacttt actgatgtat    5880
atccaaagct tctcattttc agacagatta atccagaagc agtcataaac agaagaatag    5940
gtggtatgtt cctaatgata ttatttctac taatggaata aactgtaata ttagaaatta    6000
tgctgctaat tatatcagct ctgaggtaat ttctgaaatg ttcagactca gtcggaacaa    6060
attggaaaat ttaaattttt attcttagct ataaagcaag aaagtaaaca cattaatttc    6120
ctcaacattt ttaagccaat taaaaatata aagatacac accaatatct tcttcaggct     6180
ctgacaggcc tcctggaaac ttccacatat tttcaactg cagtataaag tcagaaaata    6240
aagttaacat aactttcact aacacacaca tatgtagatt tcacaaaatc cacctataat    6300
tggtcaaagt ggttgagaat atattttta gtaattgcat gcaaaatttt tctagcttcc    6360
```

```
atcctttctc cctcgtttct tcttttttg ggggagctgg taactgatga aatcttttcc      6420 cacctttct cttcaggaaa tataagtggt tttgtttggt taacgtgata cattctgtat      6480
gaatgaaaca ttggagggaa acatctactg aatttctgta atttaaaata ttttgctgct     6540
agttaactat gaacagatag aagaatctta cagatgctgc tataaataag tagaaaatat    6600
aaatttcatc actaaaatat gctattttaa aatctatttc ctatattgta tttctaatca    6660
gatgtattac tcttattatt tctattgtat gtgttaatga ttttatgtaa aaatgtaatt    6720
gcttttcatg agtagtatga ataaaattga ttagtttgtg ttttcttgtc tccc          6774

<210> SEQ ID NO 24
<211> LENGTH: 1220
<212> TYPE: DNA
<213> ORGANISM: Homo sapiens

<400> SEQUENCE: 24
gggagcgggc gagtaggagg gggcgccggg ctatatatat agcggctcgg cctcgggcgg      60
gcctggcgct cagggaggcg cgcactgctc ctcagagtcc cagctccagc cgcgcgcttt     120
ccgcccggct cgccgctcca tgcagccggg gtagagcccg gcgcccgggg gccccgtcgc    180
ttgcctcccg cacctcctcg gttgcgcact cctgcccgag gtcggccgtg cgctcccgcg     240
ggacgccaca ggcgcagctc tgcccccag cttcccgggc gcactgaccg cctgaccgac     300
gcacggccct cgggccggga tgtcggggcc cgggacggcc gcggtagcgc tgctcccggc     360
ggtcctgctg gccttgctgg cgccctgggc gggccgaggg ggcgccgccg cacccactgc    420
acccaacggc acgctggagg ccgagctgga gcgccgctgg gagagcctgg tggcgctctc    480
gttggcgcgc ctgccggtgg cagcgcagcc caaggaggcg gccgtccaga gcggcgccgg     540
cgactacctg ctgggcatca gcggctgcg gcggctctac tgcaacgtgg gcatcggctt     600
ccacctccag gcgctccccg acggccgcat cggcggcgcg cacgcggaca cccgcgacag    660
cctgctggag ctctcgcccg tggagcgggg cgtggtgagc atcttcggcg tggccagccg    720
gttcttcgtg gccatgagca gcaagggcaa gctctatggc tcgcccttct tcaccgatga   780
gtgcacgttc aaggagattc tccttcccaa caactacaac gcctacgagt cctacaagta    840
ccccggcatg ttcatcgccc tgagcaagaa tgggaagacc aagaagggga accgagtgtc     900
gcccaccatg aaggtcaccc acttcctccc caggctgtga ccctccagag gacccttgcc    960
tcagcctcgg gaagccctg ggagggcagt gccgagggtc accttggtgc actttcttcg   1020
gatgaagagt ttaatgcaag agtaggtgta agatatttaa attaattatt taaatgtgta   1080
tatattgcca ccaaattatt tatagttctg cgggtgtgtt ttttaattt ctgggggggaa   1140 aaaaagacaa aacaaaaaac caactctgac tttctggtg caacagtgga gaatcttacc   1200
attggatttc tttaacttgt                                                 1220

<210> SEQ ID NO 25
<211> LENGTH: 2820
<212> TYPE: DNA
<213> ORGANISM: Homo sapiens

<400> SEQUENCE: 25
gggagttcag acctagatct ttccagttaa tcacacaaca aacttagctc atcgcaataa      60
aaagcagctc agagccgact ggctctttta ggcactgact ccgaacagga ttctttcacc    120
caggcatctc ctccagaggg atccgccagc ccgtccagca gcaccatgtg ggtgaccaaa    180
```

```
ctcctgccag ccctgctgct gcagcatgtc ctcctgcatc tcctcctgct ccccatcgcc    240
atcccctatg cagagggaca aaggaaaaga agaaatacaa ttcatgaatt caaaaaatca    300
gcaaagacta ccctaatcaa aatagatcca gcactgaaga taaaaaccaa aaaagtgaat    360
actgcagacc aatgtgctaa tagatgtact aggaataaag gacttccatt cacttgcaag    420
gcttttgttt ttgataaagc aagaaaacaa tgcctctggt tccccttcaa tagcatgtca    480
agtggagtga aaaagaatt tggccatgaa tttgacctct atgaaaacaa agactacatt    540
agaaactgca tcattggtaa aggacgcagc tacaagggaa cagtatctat cactaagagt    600
ggcatcaaat gtcagccctg gagttccatg ataccacacg aacacagctt tttgccttcg    660
agctatcggg gtaaagacct acaggaaaac tactgtcgaa atcctcgagg ggaagaaggg    720
ggaccctggt gtttcacaag caatccagag gtacgctacg aagtctgtga cattcctcag    780
tgttcagaag ttgaatgcat gacctgcaat ggggagagtt atcgaggtct catggatcat    840
acagaatcag gcaagatttg tcagcgctgg gatcatcaga caccacaccg gcacaaattc    900
ttgcctgaaa gatatcccga caagggcttt gatgataatt attgccgcaa tcccgatggc    960
cagccgaggc catggtgcta tactcttgac cctcacaccc gctgggagta ctgtgcaatt   1020
aaaacatgcg ctgacaatac tatgaatgac actgatgttc ctttggaaac aactgaatgc   1080
atccaaggtc aaggagaagg ctacaggggc actgtcaata ccatttggaa tggaattcca   1140
tgtcagcgtt gggattctca gtatcctcac gagcatgaca tgactcctga aaatttcaag   1200
tgcaaggacc tacgagaaaa ttactgccga aatccagatg gtctgaatc accctggtgt   1260
tttaccactg atccaaacat ccgagttggc tactgctccc aaattccaaa ctgtgatatg   1320
tcacatggac aagattgtta tcgtgggaat ggcaaaaatt atatgggcaa cttatcccaa   1380
acaagatctg gactaacatg ttcaatgtgg gacaagaaca tggaagactt acatcgtcat   1440
atcttctggg aaccagatgc aagtaagctg aatgagaatt actgccgaaa tccagatgat   1500
gatgctcatg gaccctggtg ctacacggga aatccactca ttccttggga ttattgccct   1560
atttctcgtt gtgaaggtga taccacacct acaatagtca atttagacca tccgtaata   1620
tcttgtgcca aaacgaaaca attgcgagtt gtaaatggga ttccaacacg aacaaacata   1680
ggatggatgg ttagtttgag atacagaaat aaacatatct gcggaggatc attgataaag   1740
gagagttggg ttcttactgc acgacagtgt ttcccttctc gagacttgaa agattatgaa   1800
gcttggcttg gaattcatga tgtccacgga agaggagatg agaaatgcaa acaggttctc   1860
aatgtttccc agctggtata tggccctgaa ggatcagatc tggttttaat gaagcttgcc   1920
aggcctgctg tcctggatga ttttgttagt acgattgatt tacctaatta tggatgcaca   1980
attcctgaaa agaccagttg cagtgtttat ggctggggct acactggatt gatcaactat   2040
gatggcctat tacgagtggc acatctctat ataatgggaa atgagaaatg cagccagcat   2100
catcgaggga aggtgactct gaatgagtct gaaatatgtg ctggggctga aaagattgga   2160
tcaggaccat gtgaggggga ttatggtggc ccacttgttt gtgagcaaca taaaatgaga   2220
atggttcttg gtgtcattgt tcctggtcgt ggatgtgcca ttccaaatcg tcctggtatt   2280
tttgtccgag tagcatatta tgcaaaatgg atacacaaaa ttattttaac atataaggta   2340
ccacagtcat agctgaagta agtgtgtctg aagcacccac caatacaact gtcttttaca   2400
tgaagatttc agagaatgtg gaatttaaaa tgtcacttac aacaatccta agacaactac   2460
tggagagtca tgtttgttga aattctcatt aatgtttatg ggtgttttct gttgttttgt   2520
ttgtcagtgt tattttgtca atgttgaagt gaattaaggt acatgcaagt gtaataacat   2580
```

```
atctcctgaa gatacttgaa tggattaaaa aaacacacag gtatatttgc tggatgataa    2640
agatttcatg ggaaaaaaaa tcaattaatc tgtctaagct gctttctgat gttggtttct    2700
taataatgag taaaccacaa attaaatgtt attttaacct caccaaaaca atttatacct    2760
tgtgtcccta aattgtagcc ctatattaaa ttatattaca tttcaaaaaa aaaaaaaaaa    2820

<210> SEQ ID NO 26
<211> LENGTH: 487
<212> TYPE: DNA
<213> ORGANISM: Ovis aries

<400> SEQUENCE: 26
gcccttcaga cagctggtgc cgaagctcca ggaacatcct tctctcttca atcatggctt     60
gtcagggtct ggtcgccagc aacctgaatc tcaaacctgg ggagtgcctc agagtgcggg    120
gcgaggtggc cgcagacgcc aagagcttct cgctgaacct gggcaaagat gacaacaatc    180
tgtgcctgca cttcaaccct cgtttcgaag cgcatgggga catcaacacc atcgtgtgta    240
acagcaagga cgctggggcc tggggggccg agcagaggga atctgccttc cccttccagc    300
ctggaagtgt cgcggaggta tgcgtctcct tcaatgagac agacctaacc atcaagctgc    360
ctgatggata cgaattcaag ttccccaacc gcctcaacct ggaggccatc aactacctgg    420
ctgcaggtgg tgacttcaag atcaagtgtg tggcctttga gtgacatatg ggccagccag    480
caagggc                                                              487

<210> SEQ ID NO 27
<211> LENGTH: 5895
<212> TYPE: DNA
<213> ORGANISM: Homo sapiens

<400> SEQUENCE: 27
gcagttggtg aaactcctct gtctcccgct catcttttca ttgctcgttc ccctccttcc     60
cgcagacacc cggacctccc ctgggcgcca gctccgcggc tccaacgggt ccagaaacaa    120
gccggatttt ttttttttct tcctggaaat tggcttggt gtgtgttgcc ctacctccct    180 cctcccctc ccacccacag cccccccccg gccttttttt tttttttttt ttttttgag     240 acatggcccg ggcagtggct cctggaagag gaacaagtgt gggaaagggg agaggaagcc    300
ggagctaaat gacaggatgc aggcgacttg agacacaaaa agagaagcgt tcctctcgga    360
tccaggcatt gcctcgctgc tttctttttct ccaagacggg ctgaggattg tacagctcta    420
ggcggagttg gggctcttcg gatcgcttag attctcctct ttgctgcatt tccccccacg    480
tcctcgttct cccgcgtctg cctgcggacc cggagaaggg agaatggaga gggggctgcc    540
gctcctctgc gccgtgctcg ccctcgtcct cgccccggcc ggcgcttttc gcaacgataa    600
atgtggcgat actataaaaa ttgaaagccc cgggtacctt acatctcctg gttatcctca    660
ttcttatcac ccaagtgaaa aatgcgaatg gctgattcag gctccggacc cataccagag    720
aattatgatc aacttcaacc ctcacttcga tttggaggac agagactgca agtatgacta    780
cgtggaagtc ttcgatggag aaaatgaaaa tggacatttt agggaaagt tctgtggaaa    840 gatagccct cctcctgttg tgtcttcagg gccatttctt tttatcaaat ttgtctctga    900
ctacgaaaca catggtgcag gattttccat acgttatgaa attttcaaga gaggtcctga    960
atgttcccag aactacacaa cacctagtgg agtgataaag tccccccgat tcctgaaaa   1020 atatcccaac agccttgaat gcacttatat tgtctttgcg ccaaagatgt cagagattat   1080
```

```
cctggaattt gaaagctttg acctggagcc tgactcaaat cctccagggg ggatgttctg    1140
tcgctacgac cggctagaaa tctgggatgg attccctgat gttggccctc acattgggcg    1200
ttactgtgga cagaaaacac caggtcgaat ccgatcctca tcgggcattc tctccatggt    1260
tttttacacc gacagcgcga tagcaaaaga aggtttctca gcaaactaca gtgtcttgca    1320
gagcagtgtc tcagaagatt tcaaatgtat ggaagctctg gcatggaat caggagaaat     1380 tcattctgac cagatcacag cttcttccca gtatagcacc aactggtctg cagagcgctc    1440
ccgcctgaac taccctgaga tgggtggac tcccggagag gattcctacc gagagtggat     1500
acaggtagac ttgggccttc tgcgctttgt cacggctgtc gggacacagg cgccatttc    1560 aaaagaaacc aagaagaaat attatgtcaa gacttacaag atcgacgtta gctccaacgg    1620
ggaagactgg atcaccataa agaaggaaa caaacctgtt ctctttcagg aaacaccaa     1680 ccccacagat gttgtggttg cagtattccc caaaccactg ataactcgat tgtccgaat    1740 caagcctgca acttgggaaa ctggcatatc tatgagattt gaagtatacg gttgcaagat    1800
aacagattat ccttgctctg gaatgttggg tatggtgtct ggacttattt ctgactccca    1860
gatcacatca tccaaccaag gggacagaaa ctggatgcct gaaaacatcc gcctggtaac    1920
cagtcgctct ggctgggcac ttccacccgc acctcattcc tacatcaatg agtggctcca    1980
aatagacctg ggggaggaga agatcgtgag gggcatcatc attcagggtg ggaagcaccg    2040
agagaacaag gtgttcatga ggaagttcaa gatcgggtac agcaacaacg gctcggactg    2100
gaagatgatc atggatgaca gcaaacgcaa ggcgaagtct tttgagggca caacaacta    2160 tgatacacct gagctgcgga cttttccagc tctctccacg cgattcatca ggatctaccc    2220
cgagagagcc actcatggcg gactggggct cagaatggag ctgctgggct gtgaagtgga    2280
agcccctaca gctggaccga ccactcccaa cgggaacttg gtggatgaat gtgatgacga    2340
ccaggccaac tgccacagtg aacaggtga tgacttccag ctcacaggtg gcaccactgt    2400
gctggccaca gaaaagccca cggtcataga cagcaccata caatcagagt ttccaacata    2460
tggttttaac tgtgaatttg ctggggctc tcacaagacc ttctgccact gggaacatga    2520
caatcacgtg cagctcaagt ggagtgtgtt gaccagcaag acgggaccca ttcaggatca    2580
cacaggagat ggcaacttca tctattccca agctgacgaa aatcagaagg caaagtggc    2640 tcgcctggtg agccctgtgg tttattccca gaactctgcc cactgcatga ccttctggta    2700
tcacatgtct gggtcccacg tcggcacact cagggtcaaa ctgcgctacc agaagccaga    2760
ggagtacgat cagctggtct ggatggccat tggacaccaa ggtgaccact ggaaggaagg    2820
gcgtgtcttg ctccacaagt ctctgaaact ttatcaggtg attttcgagg gcgaaatcgg    2880
aaaaggaaac cttggtggga ttgctgtgga tgacattagt attaataacc acatttcaca    2940
agaagattgt gcaaaaccag cagacctgga taaaagaac ccagaaatta aaattgatga     3000
aacagggagc acgccaggat acgaaggtga aggagaaggt gacaagaaca tctccaggaa    3060
gccaggcaat gtgttgaaga ccttagaccc catcctcatc accatcatag ccatgagtgc    3120
cctgggggtc ctcctggggg ctgtctgtgg ggtcgtgctg tactgtgcct gttggcataa    3180
tgggatgtca gaaagaaact tgtctgccct ggagaactat aactttgaac ttgtggatgg    3240
tgtgaagttg aaaaaagaca aactgaatac acagagtact tattcggagg catgaaggca    3300
gacagagatg aaaagacagt caaaggacgg aagtggaagg acgggagtga gctgggagc    3360 tgttgatctt tcactataca ggctgggaag tgtgttgatg accactgagc caggcttttc    3420
tcaggagctt caatgagtat ggccgacaga catggacaag gagctgtgtt caccatcgga    3480
```

```
ctcatgtgca gtcagctttt ttcctgttgg tttcatttga ataatcagat gctggtgttg   3540
agaccaagta tgattgacat aatcattcat ttcgacccct cctgccctc tctctctctc    3600
tcctctcccc tttgtggatt cttttttggaa actgagcgaa atccaagatg ctggcaccaa  3660
gcgtattccg tgtggcctt tggatggaca tgctacctga aacccagtgc ccagaatata    3720
ctagaatcac cgcatttcag tggactcctg aagttgtact tgtgtataat tgcccgcgtc   3780
gtgcataggc aaagaaggat taggctgttt tcttttttaaa gtactgtagc ctcagtactg  3840
gtgtagtgtg tcagctctgt ttacgaagca atactgtcca gttttcttgc tgttttccg    3900
gtgttgtact aaacctcgtg cttgtgaact ccatacagaa aacggtgcca tccctgaaca   3960
cggctggcca ctgggtatac tgctgacaac cgcaacaaca aaaacacaaa tccttggcac   4020
tggctagtct atgtcctctc aagtgccttt ttgtttgtac tggttcattg tgttacatta  4080
acgacccact ctgcttcttg ctggtgaaag ccctgctctt taatcaaact ctggtggccc   4140
actgactaag aagaaagttt attttcgtgt gagatgccag cccctccggg caggcaaggg  4200
ctctgaagat ttggcaacgt ggcttaattg ttctgctttt tctgtagttc aatttcatgt   4260
ttcttgaccc ttttgtataa agctacaata ttctctctta ttgttctttc atatggaatg  4320
tattttcaaa tgtaaactct cttctctttc tctctcctat ctctctgtct tttttctctc   4380
ttagaattgg aggatttgcc attgtccagg aaagaaactt gcagctttaa cctgctggga  4440
atggcaaacg attttactag actttatgtt taaaaataaa taaataaggg aaattcctaa   4500
ctttgccctc caaagtctaa ctttggtttt cttgttaact ggttaaagtg acagtatctt   4560
ttttccttat ctattctatt caaaatgacc tttgatagaa atgttggcat ttagtagaaa  4620
tagtgataag ttgaggaaag aaataataca aattggcttt caagtgagac ccaaaggaag   4680
aactggataa aatcttccaa atccaaaagc atgagatttt tctatccaaa tatgcaaaaa   4740
tgacccaaga gaacttttctt attttgctac tgagtcacac aagggaagtg gaaggaagaa   4800
cagttaattt aagaatgaaa ctataaatcc tgatgcctgg gggtcaagta ttttaagata   4860
agaggggggaa aaacacataa agtcaaacaa atgttttaaa aattcataac agcaaccttg  4920
aaaaaataga cttaaatgaa tgcttctaga aacttccagc ggctcacaaa gaataagcct  4980
gccttagggc tggcaacatc taagcctcta acagcacagg gaagcaaata tcttaccagg   5040
cagcctatga attaacccaa agaagctttg gttggttttg gtggattttt atcatgccat   5100
gttggacatg agattttta gatcttcctt cccacattgc tagacgtctc actcaaagac   5160
atttgttggg agtcacattt gcatcataga cgagacagtc cattcatctt agttaaattg   5220
gattgagaat gccttttgtt tccaggaaaa tattgatcac catgaaagaa gaatagtttt  5280
ttgtccccag agacattcat ttagttgata taatcctacc agaaggaaag cactaagaaa  5340
cactcgtttg ttgttttaa aggcaacaga cttaaagttg tcctcagcca aggaaaaatg    5400
atactgcaac tttaaaattt aaagtatctt gcactgataa atatatttaa aaattatatg   5460
tttataaagt tattaatttg taaaggcagt gttacaaaat gttcagttta tattgtttta   5520
gattgttttg taattttttaa aggtgtaaaa taacatattt tttctttatg gaaatctata  5580
aaactttctg tagtaaaatg ttttcatttt actggtatat tattgcttca tgttttgtac   5640
catcataaga ttttgtgcag attttttta cagaaattat tattttctat gacaatatga    5700
cacttgtaaa ttgttgtttc aaaatgaaca gcgaagcctt aactttaaat gacatttgta   5760
ttctcagaca ctgagtagca taaaaaccac atagaactga actgtaactt aaattccaaa   5820
```
ctatgactac tacattccaa agaaacagtt gaattaaaca ttttcataaa atatcccaca    5880
aaaaaaaaaa aaaaa                                                    5895

<210> SEQ ID NO 28
<211> LENGTH: 6671
<212> TYPE: DNA
<213> ORGANISM: Homo sapiens

<400> SEQUENCE: 28
cagagatcgc gagcgaggca ccagcctgca gccggccccc agcacatcct cagccgcaca      60
gacactcggc gaggtggagg tgagggcggg cgccagcgaa ctcggagagg ggctcgctca     120
ctcccaggcg atcccagccg ccaccgccgc cgcaccagca gcagcaacag cagcagcagc     180
ttccttcctc agactcccct cgagaggctg ccaagcggg tgtagccgtt gggggaggct      240
cccgccgggg gaacccggcg aggacaagag cagggcggcc gccttccact cgggctgtcc     300
ggcggcggct gcctccgccc gtgtgtccgt caagggtgcc gcgggatgtg tgtcagttta     360
cgcctctgag atcacacagc tgcctggggg ccgtgtgatg cccaaggcaa gtcttggttt     420
taattattat tattatcatt attgttacgc ttggctttcg ggaaatactc gtgatatttg     480
taggataaag gaaatgacac tttgaggaac tggagagaac atatatgcgt tttgttttta     540
agaggaaaac cgtgttctct tcccggcttg ttccctcttt gctgatttca ggagctactc     600
tcctcctggt gaggtggaaa ttccagcaag aatagaggtg aagacaagcc accaggactc     660
aggagggaaa cgctgaccat tagaaacctc tgcataagac gttgtaagga ggaaaataaa     720
agagagaaaa acacaaagat ttaaacaaga aacctacgaa cccagctctg aaagagcca     780 ccttctccaa aatggatatg tttcctctca cctgggtttt cttagccctc tacttttcaa     840
gacaccaagt gagaggccaa ccagacccac cgtgcggagg tcgtttgaat tccaaagatg     900
ctggctatat cacctctccc ggttaccccc aggactaccc ctcccaccag aactgcgagt     960
ggattgttta cgcccccgaa cccaaccaga agattgtcct caacttcaac cctcactttg    1020
aaatcgagaa gcacgactgc aagtatgact ttatcgagat tcggatggg gacagtgaat     1080 ccgcagacct cctgggcaaa cactgtggga catcgcccc gccaccatc atctcctcgg      1140 gctccatgct ctacatcaag ttcacctccg actacgcccg gcaggggca ggcttctctc      1200 tgcgctacga gatcttcaag acaggctctg aagattgctc aaaaaacttc acaagcccca    1260 acggaccat cgaatctcct gggtttcctg agaagtatcc acacaacttg gactgcacct     1320
ttaccatcct ggccaaaccc aagatggaga tcatcctgca gttcctgatc tttgacctgg    1380
agcatgaccc tttgcaggtg ggagaggggg actgcaagta cgattggctg gacatctggg    1440
atggcattcc acatgttggc ccctgattg gcaagtactg tgggaccaaa acaccctctg     1500
aacttcgttc atcgacgggg atcctctccc tgaccttca cacggacatg gcggtggcca    1560
aggatggctt ctctgcgcgt tactacctgg tccaccaaga gccactagag aactttcagt    1620
gcaatgttcc tctgggcatg gagtctggcc ggattgctaa tgaacagatc agtgcctcat    1680
ctacctactc tgatgggagg tggaccccctc aacaaagccg gctccatggt gatgacaatg    1740
gctggacccc caacttggat tccaacaagg agtatctcca ggtggacctg cgctttttaa    1800
ccatgctcac ggccatcgca acacagggag cgatttccag ggaaacacag aatggctact    1860
atgtcaaatc ctacaagctg gaagtcagca ctaatggaga ggactggatg gtgtaccggc    1920
atggcaaaaa ccacaaggta tttcaagcca acaacgatgc aactgaggtg gttctgaaca    1980
agctccacgc tccactgctg acaaggtttg ttagaatccg ccctcagacc tggcactcag    2040

```
gtatcgccct ccggctggag ctcttcggct gccgggtcac agatgctccc tgctccaaca    2100
tgctggggat gctctcaggc ctcattgcag actcccagat ctccgcctct tccacccagg    2160
aatacctctg gagccccagt gcagcccgcc tggtcagcag ccgctcgggc tggttccctc    2220
gaatccctca ggcccagccc ggtgaggagt ggcttcaggt agatctggga acacccaaga    2280
cagtgaaagg tgtcatcatc cagggagccc gcggaggaga cagtatcact gctgtggaag    2340
ccagagcatt tgtgcgcaag ttcaaagtct cctacagcct aaacggcaag gactgggaat    2400
acattcagga ccccaggacc cagcagccaa agctgttcga agggaacatg cactatgaca    2460
cccctgacat ccgaaggttt gaccccattc cggcacagta tgtgcgggta tacccggaga    2520
ggtggtcgcc ggcggggatt gggatgcggc tggaggtgct gggctgtgac tggacagact    2580
ccaagcccac ggtagagacg ctgggaccca ctgtgaagag cgaagagaca accaccccct    2640
accccaccga agaggaggcc acagagtgtg gggagaactg cagctttgag gatgacaaag    2700
atttgcagct cccttcggga ttcaattgca acttcgattt cctcgaggag ccctgtggtt    2760
ggatgtatga ccatgccaag tggctccgga ccacctgggc cagcagctcc agcccaaacg    2820
accggacgtt tccagatgac aggaatttct tgcggctgca gagtgacagc cagagagagg    2880
gccagtatgc ccggctcatc agccccctg tccacctgcc ccgaagcccg tgtgcatgg    2940 agttccagta ccaggccacg ggcggccgcg ggtggcgct gcaggtggtg cgggaagcca    3000
gccaggagag caagttgctg tgggtcatcc gtgaggacca gggcggcgag tggaagcacg    3060
ggcggatcat cctgcccagc tacgacatgg agtaccagat tgtgttcgag ggagtgatag    3120
ggaaaggacg ttccggagag attgccattg atgacattcg ataagcact gatgtcccac    3180 tggagaactg catggaaccc atctcggctt ttgcaggtga aattttaaa gtggacatcc    3240 cagaaataca tgagagagaa ggatatgaag atgaaattga tgatgaatac gaggtggact    3300
ggagcaattc ttcttctgca acctcagggt ctggcgcccc ctcgaccgac aaagaaaaga    3360
gctggctgta caccctggat cccatcctca tcaccatcat cgccatgagc tcactgggcg    3420
tcctcctggg ggccacctgt gcaggcctcc tgctctactg cacctgttcc tactcgggcc    3480
tgagctcccg aagctgcacc acactggaga actacaactt cgagctctac gatggcctta    3540
agcacaaggt caagatgaac caccaaaagt gctgctccga ggcatgacgg attgcacctg    3600
aatcctatct gacgtttcat tccagcaaga ggggctgggg aagattacat tttttttcc    3660 tttggaaact gaatgccata atctcgatca aaccgatcca gaataccgaa ggtatggaca    3720
ggacagaaaa gcgagtcgca ggaggaaggg agatgcagcc gcacagggga tgattaccct    3780
cctaggaccg cggtggctaa gtcattgcag gaacgggct gtgttctctg ctgggacaaa    3840
acaggagctc atctctttgg ggtcacagtt ctattttgtt tgtgagtttg tattattatt    3900
attattatta ttattattat attttatttc tttggtctgt gagcaactca agaggcaga    3960 agaggagaat gacttttcca gaatagaagt ggagcagtga tcattattct ccgctttctc    4020
tttctaatca acacttgaaa agcaaagtgt cttttcagcc tttccatctt tacaaataaa    4080
actcaaaaaa gccgtccagc ttatcccatc ctctgattgt cttctgactt aagggattta    4140
ctgtggtgta ggttctgcca gccaacccta caagctgcca tttccagtcc tagcatttaa    4200
gtaggatgtt gttgcccttta acttttctta tccagggggaa aattgccatt ttagggtcag    4260
catgaacagc tctttcttgt atgcgattta aacaaactg gaaaggaaac ttcacacgtc    4320
aaaatccata gaagcgcctg gacgaggctt aaagtgcttt gtgagtgaat aggagccatt    4380
```

```
cgctaattct agacccacag tgtctggtgg tggggcttcc cttgtggggc ttctggtggt    4440
ggttttgcct tttcttttcc ctcctccatg ttcttctaaa acatatacat atatacatac    4500
acacatacac atattcttca ggtctctaag cccctggaag cagcattgtg tgatattctc    4560
agaggcaggg gaaatagag ggaaaaatag agactattgg tatgttctcc ccatcagcga     4620
gttattgtaa ctggtcacca ctggacggga aggagaacag aggagaggga aagagaagcc    4680
caacctctgt gatcatatga gggccaaggc tgagcagtgt agacagagac cctttgaaat    4740
gcatttgtct ctcaaataga ctagtaaaca ccgacttctc ctttgggtta caaacaccat    4800
ttcaaccttt cgggagagtc agagctagga tgtacaagaa ctgattctaa ccagaagtcc    4860
gcaagtactg tggacaagaa tgcttaacca tgctgcttca gccttgagag acctaggttc    4920
ttacacatat gcacacacgc atacacacat gcacgcacac acacatacac acatgcacgc    4980
acgcacgcat gcacaccaat ttatgttttt attaagtgcc ttgaaaaaat gaagaaaaat    5040
gtattttccc tttatgtaaa aattagtgaa tatcttatga attaaggcat tcctctttcc    5100
ctaaccccga tggctccatt cccaagtacc ccaactcact gctgatccta ttaaaggaat    5160
gagtcctgct acccgagtgg tagtcatagc cctagatgac tctcaactac tcttcaaagg    5220
gaggcatcag gaatagaatg aaactgtgtg aaggataaga ttgttcgcat caagatccaa    5280
atcttgattt catattaacg cctaaggatt gcctgtgtgc tggaaatata tttgaaactc    5340
aaccagtatg cccagcctat tgcatatcat tgtcagacca ttttgctgc tgtggtcacc     5400
cacgatttca tttgtcttat acccaggtga aggggaagg gtgaatggga ctggctggtt     5460
cctttaaatg ttaacttatg gaaatgctag ttcaaatggt aatgtcacag tgttttgtat    5520
gcagagagca agagttcaac caacagctgt ttattcatgt gtgtgtgtct ttgctgcttt    5580
gagttctctg tatctactgt gtatgtgaat ggtcatgtgg gactcagtgg tggtgttgtg    5640
actttgacct agggtccgag tgtcacagct gatcttggca ctcggcactc attggcacag    5700
tggtagttag aggtgaaaag tagagctgtc aagcccaagg gcttagcttt agggctcctc    5760
ctgagttcgg cccacagtag aagcaagatt ttaactagcc ccttttcctc ttcaccctcc    5820
catgatgcgc agtgttcaga aagctggtaa gtcctaggga tttccagaag tagcctgcag    5880
aagaaggtaa gtttgaaagc cactccaggg gtcctgatgc tgtcatgctc agtgagccat    5940
tttacagttc tccaaagtct agccctgttt cggacctgca cttcacctct aagttatgta    6000
caactcaacc tgcatccctc taaaagtcct atatccatat tcaccattgg ctaatttgag    6060
gccctgagtg ggccttgaat gctaaaaaga agcagggtac gcagggctac atgtagatac    6120
cacaccaagg ctggaggctg gtctgtcata agacagaaag aaagacgctg ggcccaattt    6180
tgacttggcc aggggacacc ttggtgtgtt tgttatcttt atctgtgggt aggctagctg    6240
acccatctcc ttgagtcatt ccctttggga aaccccactg ccagtattga tctccttttt    6300
gccttgtact gaatgacaca ttacctccac actctcccgg actaggtggt caacagggcc    6360
acagggttgc tttctgtctt tggtggggca ggggagttga cagggatgag ggtccaagga    6420
ataagcatga atgacaagaa aacaagggaa agagttaacc tgtcacatag caggttaact    6480
ttttcagggt ttgcagttag aggtattcga ccattcactg gctgagccag atcacgggaa    6540
cttgagagct tttactgtga ttcttcaatg taaaaaataa acaacaatgt caaactgtgt    6600
ttatatgatt tgtataaagc cttttttaaga ttactattta aataaacatt ataccagaga    6660
taaaaaaaa a                                                          6671
```

<210> SEQ ID NO 29
<211> LENGTH: 7123
<212> TYPE: DNA
<213> ORGANISM: Homo sapiens

<400> SEQUENCE: 29

| | | | | | |
|---|---|---|---|---|---|
| atcgaggtcc | gcgggaggct | cggagcgcgc | caggcggaca | ctcctctcgg | ctcctccccg | 60 |
| gcagcggcgg | cggctcggag | cgggctccgg | ggctcgggtg | cagcggccag | cgggcgcctg | 120 |
| gcggcgagga | ttacccgggg | aagtggttgt | ctcctggctg | gagccgcgag | acgggcgctc | 180 |
| agggcgcggg | gccggcggcg | gcgaacgaga | ggacggactc | tggcggccgg | gtcgttggcc | 240 |
| gcggggagcg | cgggcaccgg | gcgagcaggc | cgcgtcgcgc | tcaccatggt | cagctactgg | 300 |
| gacaccgggg | tcctgctgtg | cgcgctgctc | agctgtctgc | ttctcacagg | atctagttca | 360 |
| ggttcaaaat | taaagatcc | tgaactgagt | ttaaaaggca | cccagcacat | catgcaagca | 420 |
| ggccagacac | tgcatctcca | atgcaggggg | gaagcagccc | ataaatggtc | tttgcctgaa | 480 |
| atggtgagta | aggaaagcga | aaggctgagc | ataactaaat | ctgcctgtgg | aagaaatggc | 540 |
| aaacaattct | gcagtacttt | aaccttgaac | acagctcaag | caaaccacac | tggcttctac | 600 |
| agctgcaaat | atctagctgt | acctacttca | agaagaagg | aaacagaatc | tgcaatctat | 660 |
| atatttatta | gtgatacagg | tagacctttc | gtagagatgt | acagtgaaat | ccccgaaatt | 720 |
| atacacatga | ctgaaggaag | ggagctcgtc | attccctgcc | gggttacgtc | acctaacatc | 780 |
| actgttactt | taaaaaagtt | tccacttgac | actttgatcc | ctgatggaaa | acgcataatc | 840 |
| tgggacagta | gaaagggctt | catcatatca | aatgcaacgt | acaaagaaat | agggcttctg | 900 |
| acctgtgaag | caacagtcaa | tgggcatttg | tataagacaa | actatctcac | acatcgacaa | 960 |
| accaatacaa | tcatagatgt | ccaaataagc | acaccacgcc | cagtcaaatt | acttagaggc | 1020 |
| catactcttg | tcctcaattg | tactgctacc | actcccttga | acacgagagt | tcaaatgacc | 1080 |
| tggagttacc | ctgatgaaaa | aaataagaga | gcttccgtaa | ggcgacgaat | tgaccaaagc | 1140 |
| aattcccatg | ccaacatatt | ctacagtgtt | cttactattg | acaaaatgca | gaacaaagac | 1200 |
| aaaggacttt | atacttgtcg | tgtaaggagt | ggaccatcat | tcaaatctgt | taacacctca | 1260 |
| gtgcatatat | atgataaagc | attcatcact | gtgaaacatc | gaaaacagca | ggtgcttgaa | 1320 |
| accgtagctg | gcaagcggtc | ttaccggctc | tctatgaaag | tgaaggcatt | tccctcgccg | 1380 |
| gaagttgtat | ggtaaaaga | tgggttacct | gcgactgaga | aatctgctcg | ctatttgact | 1440 |
| cgtggctact | cgttaattat | caaggacgta | actgaagagg | atgcagggaa | ttatacaatc | 1500 |
| ttgctgagca | taaacagtc | aaatgtgttt | aaaaacctca | ctgccactct | aattgtcaat | 1560 |
| gtgaaacccc | agatttacga | aaaggccgtg | tcatcgtttc | cagacccggc | tctctaccca | 1620 |
| ctgggcagca | gacaaatcct | gacttgtacc | gcatatggta | tccctcaacc | tacaatcaag | 1680 |
| tggttctggc | acccctgtaa | ccataatcat | tccgaagcaa | ggtgtgactt | tgttccaat | 1740 |
| aatgaagagt | cctttatcct | ggatgctgac | agcaacatgg | gaaacagaat | tgagagcatc | 1800 |
| actcagcgca | tggcaataat | agaaggaaag | aataagatgg | ctagcaccct | tggttgtggct | 1860 |
| gactctagaa | tttctggaat | ctacatttgc | atagcttcca | ataaagttgg | gactgtggga | 1920 |
| agaaacataa | gcttttatat | cacagatgtg | ccaaatgggt | tcatgttaa | cttggaaaaa | 1980 |
| atgccgacgg | aaggagagga | cctgaaactg | tcttgcacag | ttaacaagtt | cttatacaga | 2040 |
| gacgttactt | ggattttact | gcggacagtt | aataacagaa | caatgcacta | cagtattagc | 2100 |
| aagcaaaaaa | tggccatcac | taaggagcac | tccatcactc | ttaatcttac | catcatgaat | 2160 |

```
gtttccctgc aagattcagg cacctatgcc tgcagagcca ggaatgtata cacaggggaa    2220
gaaatcctcc agaagaaaga aattacaatc agagatcagg aagcaccata cctcctgcga    2280
aacctcagtg atcacacagt ggccatcagc agttccacca ctttagactg tcatgctaat    2340
ggtgtccccg agcctcagat cacttggttt aaaaacaacc acaaaataca acaagagcct    2400
ggaattattt taggaccagg aagcagcacg ctgtttattg aaagagtcac agaagaggat    2460
gaaggtgtct atcactgcaa agccaccaac cagaagggct ctgtggaaag ttcagcatac    2520
ctcactgttc aaggaaccto ggacaagtct aatctggagc tgatcactct aacatgcacc    2580
tgtgtggctg cgactctctt ctggctccta ttaaccctct ttatccgaaa aatgaaaagg    2640
tcttcttctg aaataaagac tgactaccta tcaattataa tggacccaga tgaagttcct    2700
ttggatgagc agtgtgagcg gctcccttat gatgccagca gtgggagtt tgcccgggag    2760
agacttaaac tgggcaaatc acttggaaga ggggcttttg gaaagtggt tcaagcatca    2820
gcatttggca ttaagaaatc acctacgtgc cggactgtgg ctgtgaaaat gctgaaagag    2880
ggggccacgg ccagcgagta caaagctctg atgactgagc taaaaatctt gacccacatt    2940
ggccaccatc tgaacgtggt taacctgctg ggagcctgca ccaagcaagg agggcctctg    3000
atggtgattg ttgaatactg caaatatgga aatctctcca actacctcaa gagcaaacgt    3060
gacttatttt ttctcaacaa ggatgcagca ctacacatgg agcctaagaa agaaaaaatg    3120
gagccaggcc tggaacaagg caagaaacca agactagata gcgtcaccag cagcgaaagc    3180
tttgcgagct ccggctttca ggaagataaa agtctgagtg atgttgagga agaggaggat    3240
tctgacggtt tctacaagga gcccatcact atggaagatc tgatttctta cagttttcaa    3300
gtggccagag gcatggagtt cctgtcttcc agaaagtgca ttcatcggga cctggcagcg    3360
agaaacattc tttatctga gaacaacgtg gtgaagattt gtgattttgg ccttgcccgg    3420
gatatttata agaaccccga ttatgtgaga aaggagata ctcgacttcc tctgaaatgg    3480
atggctcctg aatctatctt tgacaaaatc tacagcacca gagcgacgt gtggtcttac    3540
ggagtattgc tgtgggaaat cttctcctta ggtgggtctc catacccagg agtacaaatg    3600
gatgaggact tttgcagtcg cctgagggaa ggcatgagga tgagagctcc tgagtactct    3660
actcctgaaa tctatcagat catgctggac tgctggcaca gagacccaaa agaaaggcca    3720
agatttgcag aacttgtgga aaaactaggt gatttgcttc aagcaaatgt acaacaggat    3780
ggtaaagact acatcccaat caatgccata ctgacaggaa atagtgggtt tacatactca    3840
actcctgcct tctctgagga cttcttcaag gaaagtattt cagctccgaa gtttaattca    3900
ggaagctctg atgatgtcag atacgtaaat gctttcaagt tcatgagcct ggaaagaatc    3960
aaaaccttg aagaactttt accgaatgcc acctccatgt tgatgactaa ccagggcgac    4020
agcagcactc tgttggcctc tcccatgctg aagcgcttca cctggactga cagcaaaccc    4080
aaggcctcgc tcaagattga cttgagagta accagtaaaa gtaaggagtc ggggctgtct    4140
gatgtcagca ggcccagttt ctgccattcc agctgtgggc acgtcagcga aggcaagcgc    4200
aggttcacct acgaccacgc tgagctggaa aggaaaatcg cgtgctgctc cccgccccca    4260
gactacaact cggtggtcct gtactccacc ccacccatct agagtttgac acgaagcctt    4320
atttctagaa gcacatgtgt atttataccc ccaggaaact agcttttgcc agtattatgc    4380
atatataagt ttacaccttt atctttccat gggagccagc tgcttttgt gattttttta    4440
atagtgcttt ttttttttg actaacaaga atgtaactcc agatagagaa atagtgacaa    4500
gtgaagaaca ctactgctaa atcctcatgt tactcagtgt tagagaaatc cttcctaaac    4560
```

```
ccaatgactt ccctgctcca accccccgcca cctcagggca cgcaggacca gtttgattga   4620
ggagctgcac tgatcaccca atgcatcacg taccccactg ggccagccct gcagcccaaa   4680
acccagggca acaagcccgt tagccccagg gatcactggc tggcctgagc aacatctcgg   4740
gagtcctcta gcaggcctaa gacatgtgag gaggaaaagg aaaaaaagca aaaagcaagg   4800
gagaaaagag aaaccgggag aaggcatgag aaagaatttg agacgcacca tgtgggcacg   4860 gaggggacg gggctcagca atgccatttc agtggcttcc cagctctgac ccttctacat   4920
ttgagggccc agccaggagc agatggacag cgatgagggg acattttctg gattctggga   4980
ggcaagaaaa ggacaaatat cttttttgga actaaagcaa attttagaac tttacctatg   5040
gaagtggttc tatgtccatt ctcattcgtg gcatgttttg atttgtagca ctgagggtgg   5100
cactcaactc tgagcccata cttttggctc ctctagtaag atgcactgaa aacttagcca   5160
gagttaggtt gtctccaggc catgatggcc ttacactgaa aatgtcacat tctatttttgg  5220 gtattaatat atagtccaga cacttaactc aatttcttgg tattattctg ttttgcacag   5280
ttagttgtga aagaaagctg agaagaatga aaatgcagtc ctgaggagag gagttttctc   5340
catatcaaaa cgagggctga tggaggaaaa aggtcaataa ggtcaaggga aaaccccgtc   5400
tctataccaa ccaaaccaat tcaccaacac agttgggacc caaaacacag gaagtcagtc   5460
acgtttcctt ttcatttaat ggggattcca ctatctcaca ctaatctgaa aggatgtgga   5520
agagcattag ctggcgcata ttaagcactt taagctcctt gagtaaaaag gtggtatgta   5580
atttatgcaa ggtatttctc cagttgggac tcaggatatt agttaatgag ccatcactag   5640
aagaaaagcc cattttcaac tgctttgaaa cttgcctggg gtctgagcat gatgggaata   5700
gggagacagg gtaggaaagg gcgcctactc ttcagggtct aaagatcaag tgggccttgg   5760
atcgctaagc tggctctgtt tgatgctatt tatgcaagtt agggtctatg tatttatgat   5820
gtctgcacct tctgcagcca gtcagaagct ggagaggcaa cagtggattg ctgcttcttg   5880
gggagaagag tatgcttcct tttatccatg taatttaact gtagaacctg agctctaagt   5940
aaccgaagaa tgtatgcctc tgttcttatg tgccacatcc ttgttaaaag gctctctgta   6000
tgaagagatg ggaccgtcat cagcacattc cctagtgagc ctactggctc ctggcagcgg   6060
cttttgtgga agactcacta gccagaagag aggagtggga cagtcctctc caccaagatc   6120
taaatccaaa caaaagcagg ctagagccag aagagaggac aaatctttgt tcttcctctt   6180
ctttacatac gcaaaccacc tgtgacagct ggcaatttta taaatcaggt aactggaagg   6240
aggttaaaca cagaaaaaag aagacctcag tcaattctct actttttttt ttttttccaa   6300
atcagataat agcccagcaa atagtgataa caaataaaac cttagctatt catgtcttga   6360
tttcaataat taattcttaa tcattaagag accataataa atactccttt tcaagagaaa   6420
agcaaaacca ttagaattgt tactcagctc cttcaaactc aggtttgtag catacatgag   6480
tccatccatc agtcaaagaa tggttccatc tggagtctta atgtagaaag aaaaatggag   6540
acttgtaata atgagctagt tacaaagtgc ttgttcatta aaatagcact gaaaattgaa   6600
acatgaatta actgataata ttccaatcat ttgccatttta tgacaaaaat ggttggcact   6660
aacaaagaac gagcacttcc tttcagagtt tctgagataa tgtacgtgga acagtctggg   6720
tggaatgggg ctgaaaccat gtgcaagtct gtgtcttgtc agtccaagaa gtgacaccga   6780
gatgttaatt ttagggaccc gtgccttgtt tcctagccca caagaatgca aacatcaaac   6840
agatactcgc tagcctcatt taaattgatt aaaggaggag tgcatctttg gccgacagtg   6900
```

```
gtgtaactgt atgtgtgtgt gtgtgtgtgt gtgtgtgtgt gtgtgtgggt gtatgtgtgt    6960
tttgtgcata actatttaag gaaactggaa ttttaaagtt acttttatac aaaccaagaa    7020
tatatgctac agatataaga cagacatggt ttggtcctat atttctagtc atgatgaatg    7080
tattttgtat accatcttca tataataaac ttccaaaaac aca                      7123

<210> SEQ ID NO 30
<211> LENGTH: 6055
<212> TYPE: DNA
<213> ORGANISM: Homo sapiens

<400> SEQUENCE: 30
actgagtccc gggaccccgg gagagcggtc aatgtgtggt cgctgcgttt cctctgcctg      60
cgccgggcat cacttgcgcg ccgcagaaag tccgtctggc agcctggata tcctctccta     120
ccggcacccg cagacgcccc tgcagccgcg gtcgcgcccc gggctcccta gcctgtgcg      180 ctcaactgtc ctgcgctgcg gggtgccgcg agttccacct ccgcgcctcc ttctctagac     240
aggcgctggg agaaagaacc ggctcccgag ttctgggcat ttcgcccggc tcgaggtgca     300
ggatgcagag caaggtgctg ctggccgtcg ccctgtggct ctgcgtggag acccgggccg     360
cctctgtggg tttgcctagt gtttctcttg atctgcccag gctcagcata caaaaagaca     420
tacttacaat taaggctaat acaactcttc aaattacttg caggggacag agggacttgg     480
actggctttg gcccaataat cagagtggca gtgagcaaag ggtggaggtg actgagtgca     540
gcgatggcct cttctgtaag acactcacaa ttccaaaagt gatcggaaat gacactggag     600
cctacaagtg cttctaccgg gaaactgact tggcctcggt catttatgtc tatgttcaag     660
attacagatc tccatttatt gcttctgtta gtgaccaaca tggagtcgtg tacattactg     720
agaacaaaaa caaactgtgt gtgattccat gtctcgggtc catttcaaat ctcaacgtgt     780
cactttgtgc aagataccca gaaaagagat tgttcctga tggtaacaga atttcctggg     840
acagcaagaa gggctttact attcccagct acatgatcag ctatgctggc atggtcttct     900
gtgaagcaaa aattaatgat gaaagttacc agtctattat gtacatagtt gtcgttgtag     960
ggtataggat ttatgatgtg ttctgagtc cgtctcatgg aattgaacta tctgttggag    1020
aaaagcttgt cttaaattgt acagcaagaa ctgaactaaa tgtggggatt gacttcaact    1080 gggaatacc ttcttcgaag catcagcata agaaacttgt aaaccgagac ctaaaaaccc     1140
agtctgggag tgagatgaag aaatttttga gcaccttaac tatagatggt gtaacccgga    1200
gtgaccaagg attgtacacc tgtgcagcat ccagtgggct gatgaccaag aagaacagca    1260
catttgtcag ggtccatgaa aaaccttttg ttgcttttgg aagtggcatg gaatctctgg    1320
tggaagccac ggtgggggag cgtgtcagaa tccctgcgaa gtaccttggt tacccacccc    1380
cagaaataaa atggtataaa aatggaatac cccttgagtc caatcacaca attaaagcgg    1440
ggcatgtact gacgattatg gaagtgagtg aaagagacac aggaaattac actgtcatcc    1500
ttaccaatcc catttcaaag gagaagcaga gccatgtggt ctctctggtt gtgtatgtcc    1560
caccccagat tggtgagaaa tctctaatct ctcctgtgga ttcctaccag tacggcacca    1620
ctcaaacgct gacatgtacg gtctatgcca ttcctcccc gcatcacatc cactggtatt    1680
ggcagttgga ggaagagtgc gccaacgagc ccagccaagc tgtctcagtg acaaacccat    1740
acccttgtga agaatggaga agtgtggagg acttccaggg aggaaataaa attgaagtta    1800
ataaaaatca atttgctcta attgaaggaa aaaacaaaac tgtaagtacc cttgttatcc    1860
aagcggcaaa tgtgtcagct ttgtacaaat gtgaagcggt caacaaagtc gggagaggag    1920
```

```
agagggtgat ctccttccac gtgaccaggg gtcctgaaat tactttgcaa cctgacatgc    1980
agcccactga gcaggagagc gtgtctttgt ggtgcactgc agacagatct acgtttgaga    2040
acctcacatg gtacaagctt ggcccacagc ctctgccaat ccatgtggga gagttgccca    2100
cacctgtttg caagaacttg gatactcttt ggaaattgaa tgccaccatg ttctctaata    2160
gcacaaatga cattttgatc atggagctta agaatgcatc cttgcaggac caaggagact    2220
atgtctgcct tgctcaagac aggaagacca agaaaagaca ttgcgtggtc aggcagctca    2280
cagtcctaga gcgtgtggca cccacgatca caggaaacct ggagaatcag acgacaagta    2340
ttggggaaag catcgaagtc tcatgcacgg catctgggaa tccccctcca cagatcatgt    2400
ggtttaaaga taatgagacc cttgtagaag actcaggcat tgtattgaag gatgggaacc    2460
ggaacctcac tatccgcaga gtgaggaagg aggacgaagg cctctacacc tgccaggcat    2520
gcagtgttct tggctgtgca aaagtggagg cattttttcat aatagaaggt gcccaggaaa    2580
agacgaactt ggaaatcatt attctagtag gcacggcggt gattgccatg ttcttctggc    2640
tacttcttgt catcatccta cggaccgtta agcgggccaa tggaggggaa ctgaagacag    2700
gctacttgtc catcgtcatg gatccagatg aactcccatt ggatgaacat tgtgaacgac    2760
tgccttatga tgccagcaaa tgggaattcc ccagagaccg gctgaagcta ggtaagcctc    2820
ttggccgtgg tgcctttggc caagtgattg aagcagatgc cttggaatt gacaagacag    2880
caacttgcag gacagtagca gtcaaaatgt tgaaagaagg agcaacacac agtgagcatc    2940
gagctctcat gtctgaactc aagatcctca ttcatattgg tcaccatctc aatgtggtca    3000
accttctagg tgcctgtacc aagccaggag ggccactcat ggtgattgtg gaattctgca    3060
aatttggaaa cctgtccact tacctgagga gcaagagaaa tgaatttgtc ccctacaaga    3120
ccaaggggc acgattccgt caagggaaag actacgttgg agcaatccct gtggatctga    3180
aacggcgctt ggacagcatc accagtagcc agagctcagc cagctctgga tttgtggagg    3240
agaagtccct cagtgatgta aagaagagg aagctcctga agatctgtat aaggacttcc    3300
tgaccttgga gcatctcatc tgttacagct tccaagtggc taagggcatg gagttcttgg    3360
catcgcgaaa gtgtatccac agggacctgg cggcacgaaa tatcctctta tcggagaaga    3420
acgtggttaa aatctgtgac tttggcttgg cccgggatat ttataaagat ccagattatg    3480
tcagaaaagg agatgctcgc ctccctttga aatggatggc cccagaaaca ttttttgaca    3540
gagtgtacac aatccagagt gacgtctggt cttttggtgt tttgctgtgg gaaatatttt    3600
ccttaggtgc ttctccatat cctggggtaa agattgatga agaattttgt aggcgattga    3660
aagaaggaac tagaatgagg gccccctgatt atactacacc agaaatgtac cagaccatgc    3720
tggactgctg gcacgggag cccagtcaga gacccacgtt ttcagagttg gtggaacatt    3780
tgggaaatct cttgcaagct aatgctcagc aggatggcaa agactacatt gttcttccga    3840
tatcagagac tttgagcatg gaagaggatt ctggactctc tctgcctacc tcacctgttt    3900
cctgtatgga ggaggaggaa gtatgtgacc ccaaattcca ttatgacaac acagcaggaa    3960
tcagtcagta tctgcagaac agtaagcgaa agagccggcc tgtgagtgta aaaacatttg    4020
aagatatccc gttagaagaa ccagaagtaa agtaatccc agatgacaac cagacggaca    4080
gtggtatggt tcttgcctca gaagagctga aactttgga agacagaacc aaattatctc    4140
catcttttgg tggaatggtg cccagcaaaa gcagggagtc tgtggcatct gaaggctcaa    4200
accagacaag cggctaccag tccggatatc actccgatga cacagacacc accgtgtact    4260
```

| | |
|---|---|
| ccagtgagga agcagaactt ttaaagctga tagagattgg agtgcaaacc ggtagcacag | 4320 |
| cccagattct ccagcctgac tcggggacca cactgagctc tcctcctgtt taaaaggaag | 4380 |
| catccacacc cccaactcct ggacatcaca tgagaggtgc tgctcagatt ttcaagtgtt | 4440 |
| gttcttttcca ccagcaggaa gtagccgcat ttgattttca tttcgacaac agaaaaagga | 4500 |
| cctcggactg cagggagcca gtcttctagg catatcctgg aagaggcttg tgacccaaga | 4560 |
| atgtgtctgt gtcttctccc agtgttgacc tgatcctctt tttcattcat ttaaaaagca | 4620 |
| tttatcatgc cccctgctgc gggtctcacc atgggtttag aacaaagacg ttcaagaaat | 4680 |
| ggccccatcc tcaaagaagt agcagtacct ggggagctga cacttctgta aaactagaag | 4740 |
| ataaaccagg caatgtaagt gttcgaggtg ttgaagatgg aaggatttg cagggctgag | 4800 |
| tctatccaag aggctttgtt taggacgtgg gtcccaagcc aagccttaag tgtggaattc | 4860 |
| ggattgatag aaaggaagac taacgttacc ttgctttgga gagtactgga gcctgcaaat | 4920 |
| gcattgtgtt tgctctggtg gaggtgggca tgggtctgt tctgaaatgt aaagggttca | 4980 |
| gacggggttt ctggttttag aaggttgcgt gttcttcgag ttgggctaaa gtagagttcg | 5040 |
| ttgtgctgtt tctgactcct aatgagagtt ccttccagac cgttacgtgt ctcctggcca | 5100 |
| agccccagga aggaaatgat gcagctctgg ctccttgtct cccaggctga tcctttattc | 5160 |
| agaataccac aaagaaagga cattcagctc aaggctccct gccgtgttga agagttctga | 5220 |
| ctgcacaaac cagcttctgg tttcttctgg aatgaatacc ctcatatctg tcctgatgtg | 5280 |
| atatgtctga gactgaatgc gggaggttca atgtgaagct gtgtgtggtg tcaaagtttc | 5340 |
| aggaaggatt ttacccttttt gttcttcccc ctgtccccaa cccactctca ccccgcaacc | 5400 |
| catcagtatt ttagttattt ggcctctact ccagtaaacc tgattgggtt tgttcactct | 5460 |
| ctgaatgatt attagccaga cttcaaaatt attttatagc ccaaattata acatctattg | 5520 |
| tattatttag acttttaaca tatagagcta tttctactga ttttttgccct tgttctgtcc | 5580 |
| ttttttttcaa aaaagaaaat gtgttttttg tttggtacca tagtgtgaaa tgctgggaac | 5640 |
| aatgactata agacatgcta tggcacatat atttatagtc tgtttatgta gaaacaaatg | 5700 |
| taatatatta aagccttata tataatgaac tttgtactat tcacattttg tatcagtatt | 5760 |
| atgtagcata acaaaggtca taatgctttc agcaattgat gtcattttat taaagaacat | 5820 |
| tgaaaaactt gaaggaatcc cttttgcaagg ttgcattact gtaccatca tttctaaaat | 5880 |
| ggaagagggg gtggctgggc acagtggccg acacctaaaa acccagcact ttgggggggcc | 5940 |
| aaggtgggag gatcgcttga gcccaggagt tcaagaccag tctggccaac atggtcagat | 6000 |
| tccatctcaa agaaaaaagg taaaaataaa ataaaatgga gaagaaggaa tcaga | 6055 |

<210> SEQ ID NO 31
<211> LENGTH: 4534
<212> TYPE: DNA
<213> ORGANISM: Homo sapiens

<400> SEQUENCE: 31

| | |
|---|---|
| aggccagccg gcgcccgcgc ggacactttc agccccgagc gcggccgct cgggtcggac | 60 |
| ccacgcgcag cggccggaga tgcagcgggg cgccgcgctg tgcctgcgac tgtggctctg | 120 |
| cctgggactc ctggacggcc tggtgagtgg ctactccatg accccccga ccttgaacat | 180 |
| cacggaggag tcacacgtca tcgacaccgg tgacagcctg tccatctcct gcaggggaca | 240 |
| gcacccctc gagtgggctt ggccaggagc tcaggaggcg ccagccaccg gagacaagga | 300 |
| cagcgaggac acgggggtgg tgcgagactg cgagggcaca gacgccaggc cctactgcaa | 360 |

```
ggtgttgctg ctgcacgagg tacatgccaa cgacacaggc agctacgtct gctactacaa   420
gtacatcaag gcacgcatcg agggcaccac ggccgccagc tcctacgtgt tcgtgagaga   480
cttttgagcag ccattcatca acaagcctga cacgctcttg gtcaacagga aggacgccat   540
gtgggtgccc tgtctggtgt ccatccccgg cctcaatgtc acgctgcgct cgcaaagctc   600
ggtgctgtgg ccagacgggc aggaggtggt gtgggatgac cggcggggca tgctcgtgtc   660
cacgccactg ctgcacgatg ccctgtacct gcagtgcgag accacctggg agaccagga   720
cttcctttcc aaccccttcc tggtgcacat cacaggcaac gagctctatg acatccagct   780
gttgcccagg aagtcgctgg agctgctggt aggggagaag ctggtcctga actgcaccgt   840
gtgggctgag tttaactcag gtgtcacctt tgactgggac tacccaggga agcaggcaga   900
gcggggtaag tgggtgcccg agcgacgctc ccagcagacc cacacagaac tctccagcat   960
cctgaccatc cacaacgtca gccagcacga cctgggctcg tatgtgtgca aggccaacaa  1020
cggcatccag cgatttcggg agagcaccga ggtcattgtg catgaaaatc ccttcatcag  1080
cgtcgagtgg ctcaaaggac ccatcctgga ggccacggca ggagacgagc tggtgaagct  1140
gcccgtgaag ctggcagcgt accccccgcc cgagttccag tggtacaagg atggaaaggc  1200
actgtccggg cgccacagtc cacatgccct ggtgctcaag gaggtgacag aggccagcac  1260
aggcacctac accctcgccc tgtggaactc cgctgctggc ctgaggcgca acatcagcct  1320
ggagctggtg gtgaatgtgc cccccagat acatgagaag gaggcctcct cccccagcat  1380
ctactcgcgt cacagccgcc aggccctcac ctgcacggcc tacggggtgc ccctgcctct  1440
cagcatccag tggcactggc ggccctggac accctgcaag atgtttgccc agcgtagtct  1500
ccggcggcgg cagcagcaag acctcatgcc acagtgccgt gactggaggg cggtgaccac  1560
gcaggatgcc gtgaacccca tcgagagcct ggacacctgg accgagtttg tggagggaaa  1620
gaataagact gtgagcaagc tggtgatcca aatgccaac gtgtctgcca tgtacaagtg  1680
tgtggtctcc aacaaggtgg ccaggatga gcggctcatc tacttctatg tgaccaccat  1740
cccccgacggc ttcaccatcg aatccaagcc atccgaggag ctactagagg gccagccggt  1800
gctcctgagc tgccaagccg acagctacaa gtacgagcat ctgcgctggt accgcctcaa  1860
cctgtccacg ctgcacgatg cgcacgggaa cccgcttctg ctcgactgca gaacgtgca  1920
tctgttcgcc acccctctgg ccgccagcct ggaggaggtg gcacctgggg cgcgccacgc  1980
cacgctcagc ctgagtatcc cccgcgtcgc gcccgagcac gagggccact atgtgtgcga  2040
agtgcaagac cggcgcagcc atgacaagca ctgccacaag aagtacctgt cggtgcaggc  2100
cctggaagcc cctcggctca cgcagaactt gaccgacctc ctggtgaacg tgagcgactc  2160
gctggagatg cagtgcttgg tggccggagc gcacgcgccc agcatcgtgt ggtacaaaga  2220
cgagaggctg ctggaggaaa agtctggagt cgacttggcg gactccaacc agaagctgag  2280
catccagcgc gtgcgcgagg aggatgcggg acgctatctg tgcagcgtgt gcaacgccaa  2340
gggctgcgtc aactcctccg ccagcgtggc cgtggaaggc tccgaggata agggcagcat  2400
ggagatcgtg atccttgtcg gtaccggcgt catcgctgtc ttcttctggg tcctcctcct  2460
cctcatcttc tgtaacatga ggaggccggc ccacgcagac atcaagacgg ctacctgtc  2520
catcatcatg gaccccgggg aggtgcctct ggaggagcaa tgcgaatacc tgtcctacga  2580
tgccagccag tgggaattcc cccgagagcg gctgcacctg gggagagtgc tcggctacgg  2640
cgccttcggg aaggtggtgg aagcctccgc tttcggcatc cacaagggca gcagctgtga  2700
```

-continued

```
caccgtggcc gtgaaaatgc tgaaagaggg cgccacggcc agcgagcacc gcgcgctgat    2760
gtcggagctc aagatcctca ttcacatcgg caaccacctc aacgtggtca acctcctcgg    2820
ggcgtgcacc aagccgcagg gccccctcat ggtgatcgtg gagttctgca agtacggcaa    2880
cctctccaac ttcctgcgcg ccaagcggga cgccttcagc ccctgcgcgg agaagtctcc    2940
cgagcagcgc ggacgcttcc gcgccatggt ggagctcgcc aggctggatc ggaggcggcc    3000
ggggagcagc gacagggtcc tcttcgcgcg gttctcgaag accgagggcg gagcgaggcg    3060
ggcttctcca gaccaagaag ctgaggacct gtggctgagc ccgctgacca tggaagatct    3120
tgtctgctac agcttccagg tggccagagg gatggagttc ctggcttccc gaaagtgcat    3180
ccacagagac ctggctgctc ggaacattct gctgtcggaa agcgacgtgg tgaagatctg    3240
tgactttggc cttgcccggg acatctacaa agacccgac tacgtccgca agggcagtgc     3300
ccggctgccc ctgaagtgga tggcccctga agcatcttc gacaaggtgt acaccacgca     3360
gagtgacgtg tggtcctttg gggtgcttct ctgggagatc ttctctctgg ggcctcccc     3420
gtaccctggg gtgcagatca tgaggagtt ctgcagcgg ctgagagacg gcacaaggat      3480
gagggccccg gagctggcca ctcccgccat acgccgcatc atgctgaact gctggtccgg    3540
agaccccaag gcgagacctg cattctcgga gctggtggga atcctggggg acctgctcca    3600
gggcaggggc ctgcaagagg aagaggaggt ctgcatggcc ccgcgcagct ctcagagctc    3660
agaagagggc agcttctcgc aggtgtccac catggcccta cacatcgccc aggctgacgc    3720
tgaggacagc ccgccaagcc tgcagcgcca cagcctggcc gccaggtatt acaactgggt    3780
gtcctttccc gggtgcctgg ccagagggc tgagacccgt ggttcctcca ggatgaagac     3840
atttgaggaa ttccccatga ccccaacgac ctacaaaggc tctgtggaca accagacaga    3900
cagtgggatg tgctggcct cggaggagtt tgagcagata gagagcaggc atagacaaga    3960
aagcggcttc aggtagctga agcagagaga gagaaggcag catacgtcag cattttcttc    4020
tctgcactta taagaaagat caaagacttt aagactttcg ctatttcttc tactgctatc    4080
tactacaaac ttcaaagagg aaccaggagg acaagaggag catgaaagtg gacaaggagt    4140
gtgaccactg aagcaccaca gggagggggtt aggcctccgg atgactgcgg gcaggcctgg   4200
ataatatcca gcctcccaca agaagctggt ggagcagagt gttccctgac tcctccaagg   4260
aaagggagac gcccttttcat ggtctgctga gtaacaggtg ccttcccaga cactggcgtt   4320
actgcttgac caaagagccc tcaagcggcc cttatgccag cgtgacagag ggctcacctc   4380
ttgccttcta ggtcacttct cacaatgtcc cttcagcacc tgaccctgtg cccaccagtt   4440
attccttggt aatatgagta atacatcaaa gagtagtatt aaaagctaat taatcatgtt   4500
tataaaaaaa aaaaaaaaa aaaaaaaaaa aaaa                                 4534
```

<210> SEQ ID NO 32
<211> LENGTH: 9071
<212> TYPE: DNA
<213> ORGANISM: Homo sapiens

<400> SEQUENCE: 32

```
atgccgctgc caccgcggag cctgcaggtg ctcctgctgc tgctgctgtt gctgctgctg      60
ctgccgggca tgtgggctga ggcaggcttg cccagggcag gcggggttc acagccccc      120
ttccgcacct tctcggccag cgactggggc ctcacccacc tagtggtgca tgagcagaca     180
ggcgaggtgt atgtgggcgc agtgaaccgc atctataagc tgtcggggaa cctgacactg     240
ctgcgggccc acgtcacggg ccctgtggag acaacgaga agtgctaccc gccgcccagc      300
```

```
gtgcagtcct gccccacgg cctgggcagt actgacaacg tcaacaagct gctgctgctg      360
gactatgccg ctaaccgcct gctggcctgt ggcagcgcct cccagggcat ctgccagttc      420
ctgcgtctgg acgatctctt caaactgggt gagccacacc accgtaagga gcactacctg      480
tccagcgtgc aggaggcagg cagcatggcg ggcgtgctca ttgccgggcc accgggccag      540
ggccaggcca agctcttcgt gggcacaccc atcgatggca agtccgagta cttccccaca      600
ctgtccagcc gtcggctcat ggccaacgag gaggatgccg acatgttcgg cttcgtgtac      660
caggatgagt ttgtgtcatc acagctcaag atcccttcgg acacgctgtc caagttcccg      720
gcctttgaca tctactatgt gtacagcttc cgcagcgagc agtttgtcta ctacctcacg      780
ctgcagctag acacacagct gacctcgcct gatgccgccg gcgagcactt cttcacgtcc      840
aagatcgtgc ggctctgtgt ggacgacccc aaattctact cgtacgttga gttccccatt      900
ggctgcgagc aggcgggtgt ggagtaccgc ctggtgcagg atgcctacct gagccggccc      960
ggccgtgccc tggcccacca gctgggcctg gctgaggacg aggacgtgct gttcactgtg     1020
ttcgcccagg gccagaagaa ccgcgtgaag ccaccaaagg agtcagcact gtgcctgttc     1080
acgctcaggg ccatcaagga gaagattaag gagcgcatcc agtcctgcta ccgtggtgag     1140
ggcaagctct ccctgccgtg gctgctcaac aaggagctgg gctgcatcaa ctcgcccctg     1200
cagatcgatg acgacttctg cgggcaggac ttcaaccagc ccctggggg cacagtcacc     1260 attgaggga cgcccctgtt cgtggacaag gatgatggcc tgaccgccgt ggctgcctat     1320
gactatcggg gccgcactgt ggtattcgcc ggcacgcgaa gtggccgcat ccgcaagatc     1380
ctggtggacc tctcaaaccc cggtggccgg cctgccctgg cctacgagag cgtcgtggcc     1440
caggagggca gccccatcct gcgagacctc gtcctcagcc caaccacca gtacctctac     1500 gccatgaccg agaagcaggt gacgcgggtg cctgtggaga gctgtgtgca gtacacgtcc     1560
tgtgagctgt gtctggggtc acgggacccc cactgtggct ggtgtgtcct gcacagcatc     1620
tgctcgcggc gggacgcctg tgagcgagca gacgagcccc agcgctttgc tgcggacctg     1680
ctgcagtgtg tgcagctgac tgtgcagccc cgcaatgtgt ctgtcaccat gtcccaggtc     1740
ccacttgtgc tgcaggcctg gaacgtgcct gacctctcag ctggcgtcaa ctgctccttc     1800
gaggacttca cggaatctga gagcgtcctg gaggatggcc ggatccactg ccgctcaccc     1860
tccgcccggg aggtggcgcc catcacgcgg ggccaggag accagcgggt ggtgaaactc     1920
tacctaaagt ccaaggagac agggaagaag tttgcgtctg tggacttcgt cttctacaac     1980
tgcagcgtcc accagtcctg cctgtcctgt gtcaacggcc cctttccctg ccactggtgc     2040
aaataccgcc acgtgtgcac acacaacgtg gctgactgcg ccttcctgga gggccgtgtc     2100
aacgtgtctg aggactgccc acagatcctg ccctccacgc agatctacgt gccagtggga     2160
gtggtaaaac ccatcaccct ggccgcacgg aacctgccac agccacagtc aggccagcgt     2220
ggatatgagt gcctcttcca catcccgggc agcccggccc gtgtcaccgc cctgcgcttc     2280
aacagctcca gcctgcagtg ccagaattcc tcgtactcct acgaggggaa cgatgtcagc     2340
gacctgccag tgaacctgtc agtcgtgtgg aacggcaact tgtcattga caacccacag     2400 aacatccagg cgcacctcta caagtgcccg gccctgcgcg agagctgcgg cctctgcctc     2460
aaggccgacc cgcgcttcga gtgcggatgg tgcgtggccg agcgccgctg ctcccctgcga     2520 caccactgcg ctgccgacac acctgcatcg tggatgcacg cgcgtcacgg cagcagtcgc     2580
tgcaccgacc ccaagatcct caagctgtcc cccgagacgg gcccgaggca gggcggcacg     2640
```

-continued

```
cggctcacta tcacaggcga gaacctgggc ctgcgattcg aagacgtgcg tctgggcgtg    2700
cgcgtgggca aggtgctgtg cagccctgtg gagagcgagt acatcagtgc ggagcagatc    2760
gtctgtgaga tcggggacgc cagctccgtg cgtgcccatg acgccctggt ggaggtgtgt    2820
gtgcgggact gctcaccaca ctaccgcgcc ctgtcaccca agcgcttcac cttcgtgaca    2880
ccaaccttct accgtgtgag cccctcccgt gggcctctgt caggggcac ctggattggc     2940 atcgagggaa gccacctgaa cgcaggcagt gatgtggctg tgtcggtcgg tggcggccc    3000 tgctccttct cctggaggaa ctcccgtgag atccggtgcc tgacaccccc cgggcagagc    3060
cctggcagcg ctcccatcat catcaacatc aaccgcgccc agctcaccaa ccctgaggtg    3120
aagtacaact acaccgagga ccccaccatc ctgaggatcg accccgagtg gagcatcaac    3180
agcggtggga ccctcctgac ggtcacaggc accaacctgg ccactgtccg tgaaccccga    3240
atccgggcca agtatggagg cattgagagg gagaacggct gcctggtgta caatgacacc    3300
accatggtat gccgcgcccc gtctgtggcc aaccctgtgc gcagcccacc agagctgggg    3360
gagcggccgg atgagctggg cttcgtcatg gacaacgtgc gctccctgct tgtgctcaac    3420
tccacctcct tcctctacta ccctgacccc gtactggagc cactcagccc cactggcctg    3480
ctggagctga agcccagctc cccactcatc ctcaagggcc ggaacctctt gccacctgca    3540
cccggcaact cccgactcaa ctacacggtg ctcatcggct ccacaccctg taccctcacc    3600
gtgtcggaga cgcaactgct gtgcgaggcg cccaacctca ctgggcagca aaggtcacg    3660 gtgcgggcag gtggcttcga gttctcgcca gggacactgc aggtgtactc ggacagcctg    3720
ctgacgctgc ctgccattgt gggcattggc ggaggcgggg tctcctgct gctggtcatc    3780 gtggctgtgc tcatcgccta caagcgcaag tcacgagatg ctgaccgcac actcaagcgg    3840
ctgcagctcc agatggacaa cctggagtcc gcgtggccc tcgaatgcaa ggaagccttt    3900
gcagagctgc agacagacat ccacgagctg accaatgacc tggacggtgc cggcatcccc    3960
ttccttgact accggacata tgccatgcgg gtgctctttc ctgggatcga ggaccaccct    4020
gtgctcaagg agatggaggt gcaggccaat gtggagaagt cgctgacact gttcgggcag    4080
ctgctgacca agaagcactt cctgctgacc ttcatccgca cgctggaggc acagcgcagc    4140
ttctccatgc gcgaccgcgg gaatgtggcc tcgctcatca tgacggccct gcagggcgag    4200
atggaatacg ccacaggcgt gctcaagcag ctgctttccg acctcatcga agaacctg      4260 gagagcaaga accacccaa gctgctactg cgccggactg agtcggtggc agagaagatg    4320
ctaactaact ggttcacctt cctcttgtat aagttcctca aggagtgcgc tggggagccg    4380
ctgttcatgc tgtactgcgc catcaagcag cagatggaga agggcccat tgacgccatc    4440 acgggtgagg cacgctactc cctgagtgag gacaagctca tccggcagca gattgactac    4500
aagacactga ccctgaactg tgtgaaccct gagaatgaga atgcacctga ggtgccggtg    4560
aaggggctgg actgtgacac ggtcacccag gccaaggaga gctgctgga cgctgcctac    4620 aagggcgtgc cctactccca gcggcccaag gccgcggaca tggacctgga gtggcgccag    4680
ggccgcatgg cgcgcatcat cctgcaggac gaggacgtca ccaccaagat tgacaacgat    4740
tggaagaggc tgaacacact ggctcactac caggtgacag acgggtcctc ggtgcactg     4800 gtgcccaagc agacgtccgc ctacaacatc tccaactcct ccaccttcac caagtccctc    4860
agcagatacg agagcatgct gcgcacggcc agcagcccg acagcctgcg ctcgcgcacg    4920
cccatgatca cgcccgacct ggagagcggc accaagctgt ggcacctggt gaagaaccac    4980
gaccacctgg accagcgtga gggtgaccgc ggcagcaaga tggtctcgga gatctacttg    5040
```

```
acacggctac tggccaccaa gggcacactg cagaagtttg tggacgacct gtttgagacc   5100
atcttcagca cggcacaccg gggctcagcc ctgccgctgg ccatcaagta catgttcgac   5160
ttcctggatg agcaggccga caagcaccag atccacgatg ctgacgtgcg ccacacctgg   5220
aagagcaact gcctgcccct gcgcttctgg gtgaacgtga tcaagaaccc acagtttgtg   5280
ttcgacattc acaagaacag catcacggac gcctgcttgt cggtggtggc ccagaccttc   5340
atggactcct gctccacctc tgagcacaag ctgggcaagg actcaccctc caacaagctg   5400
ctctacgcca aggacatccc caactacaag agctgggtgg agaggtacta tgcagacatc   5460
gccaagatgc cagccatcag cgaccaggac atgagtgcgt atctggctga gcagtcccgc   5520
ctgcacctga gccagttcaa cagcatgagc gccttgcacg agatctactc ctacatcacc   5580
aagtacaagg atgagatcct ggcagccctg gagaaggatg agcaggcgcg gcggcagcgg   5640
ctgcggagca agctggagca ggtggtggac acgatggccc tgagcagctg agccccagct   5700
gtgatcatcc agcatgatgc agcgtgagga cagctgagca gggaccggga cagccctcac   5760
cgcatgcgtg tggagtgtcc ggtggtgctc gggccgccgc agtgcagcga ctgcccggcc   5820
ctccctcccc tgcctcaccc ggtcgggtcc cggctcttcc tgtgtggagg tgatggtacc   5880
tgccacacca cagctgcgca cacagctgct tgctcagggg ccgggacagc actgggtgct   5940
caggctggcc aaggaccttc attgcctggc aagagctgcc cagtggcctt catgggagaa   6000
gggctgacct ctgaggggct gaggggtgag gccagggccc tccaggggga ggggtagcca   6060
gcttgggctg tccccttgag accaggacaa gaggctgggg gtgtcagcat tcccagcttt   6120
ccaagctgcc cccaggcggc agagtctgag ggtcccgggg cccggttggc agctggagaa   6180
agaggcaaaa agcccgtagc cgggcaagag gagctcaagt cggtctgggc ccgttgccac   6240
cgactcccac ctccagcacc catgcccgct gcaccgctgc catcctcaga ttcaccgcgt   6300
gctctgcgcg gccgaggccg gagcaccaca tccacctcgc cccagagagg ctctgctccc   6360
tcctatggag gggctgtggg ccaggctgct cagactcctg ggtggcttcc agacggaccg   6420
ggcagcccct ctccgtcctc agggctgtgc ctctgggagc cactgggcca ggggccccgg   6480
gtcgcagaga gcacgttccc gttatttatt ccccctccgcg tcctacacag gctgccctgg   6540
cagctgtctt caagggtagg ctgagctccc caccctggag cccctgaggg cggcccctga   6600
gcactcctct ctctccactc tctctgtccc tgccccagcg gcttccagtg tggcatctca   6660
gcagtgtcct ggcccctcca gagcagtggg acatctgggg actgttttg tgtttagggg    6720
aaaaaattct gctgcactct gcttgggcct tgaggtctgt ggcagggctc ctctggcccg   6780
cagtggcctg gatctatctg ggccatgagt gacgggcagt gaccagaggg actggaggcc   6840
agcggtgtcc acccttgccc tcagcaagag agaatgcatt cttaaaagaa agctgtacat   6900
gtatatatat gcatatatat atatgtggct ctagcctcag gctccagccc cagtgggta    6960
ctgtacagtt aactgaagaa gaattttaaa gacgatttga acaagaaaat gaaggcagtg   7020
ggaaagcaat gccaaatggt tgtggagaaa gtggccggag cctccctgga gtggagcagc   7080
cctgaagcct gtgcccccg acctgcgggc cgctgttttg gtttgacatg acaaggaaag    7140
gacttcctgc tgaccctgag agcctctggg gtgccgcggc accacggggc atgcatgatt   7200
gtgctagcgt ttagtctgag ttgatctttt taaaactgca agtgttgaat actagaggtt   7260
gttagaccct ttttttatgtt ttttaattaa tcagtcactt gtaaaagcaa acaagcggtc   7320
catcccctt tcaaggtcac ttttttgatg gtaccgaaga tcccatggac attaagggac    7380
```

```
agctaactgt ggccagactc agccccatgt ccttggccag gcccaaggag aggactcggc    7440
cccatggggt gtgccagtct tgcagtccgc cccagctgag tagcgtgagc cagatgacgc    7500
cacagagacc cgcctcttcc ctgaacgcgg gtcggtgtgg agtcagtgac tgctgactca    7560
gggagctcct tggccccgtg ggcactgtgc cagggctggg gccttctgct gctgccacac    7620
ccagctcagg cctgggccag cccctgcccc cagcccactg aggggtgggg cttactccct    7680
gggcagtctt gggggccaga gctgaggcca gtccatatta cagtggctgg gctgttttt    7740 tcagtagccc ctagcattgg ctgggattcc tgttcctggg tgcgcctcca cctcccttct    7800
gatgtttcct ggctatggtg gggtgggaac ctcagtttcc cccaaagtct tccctggatg    7860
ctggcttcag gttgaagtcc ctggttcttc cagttcctca cgggttaggt aggggctcct    7920
gcatcacctt cagaatccag ttccaacccc cactctcctt aggccttgtg ctctgctctg    7980
ccctgccagg ctgcccttgt ccatgtgagt agcatgggcg ggtggtgggg acggcagtgg    8040
tgatgaaggg ggtgcaccac aggcctcatg aagcagttcc cacatgggcg tgtggctggg    8100
gcgtggccac cacagagcac atggctgtgt ctaggcgcaa gcactttagc agtatctgtt    8160
tacatgcgca aggatcaagc cgactacctg tgctgtctac tgggacagca gtctccgagc    8220
tactccgtac ctccctctgc caggtcgtgg agttaggccc cagtccctac ttgtcactgg    8280
ttcccactgt gctcctaact gtgcagcacc tgggagctct ggcctggggc tggaggccct    8340
ggtaggagct gcagttggag gccgttctgt gcccagcagc ggtgagcggc tcccatgggc    8400
cctgtgtctg cagggagcca gggctgcggc acatgtgctg tgaaactggc acccacctgg    8460
cgtgctgctg ccgccacttg cttcctgcag cacctcctac cctgctccgt gtcctccctc    8520
tccccgcgcc tggctcagga gtgctggaaa agctcacgcc tcggcctggg agcctggcct    8580
cttgatatac ctcgagcttc ccctgtgctc cccagcccca ggaccactgg ccccttggcc    8640
tgaggggctg ggggccccac gacctgcagc gtcgagtccg ggagagagcc cggagcggcg    8700
tgccatctcg gctcggcctt gctgagagcc tccgccctgg ctttctccct gtctggattc    8760
agtggctcac gttggtgcta cacagctaga atagatatat ttagagagag agatattttt    8820
aagacaaagc ccacaattag ctgtccttta acaccgcaga accccctccc agaagaagag    8880
cgatccctcg gacggtccgg gcgggcaccc tcagccgggc tctttgcaga agcagcaccg    8940
ctgactgtgg gccggccct cagatgtgta catatacggc tatttcctat tttactgttc    9000
ttcagattta gtacttgtaa ataaacacac acattaagga gagattaaac attttgcta    9060 aaagctaaaa a                                                        9071
```

<210> SEQ ID NO 33
<211> LENGTH: 11457
<212> TYPE: DNA
<213> ORGANISM: Homo sapiens

<400> SEQUENCE: 33

```
cgccgccgcc gccgccaccg cgggagccag agctgccggg aggagcggca tccgcgccag      60
actggagcgg gagggcggcg gagggcagtt gctgggaatt tttcagccga gagggcgagc     120
gatccggaga gagaccccga gagcttggga gcggtagggc gtgcgagcgc cgcagccagc     180
ggagcaaacc tcgaaataga tctggaaagc caggctcccg gaggaaatgg gactgtgaac     240
gaaccggaga gcaagaaggg aaggaagcgc cgggattgct gatgtcagag gagcccggaa     300
agtcgcgctg gaaaaatctg aagacagccg gggctctgct tcttcctcag gagagacacc     360
gccggccgcc cccacacgcc ccctcggcgc ctccgggtgc ccctgagag ccggcgacag       420
```

```
cgcccagccg ggctgctgcg gggcgacgga ggactgaggg gcgcgcggag cggagaccga    480
ggagcgactt caggaataca gataagtgtc tggtggcttg acgtggattt taatgaattt    540
ggactccatg tggatttggt cgtctccctg attccgagct gcgggcaggg agagggcct    600
cgcgccgccc tcagcagccg gcggcggccg aggtagaccg agcggggacg gaaggacaga    660
ccgacgtcgc cgagctggaa tcatgtgagg gccaaccggg gaaggtggag cagatgagca    720
cacacaggag ccgtctcctc accgccgccc ctctcagcat ggaacagagg cggccctggc    780
cccgggccct ggaggtggac agccgctctg tggtcctgct ctcagtggtc tgggtgctgc    840
tggccccccc agcagccggc atgcctcagt tcagcacctt ccactctgag aatcgtgact    900
ggaccttcaa ccacttgacc gtccaccaag ggacggggc cgtctatgtg ggggccatca    960
accgggtcta taagctgaca ggcaacctga ccatccaggt ggctcataag acagggccag   1020
aagaggacaa caagtcttgt tacccgcccc tcatcgtgca gccctgcagc gaagtgctca   1080
ccctcaccaa caatgtcaac aagctgctca tcattgacta ctctgagaac cgcctgctgg   1140
cctgtgggag cctctaccag ggggtctgca agctgctgcg gctggatgac ctcttcatcc   1200
tggtggagcc atcccacaag aaggagcact acctgtccag tgtcaacaag acgggcacca   1260
tgtacggggt gattgtgcgc tctgagggtg aggatggcaa gctcttcatc ggcacggctg   1320
tggatgggaa gcaggattac ttcccgaccc tgtccagccg gaagctgccc cgagaccctg   1380
agtcctcagc catgctcgac tatgagctac acagcgattt tgtctcctct ctcatcaaga   1440
tcccttcaga caccctggcc ctggtctccc actttgacat cttctacatc tacggctttg   1500
ctagtgggg ctttgtctac tttctcactg tccagcccga ccccctgag ggtgtggcca   1560
tcaactccgc tggagacctc ttctacacct cacgcatcgt gcggctctgc aaggatgacc   1620
ccaagttcca ctcatacgtg tccctgccct tcggctgcac ccgggccggg gtggaatacc   1680
gcctcctgca ggctgcttac ctggccaagc tggggactc actggcccag gccttcaata   1740
tcaccagcca ggacgatgta ctctttgcca tcttctccaa agggcagaag cagtatcacc   1800
accgcccga tgactctgcc ctgtgtgcct ccctatccg ggccatcaac ttgcagatca   1860
aggagcgcct gcagtcctgc taccagggcg agggcaacct ggagctcaac tggctgctgg   1920
ggaaggacgt ccagtgcacc aaggcgcctg tccccatcga tgataacttc tgtggactgg   1980
acatcaacca gccccgggga ggctcaactc cagtggaggg cctgaccctg tacaccacca   2040
gcagggaccg catgacctct gtggcctcct acgtttacaa cggctacagc gtggtttttg   2100
tggggactaa gagtggcaag ctgaaaaaga ttcgggccga cggtcccccc catggtgggg   2160
tccagtacga gatggtctct gtgctcaagg acggaagccc catcctccgg gacatggcct   2220
tctccattga tcagcgctac ctgtacgtca tgtctgagag acaggtcacc agggtccccg   2280
tggagtcatg tgagcagtat acgacttgtg gggagtgcct gagctctggg gaccctcact   2340
gtggctggtg tgccctgcac aacatgtgct cccgcaggga caaatgccaa caggcctggg   2400
aacctaatcg atttgctgcc agcatcagcc agtgtgtgag ccttgcagtg catcccagca   2460
gcatctcagt atctgagcac agccggttgc ttagcctggt agtgagtgat gctcctgatc   2520
tatctgcggg tatcgcctgt gccttgggaa acctgacaga ggtggagggg caggtgtccg   2580
ggagccaggt catctgcatc tcacctgggc caaggatgt cctgtcatc ccgctggatc   2640
aagactggtt tgggctggag ctacagctga ggtccaagga gacagggaag atatttgtca   2700
gcaccgagtt caagtttttac aactgcagtg cccaccaact gtgcctgtcc tgtgtcaaca   2760
```

-continued

```
gcgccttccg ctgccattgg tgcaagtacc gcaacctctg cactcatgac cccaccacct   2820
gctccttcca ggagggccgg atcaatattt cagaggactg tccccagctg gtgcccacag   2880
aggagatctt gattccagtc ggggaggtaa agccaatcac ccttaaggcg cgaaatctgc   2940
cccagccgca gtccggccag cgaggctatg agtgtgtcct caacatacaa ggagccatcc   3000
accgggtccc cgctctgcgc ttcaacagct ccagcgttca gtgtcagaac agctcgtacc   3060
agtatgatgg catggacatc agcaatctgg ccgtggattt cgctgtggtg tggaacggca   3120
atttcatcat tgacaaccct caggacctga agtccatct ctacaagtgt gcagcccagc    3180
gggagagctg cggcctctgc ctcaaggccg accggaagtt tgagtgtggc tggtgcagcg   3240
gcgagcgcag gtgcacccct caccagcact gtaccagccc ttccagcccc tggctcgact   3300
ggtccagcca caatgtcaag tgctccaacc ctcaaatcac cgagattttg acggtgtctg   3360
gaccgccgga aggagggacg cgagtgacca tccatggcgt gaacctgggt ctggacttct   3420
ccgagatcgc ccaccatgtg caggtggctg gggtgccctg cacgcccctc ccaggggaat   3480
acatcatcgc tgagcagatt gtctgtgaga tgggccatgc cctcgtggga accacctccg   3540
ggccagtacg cctgtgtatt ggcgagtgta agccagagtt catgacgaag tcccatcagc   3600
agtacacctt cgtgaaccct tctgtgctgt cactcaaccc aatccgaggt cccgagtcag   3660
gaggcactat ggtgaccatt accggccatt accttggggc tgggagcagc gtggcagtct   3720
acctgggcaa ccagacctgc gagttctacg ggaggtcaat gagtgagatc gtgtgtgtct   3780
caccccatc atccaatggc cttggcccgg tccctgtttc tgtgagtgtc gaccgagccc    3840
atgtggatag caacctgcag tttgagtaca tagatgaccc tcgggtccag cgcatcgagc   3900
cagagtggag cattgccagt ggccacacac ccctgaccat cacaggcttc aacctggatg   3960
tcattcagga gccaaggatc cgagtcaaat tcaatggcaa agaatctgtc aatgtgtgta   4020
aagttgtgaa cacaaccacc ctcacctgcc tggcaccctc tctgaccacg gactaccgcc   4080
ctggcctgga cactgtggaa cgcccagatg agtttggatt tgtctttaac aatgtccaat   4140
ccttgctaat ttacaacgac accaagttta tctactaccc caacccgacc tttgaactgc   4200
ttagccctac tggagtcttg gatcaaaagc caggatcgcc catcattctg aagggcaaaa   4260
acctctgccc tcctgcctct ggaggggcca aactcaacta cactgtgctc atcggagaga   4320
ccccttgtgc tgtcaccgta tctgagaccc agcttctctg cgagcctccc aacctcaccg   4380
ggcagcacaa ggtcatggtt cacgtgggcg ggatggtgtt ctcgcctggc tcggtgagtg   4440
tcatctcaga cagcttgctg accctgccag ccatcgtcag catcgcggcc ggcggcagcc   4500
tcctcctcat catcgtcatc atcgtcctca ttgcctacaa gcgcaagtct cgagaaaatg   4560
acctcactct caagcggctg caaatgcaga tggacaatct ggagtcccgt gtggccttgg   4620
agtgcaagga agcttttgct gagctccaga cggatatcaa tgagttgacc agtgacctgg   4680
accgctcagg aatcccttac ctggactatc gtacctacgc tatgcgagtc ctgttcccgg   4740
gcatcgagga ccacccgtc ctgcgggagc tggaggtaca aggaaacggg cagcagcacg    4800
tggagaaggc cctgaagctc tttgcccagc tcatcaacaa caaggtgttc ctgctgacct   4860
tcatccgcac cctggagctg cagcgcagtt tctccatgcg cgaccggggc aacgtggctt   4920
cgctcatcat gaccggcctg caggggccgc tggaatatgc cactgatgtc ctcaagcagc   4980
tgctctctga cctcatcgat aagaacctgg agaacaagaa ccaccccaag ctgctactcc   5040
ggaggacaga gtctgtggct gaaaagatgc tgaccaattg gttcgccttc ctcctgcaca   5100
agttcctaaa ggagtgcgca ggggagccac tcttcatgct atactgtgcc atcaagcagc   5160
```

```
agatggagaa gggcccccatt gatgccatca cgggcgaggc cgctactcc  ctgagcgagg   5220
acaagctcat ccggcagcag atcgagtaca agaccctgat cctgaactgc gtcaaccctg   5280
acaacgagaa cagtccagag atcccagtga aggtgttaaa ctgtgacacc atcacacagg   5340
tcaaggagaa gattcttgat gccgtgtata agaatgtgcc ctattcccag cggccgaggg   5400
cagtggacat ggacttggag tggcgccaag gccggatcgc ccgggtcgtg ctgcaagatg   5460
aggacatcac caccaagatt gagggtgact ggaagcggct caacacactg atgcattatc   5520
aggtgtcaga caggtcggtg gtggctctgg tccccaaaca gacctcctcc tacaacatcc   5580
ctgcctctgc cagcatctcc cggacgtcca tcagcagata cgactcctcc ttcaggtata   5640
cgggcagccc cgacagcctg cggtcccggg ccccgatgat caccccagac ctggaaagtg   5700
gggtcaaggt gtggcatctg gtgaagaacc atgaccacgg tgaccagaag gagggtgacc   5760
ggggcagcaa gatggtgtcc gagatctacc tgacccggct actggccacc aagggcaccc   5820
tgcagaagtt tgtggacgac ttgtttgaga ccttgttcag cactgtgcac cggggcagcg   5880
ctctccccct ggccatcaag tacatgtttg atttcctaga tgagcaggca gacaggcaca   5940
gcatccatga cacagatgtg cggcacacct ggaaaagcaa ctgcctccct ctgcgcttct   6000
gggtgaacgt gattaagaac ccccagttcg tgtttgacat ccacaagggc agcatcacgg   6060
acgcctgcct ctctgtggtg gcccagacct tcatggactc ttgttcaacg tcagagcacc   6120
ggctgggcaa ggactccccc tccaacaagc tgctctatgc caaggacatc cccagctaca   6180
agagctgggt ggagagatac tacgcagaca tcgccaagct cccagccatc agtgaccagg   6240
acatgaatgc ctacctcgcc gagcagtccc gcctgcacgc cgtggagttc aacatgctga   6300
gtgccctcaa tgagatctac tcctatgtca gcaagtatag tgaggagctc atcgggccc    6360
tagagcagga tgagcaggca cggcggcagc ggctggctta aaggtggag cagctcatta    6420
atgccatgtc cattgagagc tgagaggagg agcctcgcat tcctgggaag agggacctgt   6480
ccaagctgtc acactgggag tctcagatgg aaggacaagt gatggggatc aggccccaga   6540
gcttgctgtc ccctgagacc ccatcctggg gagaggggag gactcctctc cctacgccag   6600
ccaagtttcg tcatagccag ttccagctgg gagagacagt gggcgtcgtc catcctcagt   6660
gagaacacca gagaacccgg ggccgggaga aggtggttct tcaagccgag aggcacgagc   6720
tggggacagt tctgcctctg tgactgctgc tttgcatgaa aactcatttg atgtatattg   6780
gggaaataat gagaacttta tttaattttt ttaagaaaaa gggaaaaaaa cagaaataaa   6840
acaaaaagcc gccctgttaa tcccgtccaa cttttgtttta attctgattt ctgtctccct   6900
tccatctttt ctcccattcc tccttcttta tataatgcct atttccaaat gccagagaaa   6960
gcagagatgc tgagagacat tggagagaaa atgactgtct cctttccctt gaaattaaaa   7020
aaaaaaaaaa aaagagaaag aggagaagaa gaatgatgag cacaagtatg caccaaacac   7080
ttcgcaaaaa cagaggccag taaaacctgg aattatcccg gcagccagag gagtatggaa   7140
cttccagaac tttgcacaaa ttgcaaagcc atcaagagct caccctggct gactggaaac   7200
tgagctttat ctaccacaca cctgtatatt ctcatctttt gagaggagat gtgtacctag   7260
atagtaccaa tgcttttgc tactgttttt tgttttgtt tatttaatcc taaacctcaa     7320
caaatgagga gctggtcttt gatatgtttc ctttcaattt ccctaaagtt actatgagaa   7380
gtggggtgag gtgggcctct cccagaccag acacctggca gccctgcctc atatcaatcc   7440
ctgtcataaa ccaggcaccc tggggaaacg gcctggaggt gtgtgggcca ggcctccacg   7500
```

```
aggttccatt tgaaagttga tttggagaca taggtgtttg actttggagt tcactccaat    7560
catccagtgg tccctggcaa ttaaaaagaa aacaaaaatc aaacactgtt tacagcaagc    7620
aatacttgaa gagcataggt tacagaagct gcagtattta ttattatgct ttctttcttt    7680
cattctctcg tgcctggaga ggggagacca cccttcgctc atatacgaaa gctcctgacc    7740
atctgggcct acagcacttc ctcagtagaa atgactgtgg catgcccacg ttactacctt    7800
ctgcctctct ttctgcctct cacggacttg tgagtgtgaa ggacaagtgg atgacttctc    7860
actggacttt ccttctctgt ctcttctgat gatgcctaaa actatggata accaattctc    7920
ctgagtgtag attccaaaca aagagaccaa agctccatgc ccaggtccaa aggccccata    7980
gaagccagtg ggagtcatcg agaggaaagg cgctctgtga gtgtcaggac cttggtggcc    8040
aggatagcca tcagagtgtc caggcctccc acattacctt ggatccgagc agccagctcc    8100
aactgttctg caagcagcac tggagtcagg gggtaggagg acaagtggaa gcaaaggtgt    8160
gggactgggg aagacaaaga ggaacaagct gcccttcctc acttttcaaa gggtcaggaa    8220
tcctaggcta tgatgctggg aagctagacc agctcctcca agagagacta gaccagggtc    8280
attttctctg ttattaactc tgggctccag cttctccgtg ccctgcttta cctccaagtg    8340
gttccaattt ccaaaggccc tgctgaccac atgtgattcc caggagaggg ctggggggagg    8400 ggagcgcaga ggtctggctt ccatccttgg cgtgtagctt tggatcgctg tctaaccaca    8460
cagcagacgt tgcccggtct ccccagctct agtttcttgc ctgaatgcgg ctgacaaatg    8520
ggaagagaaa agcattcagc aaaatactca ggaaacttgc tgttttcatt ataattcaca    8580
accagccatg ccaaggccac tttcttttga aaatccactt cttaaagtt tctcaggccc    8640 tattagtagc ctgaaggaaa tactaatgac tggccttccg cactaagcca aagtgtttgc    8700
tcttcatagc actcaaagct tatcagcgca gagcccataa tttatggaga taaaaggaaa    8760
ggagatatag gtaagaagag tgtgaccagg agaccttatg ctacctgtaa aaaagttcag    8820 cccacccat ctaacttctg agctctgttt gggtgaagat tttctggccg catggctgct    8880
cagactggca tccaggcttt gctccaccaa gaagttaaag gcagtcggac atctcagtag    8940
catctctacc agcccttaac tcaatgcatc tacctggcat ctcccagcag ttactttgg    9000 agacgattca ctgcccctgg ggcgtttcct tgaaggtttg tggagagcgt ggagaatgat    9060
ggggcaatgg ccaattggag ggtggagagt gaagagccgg agctggctgt gagtggtttg    9120
gccacatttc tcaggattcc atgagagact tggggaactt gggctgacaa aggaagtagc    9180
ctggggcatc cttaaggaag gaattaagaa aagggaaaaa gctggactca agccacgcca    9240
tgagggtgaa aggttataag gccctgcccc ctttccagct gcccacctgt tcctcctcca    9300
cacctcttcg ctttgggcca ccaagaacca atgaagtcca cacccttgg atgagaaaaa    9360 gagggagttg gttggcctct cttctccctg ttatccaatt tgaggatatt ttgaccttgg    9420
gtaaggatga agtgttaaag ccacagctcc tctccacaag aagccattca tcttggggga    9480
ggcagagagg gaagtctctc tccaaagtct atccagcttc gcttcgtttc attgatctgc    9540
acaagagaca atgctctgga aaaggaagag gaccccagaa gggtgcttgg caagacagag    9600
gatgctaatg gcaatggag agcactccct ccagctggcc cctgctgctg cctcccgtcc    9660
tctgcatggg gtcaggtgct tctgtgcttg ctgtcctacc tctctccaca gcagggctct    9720
caaaaccatt ttgatccccc attggcagag ggttcccctc tttacagagt tcagtcatta    9780
aaagcatgga tcagctgtta atctcattgg aggagggaac tgtttcctgc attcattcat    9840
ctgggaacct tcttgagtag ccactgtctg ccagccactg ctctagagat gggaaaacag    9900
```

```
cacggaacaa aaccaaggtc tttcttccag cgaatttata tccttcagga agctggttcc    9960
tgccaccaac ttagcaggca acagttctcc tccctagtg gcacagggta ccagttttgt    10020
aggaaaagtg gtccagcaaa ggaagaaagc agaccaaccc agctgcctta ccttattctg   10080
gggccattcc cccagcgatg agagctgctc ttgtttctac tgccaccatc tcttctggct   10140
gcacttcacc tgctgcttga gcttctgacc ttccttcagt tccaccaaat gaggacagga   10200
aatagcagtc aagaccctg gccctgctga gcgtgaaaca gaagcaatgg atgagtgctg    10260
gacgaagaat ggcctgggca gaacaaatag ggagcatttg aaagcttctg gctgataaat   10320
ctccaggtgc atcccggttg ccacgcctgc ccccattaac ctgctcctgg taaatactga   10380
tccagcagct gctccaggag aggccgtctt ttttcccag ccacgctgtg tcttgcatga    10440
gactcctggg gcctgggcac agagagaaaa gaattgagac tcaggaggct cagtgggtga   10500
gaaaatgcaa agtggcttca cagacacagg gctgtgggag cagatcgacg gggaacttgg   10560
gagatgaact tcagggcctt ccgacgcctt gtctcaggaa catgctttga gaaaaatggt    10620
agcatccttt ccataactca gtctctcttc cctagtttcc ctgaagtgtg acgttttagt    10680
atctggagct cagtgatccc catgaatgag ggataaagtt tcactcttgg tatttctaa    10740 ctagtgctag ggaaagtcct gagacacgat cacagccact gcttggcata cagggcctcc   10800
acccaataag caaactggag attcctcagc ctctcgtgga cacccacatc tcattcttct   10860
cacagcagag aagctctccc ttcagcctga gctgtcttct ttctgctgca gtgcagcctg    10920
ctccctccta ccctggcctc aaggaaggta ggaaacatct tctgcatttc aaagtcctca   10980 cttttgactta tttggccttc atcttggcat ggaaggtggc aggcagaatg gaaatactcc   11040 cccaaacag aacagatatt cttgcgtgtg taagggcaga agggacaagc tctctatccc    11100
atgagactag gggccggagc ccacctgcct ttccccacaa cttttcctgc tcaaacccac   11160
tcctcttgac acactggaat ctgtattata tattttta agaaaataca atgatggttg    11220
tctggttttg ttgttttac aggtgttgtg gaataaaaac tgtaagaaaa ttaagtattt    11280
aaaatgttcc aataaagtgg ggttttttgt tattctaata tattattgtg tacctattgt   11340
aaatatgaaa cactcctatt ttgcaagctg aggacacaat ttgtactgtt gttatatata   11400
aataaagttt actgaattaa aaaaaccttta atctttaaa taaaaaaaaa aaaaaa       11457
```

<210> SEQ ID NO 34
<211> LENGTH: 6763
<212> TYPE: DNA
<213> ORGANISM: Homo sapiens

<400> SEQUENCE: 34

```
tgtgtgggcg gcggcggcgg cggctgcgcg cttggggccc ggggcgcggg gcgaggccgt     60
ggggacgtgc gagcggggcc gcggtggggc tcggggcgc gtccacgtgg ccagagggcg    120
gccacccgga gccagcggag ggacaggcct gtccccaggc gcggctgccg gccatgccct    180
ctgtctgcct cctcctgctg ctcttccttg ccgtgggggg ggccctgggc aacaggccct    240
tccgtgcctt cgtggtgaca gacaccacgc ttacccacct ggctgtgcac cgggtgactg    300
gggaggtgtt cgtgggcgca gtgaaccgag tctttaagct ggccccccaac ctgactgagc    360 tgcgggccca tgtcacgggg cccgtcgagg acaacgctcg ctgctacccg ccccccagca   420
tgcgcgtgtg tgcccaccgc ctggcccccg tggacaacat caacaagctg ctgctcatag    480
actatgcggc ccgccgcctg gtggcctgcg gcagcatctg gcagggcatc tgccagttcc    540
```

```
tgcgtctgga cgacctcttc aagctgggtg agccgcacca ccgcaaggag cactacctgt    600
cgggggccca ggagcccgac tccatggctg gtgtcattgt ggagcagggc caggggccca    660
gcaagctgtt tgtgggcact gctgtcgacg gcaagtcgga gtacttcccc accttgagct    720
cccgcaagct catcagtgat gaagacagcg cggacatgtt cagtctcgtg taccaggatg    780
agtttgtgtc ctcccagatc aagatcccct cagacacgct gtccttgtac cctgcctttg    840
acatctacta catctacggc ttcgtcagcg cctccttcgt gtacttcctg acgtgcagc     900 tggacaccca gcagacgctg ttggacacag cgggcgagaa attttttcacg tccaagatcg    960 tgcgcatgtg cgcgggagac tcagagttct actcatacgt ggaattcccc atcggctgct   1020
cctggcgcgg cgtggagtac cgcttggtgc agagcgccca cctggccaag cctggcctgc   1080
tgctggccca ggccctgggc gtgccggctg atgaggacgt cctcttcacc atcttctctc   1140
agggccagaa gaaccgggcc agcccacccc ggcagaccat cctctgcctc ttcaccctca   1200
gcaacatcaa tgcccacatc cggcgccgca tccagtcctg ctatcgtggg gagggcactc   1260
tggctctgcc ctggctgctg aacaaggagc tgccctgcat caacaccccc atgcagatca   1320
acggcaactt ctgtgggctg tgttgaacc agcctctggg aggcctgcat gtgatcgagg    1380 ggctgccccct gctggccgac agcaccgacg gcatggccag cgtggccgcc tacacctacc   1440
gccagcactc tgtggtcttc attggcacgc gcagcggcag cttgaagaag gtgcgggtcg   1500
atggcttcca ggatgcccac ctgtatgaga cagtccccgt ggtggatggc agccccatcc   1560
tccgagacct gctcttcagc ccggaccacc ggcacatcta tctcctgagt gagaagcagg   1620
tgagccagct cccggtggag acctgtgagc agtaccagag ctgcgcagcc tgcctgggct   1680
ccggggaccc gcactgtggt tggtgtgtgc tgcgacacag gtgctgccgc gaagggcct    1740 gtctgggcgc ctctgcccca cacggctttg ctgaggagct gagcaagtgt gtccaggtgc   1800
gggtccggcc caacaatgtg tcagtgacgt cacctggggt gcagctgacc gtcaccctgc   1860
acaacgtgcc agacctcagt gcgggcgtga gctgcgcctt cgaggcggcg cggagaacg    1920 aggcggtcct gctgccctcc ggtgaactgc tctgccctcc accctccctc caggagctcc   1980
gagctcttac caggggggcat ggggccaccc gcactgtgcg gctgcagctt ctctccaagg   2040
agacaggcgt gaggtttgcc ggtgctgact ttgtcttcta caactgcagc gtcctccagt   2100
cgtgcatgtc ctgtgttggc agccttacc cctgccactg tgtaagtac cgccacacgt    2160 gtaccagccg cccccacgag tgctccttcc aggagggcag ggtccacagc cctgagggct   2220
gccctgagat cctgcccagt ggggacctcc tgatccccgt tggggtcatg cagcctctta   2280
ccttgcgggc taagaaccta cctcagccgc agtcgggcca aagaactat gagtgcgtgg    2340 tgcgggtgca ggggcggcag cagcgggtgc ctgccgtgcg cttcaacagc agcagtgtgc   2400
agtgccagaa cgcctcgtac tcctatgaag gtgatgagca tggtgacacc gagctggact   2460
tctccgtggt ctgggatgga gacttcccca tagacaagcc tcccagcttc cgagccctcc   2520
tgtacaagtg ctgggcgcag cggcccagct gtggcctctg cctcaaggct gatccccgct   2580
tcaactgtgg ctggtgcatc tcagagcaca ggtgccagct gcggacccac tgcccggccc   2640
cgaagaccaa ctggatgcac ctgagccaga agggcacccg tgcagccac ccccgcatca    2700 cgcagatcca ccctctcgtg gggcccaagg aaggaggcac ccgggtcacc atcgtgggtg   2760
acaacctggg cctcttgtcc cgagaggtgg gcctgcgggt ggctggcgtg cgttgcaact   2820
ccattccggc cgagtacatc agtgctgaga ggatcgtgtg tgagatggag gagtcgctgg   2880
tgcccagccc gccgccgggg cccgtggagc tgtgtgtggg tgactgttca gccgacttcc   2940
```

```
gcacgcagtc ggagcaggtc tacagctttg tgaccccaac gtttgaccaa gtgagtccca   3000
gccgtggccc ggcgtccggg ggcacacggc ttaccatctc aggcagctct ctggatgctg   3060
gcagcagggt cacagtgact gtgagggaca gcgagtgcca gtttgtaagg agagatgcca   3120
aggcgatcgt gtgcatctca cctctctcca ccctgggccc cagccaggcc cccatcacac   3180
ttgccattga ccgggctaac atctccagcc ccgggctcat ctacacctac actcaggacc   3240
ccaccgtcac ccgccttgag cccacctgga gcatcatcaa tggaagcact gccatcactg   3300
tgagtgggac ccacctgctg acggtccagg agccccgggt ccgtgccaag taccgcggca   3360
ttgagaccac caatacatgc caagtgatca acgacactgc catgctgtgt aaggcccccg   3420
gcatctttct tgggcggccc cagcctcggg cgcaaggcga gcaccctgat gagtttggct   3480
tcctgctgga ccacgtgcaa acggccgct ccctcaaccg ctcctccttt acctactacc   3540
ctgatcccag ctttgagccg ctggggccct ctggcgtgct ggacgtcaaa ccgggctccc   3600
acgtggtgct gaagggcaag aacctgattc ccgcggcagc cggcagctcc cgcctcaact   3660
acactgtgct gataggaggc cagccgtgtt cgctcactgt ctcggacaca caactcctgt   3720
gcgactcacc cagccagact ggccggcagc ctgtcatggt gctggtgggt ggcctggagt   3780
tctggctggg caccctgcac atctcggcag agcgggcgct gaccctaccg gccatgatgg   3840
ggctggcggc gggggtggg ctcctgctgc tggccatcac agccgtgctg gtggcgtaca   3900
agcgcaagac tcaggacgcg gaccgtaccc tcaagcgtct gcagctgcag atggacaacc   3960
tggagtcccg tgtggccctg gagtgcaagg aagcttttgc agagctgcag acggacatca   4020
atgagctgac taaccacatg gacgaggtgc agatccccct cctggactac cggacttacg   4080
ccgtgcgcgt gctcttcccg ggcatcgagg cccacccggt gctcaaggag ctggatacgc   4140
cacccaacgt ggagaaggcc ctgcgcctct tcgggcagct gctgcacagc cgcgcgttcg   4200
tgcttacctt catccacacg ctggaggccc agagcagctt ctccatgcgc gaccgcggca   4260
ccgtggcctc gctcaccatg gtggccctgc agagccggct cgactatgcc acggggctgc   4320
tcaagcaact gctggccgac ctcatcgaga gaacctcga gagcaagaac cacccccaagc   4380 tgctgctacg caggacagag tcagtggctg agaagatgct taccaactgg ttcacgttcc   4440
tgctgcataa gtttctgaag gagtgtgctg gggagcctct cttcctgctt tactgtgcca   4500
tcaagcagca gatggagaag ggccccattg atgccatcac gggcgaggca cgatactccc   4560
tgagcgagga caagctcatc cgtcagcaga tcgactacaa gacactgacc cttcactgcg   4620
tgtgtccgga gaacgagggc agcgcccagg tcccagtgaa ggttctcaac tgtgacagca   4680
tcacccaggc caaagataag ctgctggaca ctgtgtacaa gggcattccg tactcccagc   4740
gtcccaaagc tgaggacatg gacctggagt ggcgccaggg ccgcatgact cgcatcatcc   4800
tccaggatga ggatgtcacc accaagatcg agtgtgactg aagaggctc aactcactgg   4860 cccactacca ggtgacagac ggttccttgg tggcattggt gcccaaacaa gtgtctgcct   4920
ataacatggc caactccttc accttcaccc gctccctcag ccgctacgag agcttgctcc   4980
gcacggccag cagccctgat agcctccgct cacgggcacc catgattacg cctgaccagg   5040
agacaggcac caaattgtgg cacctggtga aaaaccacga ccatgccgac catcgcgagg   5100
gggaccgtgg cagcaagatg gtctccgaga tctacctgac acggctgctg gccaccaagg   5160
gcacactgca gaagttcgtg gatgaccict ttgagacagt gttcagcaca gcccaccggg   5220
gctcggccct gccccctggcc atcaagtaca tgttcgactt cctggatgag caggcggacc   5280
```

| | |
|---|---|
| agcgccagat cagcgacccc gatgtgcgcc acacctggaa gagcaactgc ctgccgctgc | 5340 |
| gcttctgggt gaatgtgatc aagaacccgc agttcgtgtt cgacatccac aagaacagca | 5400 |
| tcacggatgc ctgcctgtcg gtggtagccc agaccttcat ggactcctgc tctacatccg | 5460 |
| agcaccgcct ggggaaggac tcgccctcca acaaactgct ctacgccaag gacatcccca | 5520 |
| actacaagag ctgggtggag aggtattatc gagacattgc aaagatggca tccatcagcg | 5580 |
| accaggacat ggatgcctac ctggtggagc agtcccgcct ccacgccagc gacttcagcg | 5640 |
| tcctgagtgc gctcaacgag ctgtatttct atgtcaccaa gtaccgccag gagattctca | 5700 |
| cggctctgga ccgagatgcc tcttgtcgga agcataagtt gcggcagaaa ctggaacaga | 5760 |
| tcatcagcct cgtgtccagc gacagctaag gtggtggaat cggtgaggag ggggcttctc | 5820 |
| agtcctgtgc cgtcctccca tccagggag tggctggctc aagcctgggt ccccgggctg | 5880 |
| agccctggat tgggtatcgt ggggcaggtc accctggcca cgatgccccc ggcacaccca | 5940 |
| ggccccttc attagtgcct tgctttgggc cctgcagggg gaggggtgac agggcgagcc | 6000 |
| cccacccag cagcagcaat accccacc tcctgccctg tgcccaggtg ttgggacagt | 6060 |
| cccaccctcc ctgctatttta tatccctctg cctatttatt gaatcgaact tcgcctctgt | 6120 |
| ctccatctgt aaatatgtgt cccccaccg gatgtcgcca ccctcactca cctgcctctt | 6180 |
| cttgagctgt cctgggccct gccaccgtc tgggctcctt tgtgtagcat tatcagcctc | 6240 |
| ggtctggcct ctggcacctc acccttgcca tggctgaccc cacccattcc aaggcggggt | 6300 |
| cacggtacca gcagcacttg gggtgaggcc tccaaagctt cctcagaatt gtggctgtgc | 6360 |
| cacgctggac cacagggtcc ccctcaagca tctcggggcc ctattctctc tgagcacctg | 6420 |
| gagggctgga ctcaggcttg tgccagggcc tgacttgggc ctgggggccc tagaacactc | 6480 |
| ctcctcctga gcctactgcc aaacgtcctc agtgttgtct gcacctgctc cgactccttc | 6540 |
| agccgcccca ttcagcgccc gctccgtcca gtgcccgccc tgtggggcca aggcggccgt | 6600 |
| gccttactac tctgtgtctt ctgcctcctc tgaggaatct ggccctgtct gacagtccca | 6660 |
| gacccccgt tctctcctct ttagttgcat gagtttttct ttgttcatgg aatgttttt | 6720 |
| cctgattaaa tgttggggaa atgccaaaaa aaaaaaaaa aaa | 6763 |

<210> SEQ ID NO 35
<211> LENGTH: 13061
<212> TYPE: DNA
<213> ORGANISM: Homo sapiens

<400> SEQUENCE: 35

| | |
|---|---|
| tgcgttcggg gctggggctg gaggaggcag ccacacgcgc gcacacgcac acgttcagag | 60 |
| gagggcgaga ggcagcggca taggctccat ctgcagtgtc aatgcggcgc tcccgctgaa | 120 |
| ggagggaaac gcggcgcgtc cagtagggga gactgcattg ctgagtcctg gccctctgag | 180 |
| gggacgactg tgcctgagtg ctgctgtgcc actgggaccc gcctctgcca tgaaagccat | 240 |
| gccctggaac tggacctgcc ttctctccca cctcctcatg gtgggcatgg gctcctccac | 300 |
| tttgctcacc cggcagccag ccccgctgtc ccagaagcag cggtcatttg tcacattccg | 360 |
| aggagagccc gccgagggtt tcaatcacct ggtggtggat gagaggacag gacacattta | 420 |
| cttggggggcc gtcaatcgga tttacaagct ctccagcgac ctgaaggtct tggtgacgca | 480 |
| tgagacaggg ccggacgagg acaacccaa gtgttaccca cccgcatcg tccagacctg | 540 |
| caatgagccc ctgaccacca ccaacaatgt caacaagatg ctcctcatag actacaagga | 600 |
| gaacaggctg attgcctgtg ggagcctgta ccaaggcatc tgcaagctgc tgaggctgga | 660 |

```
ggacctcttc aagctggggg agccttatca taagaaggag cactatctgt caggtgtcaa    720
cgagagcggc tcagtctttg gagtgatcgt ctcctacagc aacctggatg acaagctgtt    780
cattgccacg gcagtggatg ggaagcccga gtattttccc accatctcca gccggaaact    840
gaccaagaac tctgaggcgg atggcatgtt cgcgtacgtc ttccatgatg agttcgtggc    900
ctcgatgatt aagatccctt cggacacctt caccatcatc cctgactttg atatctacta    960
tgtctatggt tttagcagtg caactttgt ctacttttg accctccaac ctgagatggt   1020
gtctccacca ggctccacca ccaaggagca ggtgtataca tccaagctcg tgaggctttg   1080
caaggaggac acagccttca actcctatgt agaggtgccc attggctgtg agcgcagtgg   1140
ggtggagtac cgcctgctgc aggctgccta cctgtccaaa gcgggggccg tgcttggcag   1200
gacccttgga gtccatccag atgatgacct gctcttcacc gtcttctcca agggccagaa   1260
gcggaaaatg aaatccctgg atgagtcggc cctgtgcatc ttcatcttga agcagataaa   1320
tgaccgcatt aaggagcggc tgcagtcttg ttaccggggc gagggcacgc tggacctggc   1380
ctggctcaag gtgaaggaca tcccctgcag cagtgcgctc ttaaccattg acgataactt   1440
ctgtggcctg acatgaatg ctcccctggg agtgtccgac atggtgcgtg gaattcccgt   1500
cttcacggag gacagggacc gcatgacgtc tgtcatcgca tatgtctaca agaaccactc   1560
tctggccttt gtgggcacca aaagtggcaa gctgaagaag atccgggtgg atggacccag   1620
gggcaacgcc ctccagtatg agacggtgca ggtggtggac cccggcccag tcctccggga   1680
tatgccttc tccaaggacc acgagcaact ctacatcatg tcagagaggc agctcaccag   1740
agtccctgtg gagtcctgtg gtcagtatca gagctgcggc gagtgccttg gctcaggcga   1800
cccccactgt ggctggtgtg tgctgcacaa cacttgcacc cggaaggagc ggtgtgagcg   1860
gtccaaggag ccccgcaggt tgcctcgga gatgaagcag tgtgtccggc tgacggtcca   1920
tcccaacaat atctccgtct ctcagtacaa cgtgctgctg gtcctggaga cgtacaatgt   1980
cccggagctg tcagctggcg tcaactgcac ctttgaggac ctgtcagaga tggatgggct   2040
ggtcgtgggc aatcagatcc agtgctactc ccctgcagcc aaggaggtgc cccggatcat   2100
cacagagaat ggggaccacc atgtcgtaca gcttcagctc aaatcaaagg agaccggcat   2160
gaccttcgcc agcaccagct ttgtcttcta caattgcagc gtccacaatt cgtgcctgtc   2220
ctgcgtggag agtccatacc gctgccactg gtgtaaatac cggcatgtct gcacccatga   2280
ccccaagacc tgctccttcc aggaaggccg agtgaagctg cccgaggact gcccccagct   2340
gctgcgagtg gacaagatcc tggtgcccgt ggaggtgatc aagcctatca cgctgaaggc   2400
caagaacctc cccagcccc agtctgggca gcgtggctac gaatgcatcc tcaacattca   2460
gggcagcgag cagcgagtgc ccgccctgcg cttcaacagc tccagcgtac agtgccagaa   2520
cacctcttat tcctatgaag ggatggagat caacaacctg cccgtggagt tgacagtcgt   2580
gtggaatggg cacttcaaca ttgacaaccc agctcagaat aaagttcacc tctacaagtg   2640
tggagccatg cgtgagagct gcgggctgtg cctcaaggct gacccagact tcgcatgtgg   2700
ctggtgccag gcccaggcc agtgcaccct gcgccagcac tgccctgccc aggagagcca   2760
gtggctggag ctgtctggtg ccaaaagcaa gtgcacaaac ccccgcatca cagagataat   2820
ccccggtgaca ggccccccggg aaggggggcac caaggtcact atccgagggg agaacctggg   2880
cctggaattt cgcgacatcg cctcccatgt caaggttgct ggcgtggagt gcagcccttt   2940
agtggatggt tacatccctg cagaacagat cgtgtgtgag atgggggagg ccaagcccag   3000
```

```
ccagcatgca ggcttcgtgg agatctgcgt ggctgtgtgt cggcctgaat tcatggcccg     3060
gtcctcacag ctctattact tcatgacact gactctctca gatctgaagc ccagccgggg     3120
gcccatgtcc ggagggaccc aagtgaccat cacaggcacc aacctgaatg ccggaagcaa     3180
cgtggtggta tgtttggaa agcagccctg tctcttccac aggcgatctc catcctacat      3240
tgtctgcaac accacatcct cagatgaggt gctagagatg aaggtgtcgg tgcaggtgga     3300
cagggccaag atccaccagg acctggtctt tcagtatgtg gaagaccccca ccatcgtgcg    3360
gattgagcca gaatggagca ttgtcagtgg aaacacaccc atcgccgtat gggggaccca     3420
cctggacctc atacagaacc cccagatccg tgccaagcat ggaggaagg agcacatcaa      3480
tatctgtgag gttctgaacg ctactgagat gacctgtcag gcgcccgccc tcgctctggg     3540
tcctgaccac cagtcagacc tgaccgagag gcccgaggag tttggcttca tcctggacaa     3600
cgtccagtcc ctgctcatcc tcaacaagac caacttcacc tactatccca acccggtgtt    3660
tgaggccttt ggtccctcag gaatcctgga gctcaagcct ggcacgccca tcatcctaaa    3720
gggcaagaac ctgatcccgc ctgtggctgg ggcaacgtg aagctgaact acactgtgct     3780
ggttggggag aagccgtgca ccgtgaccgt gtcagatgtc cagctgctct gcgagtcccc    3840
caacctcatc ggcaggcaca aagtgatggc ccgtgtcggt ggcatggagt actccccggg    3900
gatggtgtac attgccccgg acagcccgct cagcctgccc gccatcgtca gcatcgcagt    3960
ggctggcggc ctcctcatca ttttcatcgt ggccgtgctc attgcctata acgcaagtc     4020
ccgcgaaagt gacctcacgc tgaagcggct gcagatgcag atggacaacc tggagtcccg    4080
tgtggccctg gagtgcaagg aagccttgc cgagctgcag acggacatcc atgagctgac     4140
cagtgacctg gatggagccg ggattccgtt cctggactat agaacttaca ccatgcgggt    4200
gctgttccca ggaattgaag accaccctgt cctccgggac cttgaggtcc cgggctaccg    4260
gcaggagcgt gtggagaaag gcctgaagct cttcgcccag ctcatcaaca caaggtgtt    4320
cctgctgtcc ttcatccgca cgcttgagtc ccagcgtagc ttctccatgc gcgaccgtgg    4380
caacgtggcc tcactcatca tgaccgtgct gcagagcaag ctggagtacg ccactgatgt    4440
gctgaagcag ctgctggccg acctcattga caagaacctg agagcaaga accaccctaa    4500
gctgctgctc aggaggactg agtcagtggc tgagaagatg ctgaccaatt ggtttacttt    4560
cctcctctac aagttcctca aggagtgtgc tggggagccc ctcttctccc tgttctgtgc    4620
catcaagcag cagatggaga agggcccccat tgacgccatc acgggcgagg cccgctactc    4680
cttgagcgag gacaagctca tccgccagca gattgactac aaaaccctgg tcctgagctg    4740
tgtcagccca gacaatgcca acagccccga ggtcccagta aagatcctca actgtgacac    4800
catcactcag gtcaaggaga agattctgga tgccatcttc aagaatgtgc cttgctccca    4860
ccggcccaaa gctgcagata tggatctgga gtggcgacaa ggaagtgggg caaggatgat    4920
cttgcaggat gaagacatca ccaccaagat tgagaatgat tggaagcgac tgaacacact    4980
ggcccactac caggtgccag atggttccgt ggtggcatta gtgtccaagc aggtgacagc    5040
ctataacgca gtgaacaact ccaccgtctc caggacctca gcaagtaaat atgaaaacat    5100
gatccggtac acgggcagcc ccgacagcct ccgctcacgg acacctatga tcactcctga    5160
cctggagagt ggagtcaaga tgtggcacct agtgaagaac cacgagcacg agaccagaa     5220
ggagggggac cggggggagca agatggtgtc tgaaatctac ctgacccgac tcctggccac    5280
taagggcaca ctgcagaagt ttgtggatga cctcttgag accatcttca gcacggcaca    5340
ccgtggctct gccctgcccc tggccatcaa gtacatgttt gacttcctgg atgagcaggc    5400
```

```
tgataaacat ggcattcatg acccgcacgt ccgccatacc tggaagagca attgcctgcc   5460
cctgaggttt tgggtcaaca tgatcaagaa cccgcagttt gtgtttgaca tccataagaa   5520
cagcatcaca gacgcctgcc tctctgtggt ggctcagacc ttcatggact cttgctccac   5580
gtcagagcac cggctgggca aggactcgcc ctccaacaag ctgctgtatg ccaaggacat   5640
ccccagctac aagaattggg tggagaggta ttactcagac atagggaaga tgccagccat   5700
cagcgaccaa gacatgaacg catacctggc tgagcagtcc cggatgcaca tgaatgagtt   5760
caacaccatg agtgcactct cagagatctt ctcctatgtg ggcaaataca gcgaggagat   5820
ccttggacct ctggaccacg atgaccagtg tgggaagcag aaactggcct acaaactaga   5880
acaagtcata accctcatga gcttagacag ctgagaaccg tccttccagg gccgccctgg   5940 aggggggacac accaagccgt gcctcagtct agattatcat ctttaccaag tgcaagttcc   6000
gactggcatc agcagcatcc cctgagcagc gctgtttctc tctctttctc tctgcctctt   6060
tccgtttctc cctccttcct ggatctcttc tcttccagtt gctctgccaa cacgattgga   6120
ccaagccact gaccctcagt tagtccaaga atggccaggc ccatggcaag ggagctgacc   6180
agaagatgtc agagaggcct ctgtctccca ggtgctcctg accctgtgca tgtcagcagc   6240
agggtgcaaa taacgaatga ggagccaggg acaggggaca tttctgtgct gctacttcac   6300
cttccacttt ggcagcccct gctttggtct gagccttggc ctaggaagaa ggcaaggaag   6360
gacttcagta ttatctttac tgggaagaca tcacctggct ctcccttccc acagttccat   6420
ctccagtggt tcagccagtg gtctgatcgc tttgcagctg tgagaagaaa ggctacacct   6480
cctgcatgtg gctggagcag ggcatgtgtg ggcagctggg aggtgctcct tgaggctcct   6540
tctcccccac tgggctggtg tccagaggct cctgtccttt tccaggtct ccagagggac    6600 ctgcctgccc tgcctgctcc cccgccagta gaaagccagg caggagaaag aatagcaatt   6660
acattccacc atggagatgc tcctgacctt tcatctgaa tcctagtagc agaaatgtaa    6720
cacaggggga gaaaggaaa gagagttgca tctaccctgg aagcagaatt tgttttccat    6780
ttaccctcaa attcaaatga gtcacaatca tagtcatagg tctagtccac taccagagcc   6840
ctgagtgctg tcaagagaaa gcatctatct ccaccctcct ttgtcaacct tcatcaaggg   6900
tcaacgtgaa atgcagagtg catctaggag attctacctc cagccatctc catggctcca   6960
tccccatcat ccttcctgag aactccatag acggctgggg ccaacagcct agtccctgtt   7020
ccctctgcag aatccggtgc cattgctatg cagatgactt tgtcactggg ctgtccagac   7080
ctctttggga atgatttcat caacatctca gctgtctctc atcattctcc ttcctcatct   7140
cttcagcagt catccttgaa agaaacagac ttaagcaaag cctcacggag acagcccaaa   7200
atgccagcca acctcagcct ccagcttgtc agatctggga gggacaaaga gtcgagctga   7260
tgggcctggc tggaattaag aagagggaca tacaaatgac cttggccttg gcatccatct   7320
ccccatctgt tcttacatct acagatgcac gattttagcc aggcaggcaa atgtgtgcct   7380
agaaattgat actaggtaag cagaggctat ggggagagat ggtctaatgg agggttctag   7440 gaaccttca tcctaaggag accttaggtg ctgtctggtg cagtctccca tcctaagcag    7500
gagtctctgt tggcacctct gctctggagt tgttcaccac tatgggagac aaggagaaac   7560
atcttaggtg aggttgagga gaaggattca cagtcttgcc ttcactcccc aaacatcaga   7620
catcattcct tgtcacccac tcagaatgag ccccccttgg ggaagaaacc acaccatttc   7680
cagcaaagtc catggagcat ccggtacttt taagaacact tgccccttg gatatgaata    7740
```

```
tgtgcacatg tgtgtgagca catgtatgtg tgtgtgtgtg tctgccccag gtgtaggcgg    7800
aaagctcaaa aggatttctt gtcctttgta ggaggatttt tgaagtgttc cccttctctt    7860
tccccttgct catccattca tcctgcagct tcaggacatt tcaacactta cttgctttct    7920
atgctgagag ctggtgggtg gaaggagagg gcgcttgtcc ataggaaatc agggtggtcg    7980
cctgccgagg cctggacctt ggaacagggc atcatgtgac atcgcagagg acagatggtg    8040
gaaaagacat gagcaaccta atgggaagag gaaaatggga aacaatgcat tggaagagga    8100
agaaaaaaaa taaataacca aaggttttgg caagtgcagt accaggtgga gaagcttgac    8160
ttttctatcc ttgatcattt tattccctcc caagaagtca gtcacaggac ctggaaggcc    8220
agaaagggta catgtgggag acggtctgag gaagtacctc ggtcactaca atattttgc     8280 acatataaag ggttgggag  gaaagagaca caaacgtatt taacacagat ttgctggatg    8340
gaagctgcgt gtgtgaacgt gtgtatgagt gagtgcattt tgatttttt  tttttttttt    8400 tgcacagtta agagaaaaaa tcaaacaagc agaaaaaaaa aagaaaaaag acttatcacg    8460
gttctgctga agcttttatt ttttactgga tgatgattat tgttattgtt actttggcgg    8520
tacaggactt tattttattc catgttttg  ttataagaaa aatttcaaac acctcagaga    8580
aatagaaagg ttaggaagaa agaggagaca aggacagaca aattttctgg ctgtccccat    8640
ttctcctggg ggaggggttt ggggctggtt tgactttaat tggtgggtgg gttgtttctg    8700
ccgctctgtt tgctgcagtc cccgtggcct gcttggggac tgagaaattt gagccaggta    8760
tccagagcca cagcccatct tgcttataaa aattatcttc tgctgtttgt tttccatttc    8820
ttccgtttgg attcttggtg cacgtgtgat atggtattta aaagcaaaga caagcaacat    8880
tgtcaaaaag ctgtccttgc cccccatccc ccacccaaat cttttttcca aactccccca    8940
gggatcttcc ttaccccact ggcagagcaa acatccaggg gctgtccatg tggcttgcgg    9000
gctcccagag aaaggaattg ggccaacttt gtcctgtggg atggaggccc cttcacggcc    9060
tccctcgagg caaagttaat ttgtagggtc accattatgt tgagtcatga gcagacagaa    9120
ggagagaaaa ggccatcttc cttaccttcc cctccaactt atcccgtacc ctcccaggga    9180
aaatggtacc agactgagcc atcaaaatca ctgacaaagt ttaggtggga atttttttg     9240 catgttggag agagaagggc ttaaggtagc agggaagaag ggggctttgt ggggtcctaa    9300
attttaagga ataagtagag gaagacaaga aacagagtgg taggctggtc atttctcctg    9360
gccacaagtc cccccagatg cagctttta  ccattctttg tccttcccca taaggagaga    9420
ccctgacatt tcttggtagc tgcaaatagt gccactaagt gaaggtggcc atcatgccag    9480
ttacttcctc aggaaaatat tttcttgcct tcttctttca gtatggtttt aaatttggga    9540
acagtggata acccaagtgt cccacaggcc aaggtacatt ccaatggcag catgatccct    9600
gcacccaaag ccagccccta agcctaccc  cttgtgcacc cgcagcctgg taagtgagct    9660
tggctgcttg tgaggagcta caagtgaaag agaagttatt ttaaataaat cccaaagttt    9720
gaggcagact gtccaggact gttcccagga agaagcagga gttacccaca ggaaaagtct    9780
ctgacctggt cccctcaggc ccagctacct gcgcccacca gcagtgaagg ttgatgtact    9840
ggcccagcat ctccacctcc cccatgcaac caggtccctg gtaccgtgtc cccgttgca    9900 tgtctggctt ctgcctgtgc tcctcctgcc acgagcatcc tccctgtccc tcctcattcc    9960
accgtgtctc tcctgcacac atagcctctg tcccagggcg atttatccac ttgagtacag   10020
gagctgctca gacctctcag cccagccctc tgtgactgcc ccagcccat  cctacccac    10080 ccaaagctgc cttcctggct gtaggagctc cctcgtctag ccaaggccct atgggtcccc   10140
```

```
atccgaggat ccacaagcaa tgacttccca aatgacctcc actgcaagaa gaatccttac    10200
cactgtttcc agagccgtga acgatgctgt gatgggccca ggtctcagca ccaccctctg    10260
tgacctaaaa agaaaagctc aatttccatc tgtcttcttt cccaggacca aggggacaca    10320
gtaatgtgaa gtcaaatact taaccgagca aagggccagt attgttatca gtcaaggaca    10380
aacctcccac ctcacagaca gccaagcagt gagggaaaga cagacagaca taggtaggaa    10440
ggtgctctgc aggcacaagg cccagagaag cccctctccg ggaacttccc ctgctccttc    10500
caggaacagt gagcccagtg agcagcccca gccagctctt caaggccttc aaggggtctt    10560
tccatgactg agtcacctcc aggagctcac ctgaccccca gagaagacct accccaggca    10620
gctccgtgcc ctggcttctc cccatgcccc aaatccccc ccgccatccc tcctggtcct    10680
cgtctacatc aagggcctct tcccctcttc ctgccagctc tcaggacagg tgactgggag    10740
gccttgaacc ctcagcctct tcctttaaaa aaaacaaaac aaaacaaaac tgtgggccat    10800
ttatttggga ttttggagtt gtttggtttt tgtttgtata tcttaatagt tcgaaagtaa    10860
gaagggagcc ctgctatgga tgttaagtcc aaattactcg gttagtggga gcaaaaccta    10920
tgacttccaa ggggatgagg agaggttcag aggacaggag gagcctcccc cattgaaaaa    10980
aaaaaatggg tcaggacatt ccctggatga ggacaatgct aggggtggca tctcacatgg    11040
ctgctgctat tcctggtgct tccccacact tttgacagat ggagtccttc tcctaccgcc    11100
tcctgccacc tcaccctaca ggcattctct atgtaggaaa caagagcctt attttataga    11160
gtggggagct gagacacagc ctcaggtaac actgacacag ctcccgaatg aggctgggac    11220
actctgcaaa cctctcctca tggtgctaag ggtggcatgc tcttgacagg aaacctaaat    11280
gaccactcct ctcatttgga aagtaatcca ctgcagtaaa agtttcagac atgcaagaga    11340
gagttttttt ttttttacta caaattttg ctcccccata aaattatttt attagaggga    11400
gtatccaagt tttaaaagta tatagaattt tttggttgta agagaaatac atactcatta    11460
ggatcccgat taaattcctt gagtagactg gtgcctacca gaaagcaaag caaagttaaa    11520
caaaacgaaa caaaatcctt catatacaaa aagaactttc tgtttgtatt ggcagaggta    11580
gtgaggtgat tcaggtaggc tgaaaatcct gggttgcggg agcctcactt tattccattc    11640
ccacccgctt tgatgtctat gcttggctct ctgggctgcc cctggtactg ccgaatccta    11700
cacatctctt atcagctttc ctcaaacttt aaggaggctc tgtgagggat gggtcatggg    11760
aagacccaag ctttccctcc gccaggattg caaaagcaag tagacttggt ctatgcagct    11820
cttcttccag caatttcttt atttggaatt agaacttcct tgttagtat ctttgatctt    11880 ttgactcaag cacattttgg aagggctccc ttacaaaagt agaatttaaa acagaggata    11940
cagttaaaga gcaacccaaa ggacgcttaa gaaaccgaga ccacttcacc aaacaggact    12000
aaggaacact ttcgtgcaca gaagtcagcc gcaatccagg cacaggacga agatgggata    12060
cacgtgctca tctgtctgtc ctcctttcct ctccctcccc gacgttctag ttagcttgtt    12120
gacttgttaa accttctgtt cttaaaatga aaagctagct tacctcaaag aatcttgttt    12180
ccattcggaa accaacgatt ttgtgtttta gaatggacag ccctcccctc accactccct    12240
accttggcct ggtgtccttg agacatacgg tctttgctta gtcgtgtgtt ggctgctttg    12300
agcaggaaca aggcctccag gccctgaggt gggaaggaag gattggatgc cactgccctc    12360
ctccccactt tagcatgtag gggccagccc atctcttcca gcagggtcct gctgagttac    12420
catagcaacc agcaactcca gggtaccaca acagacaatg gctcagcgag ccgacgtgtg    12480
```

```
gggatgatgc agggggttttg gcccagccag aggacccaga gttgagcttc aaatgctaga   12540 gaagggaga  aacaggatgg  aagggtggtt  taaggaaccg  gcagggtct   ttgagtcaca   12600 tagagaagcc gttgaaggag gtagggcagg  ttatctctgt  tccagtcacc  cccttccagc   12660
cccatcccac ttctgtttca aactaaagct  cccacctcga  acattgaccc  tttgttagaa   12720
caaagcaaag catatcttta gacaacagtg  ttaaaatgag  cctcaaatgt  atgtggatga   12780
gatctctaag aagagggtct tctggttttg  atttttaaag  aagagtatcc  tagtaaaata   12840
ttaaaaaaaa attaaaaagt ttttaaaaag  gaaacctgtg  ctatttaaat  tggagcccag   12900
ttgtaacttg gtaaaggcaa gcttctgtac  ctttgttata  attaattgta  tacctgtgta   12960
tgtaaatata aggcattcct  attttgcagt  tcagaacaaa  aaaaacttat  ttgtaatata   13020
gaataaagtt tattaaaaaa taataaaaat  gcagtttggg  a                        13061
```

TREATMENT OF CHRONIC INFLAMMATORY RESPIRATORY DISORDERS

This application is a National Stage Application of International Application No. PCT/US2009/063584, filed Nov. 6, 2009, which claims priority to U.S. Provisional applications 61/111,767, filed Nov. 6, 2008, 61/143,488, filed Jan. 9, 2009, and 61/242,158, filed Sep. 14, 2009, all of which are incorporated by reference herein in their entireties.

This invention was made with government support under A1057400 awarded by the National Institutes of Health. The government has certain rights in the invention.

SEQUENCE LISTING

The instant application contains a Sequence Listing which has been submitted via EFS-Web and is hereby incorporated by reference in its entirety. Said ASCII copy, created on Nov. 5, 2009, is named 22402820.txt, and is 190,500 bytes in size.

BACKGROUND INFORMATION

Although chronic rhinosinusitis (CRS) is a widespread disease affecting ~15% of the US population, the pathogenesis is poorly understood. One of the most severe forms is CRS with hyperplastic sinonasal polyposis (CRSwNP). The presence of hyperplastic polyps in the sinuses is an ominous clinical feature signifying the presence of recalcitrant disease for which there is no known effective lasting treatment. Mucosal hyperplasia, a hallmark of the tissue remodeling observed in CRSwNP, results in chronic disease that becomes refractory to either medical or surgical management. Despite the significant morbidity of recurrent disease, central mechanisms regarding the pathogenesis of sinonasal polyposis remain poorly understood. Histological features of CRSwNP resemble that of asthmatic airways with endstage polyps displaying signs of Th2 inflammation characterized by infiltration with eosinophils, thickening of the basement membrane and hyperplasia of the epithelium and are strikingly reminiscent of the histopathology of severe asthmatic airways. Therefore, understanding factors controlling aberrant epithelial cell growth may provide critical insights into therapeutic strategies in the treatment of chronic rhinosinusitis with nasal polyposis, as well as asthma.

Despite the fact that epithelial hyperplasia is a key feature of sinonasal polyps, there is a surprising paucity of literature on studies of growth factors in the pathogenesis of epithelial hyperplasia in sinonasal polyps. Growth factors implicated in remodeling of asthmatic airways such as transforming growth factor β (TGFβ) and fibroblast growth factor (FGF) were found to be increased in nasal polyp tissue. Messenger RNA for TGFβ1 and FGF are increased in tissue homogenates of polyps. Immunohistochemical analysis localized TGFβ1 to the extracellular matrix and stroma of nasal polyps, where eosinophils reside. There have been many studies of other selected growth factors in nasal polyposis, such as insulin-like growth factor (IGF), FGF, PDGF, and TGF beta. However, the effects of TGF and FGF on sinus tissue remodeling have not been established. Epidermal growth factor (EGF) is thought to play a key role in epithelial proliferation, growth and repair in asthma. EGF receptor over expression on bronchial epithelial cells has been found to correlate with asthma severity and steroid refractoriness. However the role of EGF in development of sinonasal polyps has not been explored.

VEGF (vascular endothelial cell growth factor) as an endothelial cell mitogen has been implicated in the development of nasal polyps. Immunohistochemical analysis of nasal polyps from children showed increased VEGF staining within the vascular endothelium and increased mean blood vessel count both of which correlated with size of nasal polyps. Others have also shown that enhanced VEGF and its receptor expression were localized to the endothelium, the basement membranes, perivascular spaces, and epithelium of polyps. These studies indicate that the epithelium is a significant, but not necessarily the sole, source of VEGF in polyp tissue; but they do not show if the VEGF found in the epithelium was produced in those cells or whether it was actually generated by endothelial cells. Moreover, there have been no investigations to date on the role of VEGF as an epithelial mitogen in sinus disease.

DESCRIPTION OF THE DRAWINGS

FIG. 2A shows surgical sinonasal tissue from CRSwNP (right, n=5) and normal control sinus mucosa (left, n=5) that were immediately placed in 4% paraformaldehyde and processed for immunohistochemical staining of VEGF as described in Methods. Score shown in ( ) is the brown colored staining intensity expressed as mean intensity$\times 10^3$/cell +/−SEM determined using Image Pro software (Media Cybernetics, Silver Spring, Md.). Each inset represents the matching IgG control. Data are representative of n=5 subjects in each group and are shown at 10× magnification. $'p<0.012$ by Kruskal Wallis Test. FIG. 2B shows flow cytometric analysis of cell surface VEGF on cultured PNEC (primary nasal epithelial cells) from normal control and CRSwNP subjects. FIG. 2C shows soluble VEGF isoforms 165 and 121 in cell supernatents of PNEC, measured by ELISA according to manufacturers instructions (R&D). Lower limit of detection was 5 pg/ml. $*p<0.05$ and $**p<0.02$ vs Control subject by Kruskal Wallis Test.

FIG. 3A shows expression of VEGFR2, phospho-VEGFR2, and NP1 by epithelial cells in sinonasal tissue. Surgical sinonasal tissue from CRSwNP (n=5) and normal control sinus mucosa (n=5) were immediately placed in 4% paraformaldehyde and processed for immunohistochemical staining of VEGFR2, phospho-VEGFR2 and NP1, as described in Methods. Score shown in ( ) is the brown colored staining intensity expressed as mean$\times 10^3$ intensity/cell +/−SEM determined using Image Pro software (Macintosh). Data are shown at 10× magnification. FIG. 3B shows flow cytometric analysis of cell surface NP1 expression on PNEC from normal control and CRSwNP subjects. $*p<0.04$ vs control by Kruskal Wallis Test, n=6 for each group.

FIG. 4A shows a comparison of time to confluence of cultures of PNEC from normal control and CRSwNP subjects. PNEC from normal control and CRSwNP subjects were cultured as described in Methods. Results are expressed as # days to confluency of culture from day of seeding into 6 well plates and assessed in triplicate. FIG. 4B shows a comparison of cell proliferation rates of PNEC from normal control and CRSwNP subjects. Cell number was determined by normalization of DNA content to a standard curve using Cyquant cell proliferation assay as described in Methods. Each circle indicates an experiment from a single donor. Bars represent the mean. *$p<0.008$ or **$p<0.005$ vs control group by Kruskal Wallis Test.

FIG. 5A shows the effects of anti-VEGF antibody and recombinant EGF exposure on growth rates of PNEC from CRSwNP subjects. FIG. 5B shows the effects of anti-NP1, anti-VEGFR1 (vascular endothelial cell growth factor 1), and anti-VEGFR2 (vascular endothelial cell growth factor 2) antibody exposures on growth rates of PNEC from CRSwNP subjects. FIG. 5C shows the effects of combination of anti-NP1, anti-VEGFR1, and anti-VEGFR2 antibody exposures on growth rates of PNEC from CRSwNP subjects. PNEC from CRSwNP subjects were seeded at 5000 cells/well of a 96 well plate and exposed to designated blocking antibodies, recombinant EGF (R&D Systems) or IgG control antibody as described in Methods. Cell number was determined after normalization of DNA fluorescence to a standard curve using Cyquant cell proliferation assay as described in Methods. Each curve represents the mean of 5 experiments, each from an individual CRSwNP donor. Each condition and time point was measured in quadruplicate. SEM ranged between 12-27% of the mean. *$p<0.05$, or **$p<0.02$, vs Control condition at 96 hours by ANOVA and post hoc Bonferroni.

FIG. 6B shows light microscopic views of PNEC under 20× power. White arrows point to cell membrane blebs. *$p<0.001$, $p<0.02$, or *$p<0.05$ vs Control condition by ANOVA and post hoc Bonferroni Test.

FIG. 8A shows flow cytometric analysis of cell surface VEGF. Data represent the mean fluorescence intensity +/−SEM of n=4 experiments. *$p<0.05$ vs media control by ANOVA with post hoc Bonferroni Test. FIG. 8B shows fluorescent and matching light micrographs of PNEC transfected with rhodamine-tagged control siRNA. FIG. 8C shows realtime PCR analysis of NP1 mRNA. Panel FIG. 8D shows flow cytometric analysis of cell surface NP1. Data represent the mean+/−SEM of n=3 experiments. Analysis by ANOVA with post hoc Bonferroni Test resulted in $p<0.02$ for all 3 siRNA NP1 vs media control or negative control siRNA (siControl). *$p<0.05$ for siRNA 1 or siRNA 2 for NP1 vs media control. +$p<0.05$ for siRNA2 for NP1 vs negative control siRNA.

DESCRIPTION OF THE INVENTION

Figure 1:
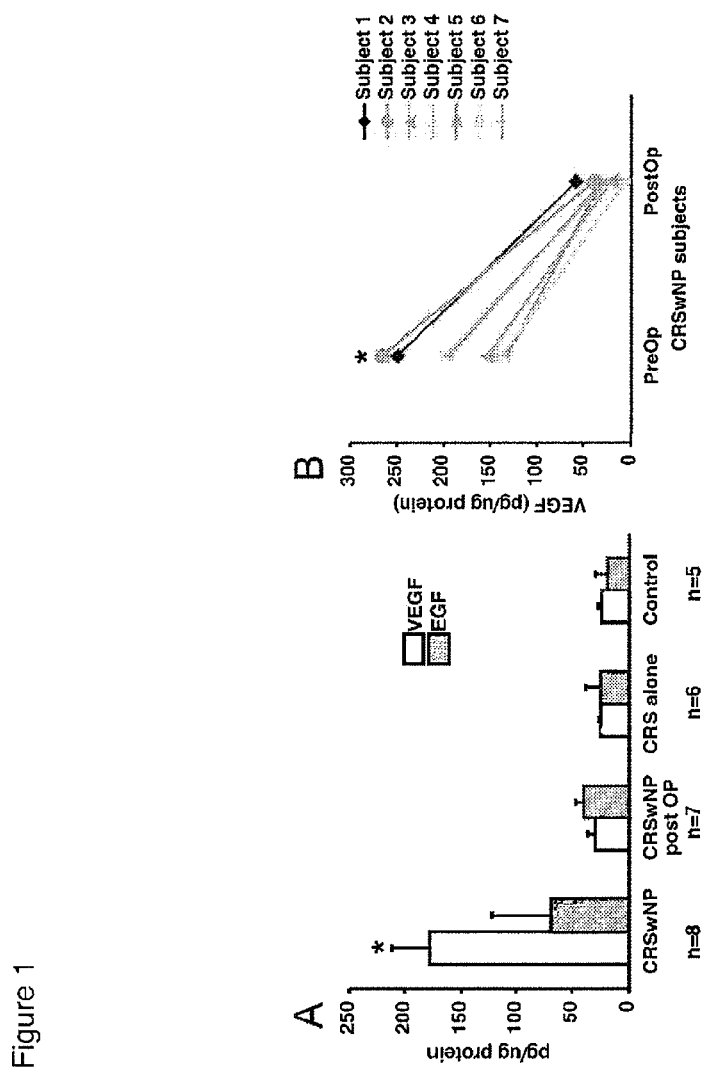
FIG. 1 shows a comparison of soluble growth factors in nasal lavages of untreated CRSwNP, CRSwNP patients at 1 month post-operatively, CRS alone, and normal control subjects. VEGF and EGF in nasal lavages were assayed according to manufacturer's instruction (antibodies and kits from R&D Systems). The lower limit of detection was 5 pg/ml. Values represent the mean+/−SEM. $p<0.001$ vs Control, CRS alone, or CRSwNP post-op subjects by Kruskal Wallis Test. Human subjects data is shown in Table 1.

The present inventors demonstrate herein that VEGF is a central pathway by which airway epithelial cell growth is regulated. To demonstrate this, they used the following in vivo and in vitro human experimental models: (1) nasal lavage aspirates, (2) surgical sinonasal tissue, and (3) cultured primary nasal airway epithelial cells. The identification of VEGF-A; the VEGF-A receptors, VEGF receptor 1 (VEGFR1) and VEGF receptor 2 (VEGFR2); and VEGF-A co-receptor, neuropilin-1 (NP1), as targets for the treatment of chronic inflammatory respiratory disorders provides the basis for new types of treatments for this class of disorders.

One aspect of the invention is a method for inhibiting the proliferation of epithelial cells, comprising contacting the cells with an effective amount of an inhibitor of the expression of and/or of the activity of VEGF-A, and/or VEGFR1, and/or VEGFR2, and/or NP1. Furthermore, other, related members of the VEGF-A family, such as the VEGF isoforms (splice variants), VEGF 165, VEGF 121, or VEGF 189, or the homologs, VEGF-B, VEGF-C, VEGF-D, or P/GF (placental growth factor), can serve as targets. In addition, it is expected that VEGFR3 and NP2, which are known to interact with some of the molecules noted above, can also serve as targets. Furthermore, NP1 is known to engage other ligands or co-receptors, which are also expected to be involved in the proliferation of epithelial cells and which can thus be inhibited by a method of the invention. These additional proteins include, e.g., Plexin A1, A2, A3 or A4, integrin beta-1, TGF beta-1, FGF2, FGF4, HGF and galectin-1.

The epithelial cells whose growth is inhibited by a method of the invention can be in vitro, in cell culture. These cells can be primary cell cultures, or cells from an established cell line (e.g., BEAS2B, A549 or 16HBE cells, all of which are available from the American Type Culture Collection, Manassas, Va.). Alternatively, the epithelial cells whose growth (hyperplasia) is inhibited can be in vivo, in a subject (e.g., a subject having a chronic inflammatory respiratory disorder). One embodiment of this latter method is a method for treating a subject having a chronic inflammatory respiratory disorder, or for preventing the development of such a disorder, comprising administering to the subject an effective amount of an inhibitor of the expression of, and/or of the activity of, VEGF-A, and/or VEGFR1, and/or VEGFR2, and/or NP1, and/or one of the other ligands, receptors, or co-receptors noted above, and/or combinations thereof. Such inhibitors or combinations of inhibitors are sometimes referred to herein as "inhibitors of the invention."

Among the types of chronic inflammatory respiratory disorder that can be treated by a method of the invention are, e.g., chronic rhinosinusitis with nasal polyposis (CRSwNP), chronic rhinosinusitis without nasal polyposis, asthma (in adults or a pediatric population), chronic obstructive pulmonary disease (COPD), allergic and/or nonallergic rhinitis, or allergic bronchopulmonary aspergillosis, or cystic fibrosis. All of these disorders are airway inflammatory disorders, for which dysfunctional airway epithelial cells are central. A method of the invention targets these disturbed epithelial cells. At least some of these conditions, including asthma, exhibit a histological appearance and behavior (recurrences and exacerbations) that are identical to that of CRSwNP. It is expected that cystic fibrosis, another airway inflammatory disorder, can also be treated by a method of the invention.

An inhibitor of the invention can be, e.g., an antibody or antibody fragment, an inhibitory RNA (siRNA, microRNA, etc), a small molecule, a peptide, or the like.

In one embodiment of the invention, the inhibitor comprises an antibody (e.g., a blocking antibody) against VEGF, NP-1, VEGFR1, VEGFR2, or combinations thereof. In other embodiments, the inhibitor comprises a blocking antibody against other combinations of the proteins noted above. For example, the inhibitor can comprise a blocking antibody against:

1) VEGF-A in combination with one or more of VEGFR1, VEGFR2 and VEGFR3,
(2) NP1 in combination with one of more of VEGFR1, VEGFR2, VEGFR3, integrin beta-1, TGF beta-1, FGF2, FGF4, hepatocyte growth factor/scatter factor, and galectin-1,
(3) NP2 in combination with one or more of VEGFR1, VEGFR2, VEGFR3, integrin beta-1, TGF beta-1, FGF2, FGF4, hepatocyte growth factor/scatter factor, and galectin-1,
(4) NP1 in combination with VEGF-A,
(5) NP2 in combination with VEGF-A, or
(6) VEGF-A, (NP1 or NP2), and (VEGFR1 or VEGFR2),
(7) NP1, or
(8) VEGF-A.

As used herein, the singular forms "a," "an," and "the" include plural referents unless the context clearly dictates otherwise. For example, "an" anti-VEGF blocking antibody, as used above, means one or more anti-VEGF blocking antibodies, which can be the same or different.

In another embodiment, the inhibitor is an RNA aptamer, such as pegaptanib; a partial or full-length antibody, such as ranibizumab or bevacizumab; a VEGF receptor decoy, such as VEGF Trap (see, e.g., U.S. Pat. No. 7,541,172); small interfering RNA-based therapies, such as a microRNA or an siRNA, including the siRNAs described herein, microRNAs, bevasiranib, or AGN211745; a tyrosine kinase inhibitor, such as vatalanib, pazopanib, TG100801, TG101095, AG013958 or AL39324; a small molecule, or a blocking peptide. For example, one can use a blocking peptide against the VEGF receptors NP1 and/or VEGFR2, such as those described in Barr et al. (2005) *Br J Cancer* 92, 328-333.

An inhibitor of the invention can be administered by, e.g., systemic intravenous (IV) or by an intranasal route.

Another aspect of the invention is a method for screening for agents that can be used to treat a chronic inflammatory respiratory disorder. In one embodiment of the invention, the method comprises screening putative inhibitory agents for their ability to inhibit the growth of suitable epithelial cells in culture (such as cultured primary nasal epithelial cells (PNEC), primary bronchial epithelial cells (PBEC), or suitable established cell lines, such as BEAS2B, A549 or 16HBE cells). Cell growth can be assayed by any of a variety of methods, including, e.g., using Cyqyant dye or BUdR. In another embodiment, putative inhibitory agents are screened for their ability to induce apoptosis of such epithelial cells. Apoptosis can be measured by any of a variety of methods, including, e.g., flow cytometric analysis of annexin. In another embodiment, putative inhibitory agents are screened for their ability to inhibit autocrine VEGF in the supernatant of such cells, e.g. using an ELISA assay. In another embodiment, putative inhibitory agents are tested for their ability to inhibit cell growth or cell survival of whole intact diseased sinus polyps ex vivo, using quantitative immunohistochemical PCNA staining or TUNEL staining, respectively.

Another aspect of the invention is a kit for treating a subject having a chronic inflammatory respiratory disorder, or for preventing the development of such a condition, comprising a) an effective amount of an inhibitor of the expression of, and/or the activity of, VEGF-A, and/or VEGFR1, and/or VEGFR2, and/or NP1 (or other combinations of proteins as discussed above); and b) reagents or devices for introducing the inhibitor into the airway of the subject, e.g., by an intranasal route. For example, the kit can comprise applicators that are suitable for administering the agent as a nasal spray or as a topical lavage (nasal wash solution, for bathing the sinuses and nose with the agent).

The Examples herein are directed primarily to VEGF-A (which is sometimes referred to as VEGF). However, it will be clear to a skilled worker that a variety of other targets are implicated by the experiments presented herein, including VEGF-C, VEGF-D or P/GF (placental growth factor). There is a great deal of redundancy in the VEGF gene family and in the VEGF receptor gene families. For example, VEGFR1 and VEGFR2 are each mitogens for endothelial cells, but in different organ systems, VEGFR1 is mostly involved in promoting lymphangiogenesis, while VEGFR2 is mostly involved in vascular angiogenesis. There is also some overlap in the activities of these receptors. It will be understood by a skilled worker that references to "VEGF-A" or "VEGF receptors" herein include a variety of other, related targets. Some of these targets are listed in Table 2.

A "VEGF-A receptor," as used herein, is a receptor which VEGF-A binds to and subsequently activates. Such receptors include, e.g., NP-1, VEGFR1 (Flt-1) and VEGFR2 (Flk-1/KDR).

Sequences of some of the targets that can be used in a method of the invention, and their GenBank accession numbers, are provided in the Sequence Listing attached to this application. These include the genes listed in Table 1. The GenBank numbers refer to the nucleic acid sequences. The sequences of proteins encoding by these nucleic acids will be evident to a skilled worker.

TABLE 2

| Name of Target Gene | Acronym | Gene Bank # | SEQ ID NO: |
|---|---|---|---|
| | VEGF-A | NM_001025366.1 | 13 |
| | VEGF B | NM_003377.3 | 14 |
| | VEGF C | NM_005429.2 | 15 |
| | VEGF D | NM_004469.2 | 16 |
| Placental Growth Factor | PIGF | NM_002632.4 | 17 |
| Neuropilin-1 | NP1 | NM_003873.5 | 27 |
| Neuropilin-2 | NP2 | NM_201266.1 | 28 |
| VEGF Receptor 1 | VEGFR1 | NM_002019.4 | 29 |
| VEGF Receptor 2 | VEGFR2 | NM_002253.2 | 30 |
| VEGF Receptor 3 | VEGFR3 | NM_002020.4 | 31 |
| Semaphorin 3A | Sema 3A | NM_006080.2 | 18 |
| Semaphorin 3C | Sema 3C | NM_006379.2 | 19 |
| Semaphorin 3F | Sema 3F | NM_004186.3 | 20 |
| integrin beta-1 | integrin beta-1 | NM_002211.3 | 21 |
| transforming growth factor beta-1 | TGF beta-1 | NM_000660.4 | 22 |
| fibroblast growth factor 2 | FGF2 | NM_002006.4 | 23 |
| fibroblast growth factor 4 | FGF4 | NM_002007.2 | 24 |
| hepatocyte growth factor/scatter factor | HGF | NM_000601.4 | 25 |
| galectin-1 | galectin-1 | NM_001009287.1 | 26 |
| plexin A1 | PLXNA1 | NM_032242.3 | 32 |

TABLE 2-continued

| Name of Target Gene | Acronym | Gene Bank # | SEQ ID NO: |
|---|---|---|---|
| plexin A2 | PLXNA2 | NM_025179.3 | 33 |
| plexin A3 | PLXNA3 | NM_017514.3 | 34 |
| plexin A4 | PLXNA4 | NM_020911.1 | 35 |

A "subject," as used herein, can refer to any animal which is subject to a chronic inflammatory respiratory disorder, e.g., a mammal, such as an experimental animal, a farm animal, pet, or the like. In some embodiments, the animal is a primate, preferably a human.

An "effective amount" of an inhibitor of the invention is an amount that is effective to elicit a measurable amount of biological activity, e.g. a measurable amount of suppression or inhibition of VEGF-A mediated proliferation of epithelial cells, or inhibition of a chronic inflammatory respiratory disorder. Preferably, an effective amount of an inhibitor of the invention does not elicit substantial amounts of undesirable (e.g., toxic) effects. The suppression or inhibition can occur prophylactically (e.g., preventively, to inhibit the development of the disorder), or in a subject who already has the condition. For example, treatment with an inhibitor of the invention can ameliorate one or more symptoms of the condition.

Any of a variety of types of agents can be used to inhibit the expression or activity of, e.g., VEGF-A or a VEGF-A receptor in a method of the invention. An "inhibitor" of expression or activity is an agent that reduces the expression or activity by a detectable amount.

Methods for making and using inhibitors of the invention are conventional and well-known in the art. Guidance in performing some of the methods of the invention is provided, for example, in Sambrook et al., Molecular Cloning, A Laboratory Manual (volumes Cold Spring Harbor Laboratory Press, USA or Harlowe and Lane, Antibodies a Laboratory Manual 1988 and 1998, Cold Spring Harbor Laboratory Press, USA. These and other references cited herein which provide guidance for performing methods related to the present invention are incorporated by reference herein in their entirety.

In one embodiment of the invention, the inhibitory agent inhibits the expression of VEGF-A or a VEGF-A receptor. The term "expression" of a gene, as used herein, refers to any aspect of the process by which information in a gene is converted to a functional molecule, e.g., any aspect of transcription or translation of the gene. For example, "expression" can refer to transcription, post-transcriptional processing, translation, or post-translational processing. Examples of inhibitors of expression include an antisense nucleic acid, a ribozyme, a microRNA, or a small interfering RNA (siRNA), which is specific for a nucleic acid encoding VEGF-A or a VEGF-A receptor. By "specific for" VEGF-A or a VEGF-A receptor is meant that the agent preferentially inhibits the expression of VEGF-A or a VEGF-A receptor, compared to the expression of other proteins. An agent that is specific for a particular sequence can bind preferentially to that sequence, under conventional conditions of high stringency.

In one embodiment, the inhibitor is an antisense nucleic acid which comprises a single-stranded polynucleotide that is specific for a sequence encoding VEGF-A or a VEGF-A receptor, or a portion of one of those sequences. The nucleic acid sequences encoding VEGF-A and its receptors are well-known in the art. For example, one can access sequences encoding these proteins in publically available databases, such as the GenBank database operated by the NCBI. The GenBank accession numbers and sequences for some suitable targets are presented in Table 2 and in the Sequence Listing herein.

Each of these accession numbers, in conjunction with the names and unique gene symbols of the genes, is adequate to unambiguously identify these genes. Furthermore, the sequence (and the corresponding SEQ ID number) of a nucleic acid corresponding to each marker (e.g., a transcribed RNA, a cDNA or a genomic sequence) is also provided. The sequences were obtained from the GenBank database (at the world wide web site ncbi.nlm.nih.gov/Genbank), and the GenBank Accession Numbers (e.g., NM_ numbers) are provided in Table 2 and in the Sequence Listing. Note that the sequences that are presented herein are correct as of the day of filing of this application. However, in GenBank, sequences are periodically updated by the NCBI to correct errors. As the sequences are curated, and new sequences replace previous sequences that contained errors, the replacement is described in the COMMENT section of the GenBank entry. Sequences that are subsequently corrected are encompassed by the present application. At any given time, only a single sequence is associated with each GenBank Accession Number. There is no indefiniteness, variability or uncertainty as to the sequence that is associated with any particular accession number at the time this application was filed. The sequences, and the GenBank accession numbers with which they are associated, are hereby incorporated by reference.

A skilled worker would be able to design, make and use suitable antisense molecules, based on these or other sequences, without undue experimentation. The antisense nucleic acid may be, e.g., an oligonucleotide, or a nucleic acid comprising an antisense sequence that is operably linked to an expression control sequence, and that is expressed in the cell.

The use of antisense nucleic acids to downregulate the expression of a particular protein in a cell is well known in the art. See, e.g., Weintraub et at (1986) *Reviews—Trends in Genetics* 1(1); Askari et al. (1996) *N. Eng. J. Med.* 334, 316-318; Bennett et al. (1995) *Circulation* 92, 1981-1993; Mercola et al. (1995) *Cancer Gene Ther.* 2, 47-59; Rossi et al. (1995) *Br. Med. Bull.* 51, 217-225; or Wagner, R. W. (1994) *Nature* 372, 333-335. An antisense nucleic acid molecule may comprise a nucleotide sequence that is complementary to the coding strand of another nucleic acid molecule (e.g., an mRNA sequence), or to a portion thereof, and accordingly is capable of hydrogen bonding to the coding strand of the other nucleic acid molecule. Alternatively, antisense sequences can be complementary to a sequence found in the 5' or 3' untranslated region of the mRNA or a region bridging the coding region and an untranslated region (e.g., at the junction of the 5' untranslated region and the coding region). The antisense nucleic acid can be complementary in sequence to a regulatory region of the gene encoding the mRNA, for instance a transcription initiation sequence or regulatory element, or a splice site. In one embodiment, an antisense nucleic acid is designed so as to be complementary to a region preceding or spanning the initiation codon on the coding strand or in the 3' untranslated region of an mRNA. An antisense nucleic acid for inhibiting the expression of a protein of interest in a cell can be designed based upon the nucleotide sequence encoding the protein or upon sequences regulating its transcription or translation, constructed according to the rules of Watson and Crick base pairing.

For guidance in constructing antisense molecules that are complementary to a region of a gene involved in transcription (thereby blocking transcription and/or the production of isoforms, such as splice variants), see, e.g., Lee et al. (1979)

Nucl. Acids Res. 6, 3073; Cooney et al. (1988) *Science* 241, 456; and Dervan et al. (1991) *Science* 251, 1360. For further guidance on administering and designing antisense, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708.

An antisense nucleic acid can exist in a variety of different forms. For example, it can be DNA, RNA, PNA or LNA, or chimeric mixtures or derivatives or modified versions thereof, single-stranded or double-stranded. The nucleic acid can be modified at the base moiety, sugar moiety, or phosphate backbone, using conventional procedures and modifications. Modifications of the bases include, e.g., methylated versions of purines or pyrimidines. Modifications may include other appending groups such as peptides, or agents facilitating transport across the cell membrane (see, e.g. Letsinger et al., 1989, *Proc. Natl. Acad. Sci. USA* 84:684-652; PCT Publication WO 88/09810 (1988), hybridization-triggered cleavage agents (e.g. Krol et al., 1988, *BioTechniques* 6:958-976) or intercalating agents (e.g., Zon, 1988, *Pharm. Res* 5:539-549).

Antisense nucleic acids (e.g., oligonucleotides) can be constructed using chemical synthesis procedures known in the art. Such an antisense nucleic acid can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. To inhibit expression of VEGF-A or a VEGF-A receptor in cells in culture, such antisense nucleic acids can be added to cells in culture media. Typically, synthetic oligonucleotides are added to a final concentration of about 10 nM to about 1000 nM, preferably about 50 nM to about 200 nM (e.g., about 200 µg oligonucleotide/ml).

Alternatively, an antisense nucleic acid can be produced biologically using an expression vector into which a nucleic acid has been subcloned in an antisense orientation (i.e., nucleic acid transcribed from the inserted nucleic acid will be of an antisense orientation to a target nucleic acid of interest). Expression control sequences (e.g., regulatory sequences) operatively linked to a nucleic acid cloned in the antisense orientation can be chosen which direct the expression of the antisense RNA molecule in a cell of interest. For instance, promoters and/or enhancers or other regulatory sequences can be chosen which direct constitutive, tissue specific or inducible expression of antisense RNA. Inducible expression of antisense RNA, regulated by an inducible eukaryotic regulatory system, such as the Tet system (e.g., as described in Gossen et al. (1992) *Proc. Natl. Acad. Sci. USA* 89, 5547-5551; Gossen et al. (1995) *Science* 268, 1766-1769; PCT Publication No. WO 94/29442; and PCT Publication No. WO 96/01313) can be used. The antisense expression vector can be in the form of, for example, a recombinant plasmid, phagemid or attenuated virus. The antisense expression vector can be introduced into cells using standard techniques well known in the art. An antisense molecule of the invention can be complementary to any portion of a VEGF-A or VEGF-A receptor encoding or regulatory sequence.

In another embodiment, an inhibitory agent of the invention is a ribozyme. Ribozymes are catalytic RNA molecules with ribonuclease activity which are capable of cleaving a single-stranded nucleic acid, such as an mRNA, to which they have a complementary region. For reviews on ribozymes see e.g., Ohkawa et al. (1995) *J. Biochem.* 118, 251-258; Sigurdsson et al. (1995) *Trends Biotechnol.* 13, 286-289; Rossi, J. J. (1995) *Trends Biotechnol.* 13, 301-306; Kiehntopf et al. (1995) *J. Mol. Med.* 73, 65-71). A ribozyme having specificity for an mRNA of interest can be designed based upon the nucleotide sequence of, e.g., the corresponding cDNA. For example, a derivative of a Tetrahymena L-19 IVS RNA can be constructed in which the base sequence of the active site is complementary to the base sequence to be cleaved in a VEGF-A or VEGF-A receptor mRNA. See for example U.S. Pat. Nos. 4,987,071 and 5,116,742, both by Cech et al. Alternatively, human VEGR-A or a VEGF-A receptor mRNA can be used to select a catalytic RNA having a specific ribonuclease activity from a pool of RNA molecules. See for example Bartel et al. (1993) *Science* 261, 1411-1418.

In another embodiment, the inhibitor is an siNA (a double-stranded nucleic acid, preferably an RNA, which is sometimes referred to as a small or short, interfering or inhibitory, nucleic acid. When the nucleic acid is an RNA, the molecule is sometimes referred to as an siRNA), used in a method of RNA interference to interfere with protein expression, and directed to VEGF-A, NP-1, VEGFR1, VEGFR2, or combinations thereof. Based on the well-known sequences of nucleic acids encoding these proteins, a skilled worker would be able to design, make and use any of a variety of suitable siNAs (e.g., siRNAs), based on these sequences, without undue experimentation. For example, the siRNA can comprise a single-stranded polynucleotide represented by one of the following sequences that are described in the Examples herein: CCACAUUUCACAAGAAGAUUGUGCA (SEQ ID NO:1), UGCACAAUCUUCUUGUGAAAUGUGG (SEQ ID NO:2), GCCAGGAUA CGAAGGUGAAGGAGAA (SEQ ID NO:3), UUCUCCUUCACCUUCGUAUCCUGGC (SEQ ID NO:4), UCUGUCGCUACGACCGGCUAGAAAU (SEQ ID NO:5), or AUUUCUA GCCGGUCGUAGCGA-CAGA (SEQ ID NO:6), or an active variant thereof, or a complement of the sequence or of the active variant.

An "active" fragment or variant, as used herein, refers to a fragment or variant of one of the preceding nucleic acids (SEQ ID NOs 1-6) which retains at least one activity of that nucleic acid (e.g., the ability to suppress the expression of VEGF-A or a VEGF-A receptor, and/or to inhibit a chronic inflammatory respiratory disorder). For example, nucleic acids comprising small substitutions, additions, deletions, etc, are tolerated provided they retain such an activity, Nucleic acids that exhibit at least about 90% (e.g., at least about 95%, or at least about 98%) sequence identity to a nucleic acid of interest, or to an active fragment thereof, are also included. Methods for determining if a nucleic acid exhibits a particular percent identity to a nucleic acid are conventional. A "complement" of a nucleic acid, as used herein, refers to a complete complement.

As used herein, the term siNA is meant to be equivalent to other terms used to describe nucleic acid molecules that are capable of mediating sequence specific RNAi (RNA interference), for example short (or small) interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing, and others. Long double-stranded interfering RNAs, such as miRNAs, appear to tolerate mismatches more readily than do short double-stranded RNAs. In addition, as used herein, the term RNAi is meant to be equivalent to other terms used to describe sequence-specific RNA interference, such as post-transcriptional gene silencing, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, for example, Allshire (2002) *Science* 297, 1818-1819; Volpe et al. (2002) *Science* 297, 1833-1837; Jenuwein (2002) *Science* 297, 2215-2218; and Hall et al. (2002) *Science* 297, 2232-2237.)

An siNA can be designed to target any region of the coding or non-coding sequence of a gene. An siNA is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region has a nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary. The siNA can be assembled from a single oligonucleotide, where the self-complementary sense and antisense regions of the siNA are linked by means of a nucleic acid based or non-nucleic acid-based linker(s). The siNA can be a polynucleotide with a hairpin secondary structure, having self-complementary sense and antisense regions. The siNA can be a circular single-stranded polynucleotide having two or more loop structures and a stem comprising self-complementary sense and antisense regions, wherein the circular polynucleotide can be processed either in vivo or in vitro to generate an active siNA molecule capable of mediating RNAi. The siNA can also comprise a single-stranded polynucleotide having nucleotide sequence complementary to nucleotide sequence in a target nucleic acid molecule or a portion thereof (or can be an siNA molecule that does not require the presence within the siNA molecule of nucleotide sequence corresponding to the target nucleic acid sequence or a portion thereof), wherein the single-stranded polynucleotide can further comprise a terminal phosphate group, such as a 5'-phosphate (see for example Martinez et al. (2002) *Cell* 110, 563-574 and Schwarz et al. (2002) *Molecular Cell* 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. In certain embodiments, short interfering nucleic acids do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." Other chemical modifications, e.g., as described in PCT/US03/05346 and PCT/US03/05028, can be applied to any siNA sequence of the invention.

Preferably an RNA interference molecule has a 2 nucleotide 3' overhang. If the RNA interference molecule is expressed in a cell from a construct, for example from a hairpin molecule or from an inverted repeat of the desired VEGF-A or VEGF-A receptor sequence, then the endogenous cellular machinery will create the overhangs.

Considerations to be taken into account when designing an RNAi molecule include, e.g., the sequence to be targeted, secondary structure of the RNA target and binding of RNA binding proteins. Methods of optimizing siRNA sequences will be evident to the skilled worker. Typical methods are described, e.g., in Vickers et al. (2003) *J Biol Chem* 278, 7108-7118 and Yang et al. (2003) *Proc Natl Acad Sci USA* 99, 9942-9947.

Methods of making siNAs (e.g., siRNAs) are conventional and will be evident to the skilled worker. In vitro methods include, e.g., processing the VEGF-A or VEGF-A receptor ribopolynucleotide sequence in a cell-free system (e.g., digesting long double-stranded RNAs with RNAse III or Dicer), transcribing recombinant double-stranded VEGF-A or VEGF-A receptor DNA in vitro, and chemical synthesis of nucleotide sequences homologous to a VEGF-A or VEGF-A receptor sequence. See, e.g., Tuschl et al. (1999) *Genes & Dev.* 13, 3191-3197. In vivo methods include, e.g., (1) transfecting DNA vectors into a cell such that a substrate is converted into siRNA in vivo [see, e.g., Kawasaki et al. (2003) *Nucleic Acids Res* 31, 700-707; Miyagishi et al. (2003) *Nature Biotechnol* 20, 497-500; Lee et al. (2002) *Nature Biotechnol* 20, 500-505, Brummelkamp et al. (2002) *Science* 296, 550-553; McManus et al. (2002) *RNA* 8, 842-850; Paddison et al. (2002a) *Gene Dev* 16, 948-958; Paddison et al. (2002b) *Proc Natl Acad Sci USA* 99, 1443-1448); Paul et al. (2002) *Nature Biotechnol* 20, 505-508; Sui et al. (2002) *Proc Natl Acad Sci USA* 99, 5515-5520; Yu et al. (2002) *Proc Natl Acad Sci USA* 99, 6047-6052]; (2) expressing short hairpin RNAs from plasmid systems using RNA polymerase III (pol III) promoters [see, e.g., Kawasaki et al. (2003) (supra), Miyagishi et al. (2003) (supra), Lee et al. (2002) (supra), Brummelkamp et al. (2002) (supra), McManus et al. (2002) (supra), Paddison et al. (2002a) (supra), Paddison et al. (2002b) (supra), Paul et al. (2002) (supra), Sui et al. (2002) (supra) and Yu et al. (2002) (supra)]; and/or (3) expressing short RNA from tandem promoters [see, e.g., Miyagishi et al. (2003) (supra) and Lee et al. (2002) (supra)].

When synthesized in vitro, a typical 0.2 micromolar-scale RNA synthesis provides about 1 milligram of siRNA, which is sufficient for about 1000 transfection experiments using a 24-well tissue culture plate format. In general, to inhibit VEGF-A or VEGF-A receptor expression in cells in culture, one or more siRNAs can be added to cells in culture media, typically to a final concentration of about 50-200 μg, preferably about 50 μg siRNA/ml.

Any of a variety of conventional methods can be used to introduce siNAs into cells, including transfection, electroporation, or other methods known in the art. See, e.g., Hannon (2002) *Nature* 418, 244-251; Bernstein et al. (2002) *RNA* 7, 1509-1521; Hutvagner et al., *Curr. Opin. Genetics & Development* 12, 225-232; Brummelkamp (2002) *Science* 296, 550-553; Lee et al. (2002) *Nature Biotechnol* 20, 500-505; Miyagishi et al. (2002) *Nature Biotechnol.* 20, 497-500; Paddison et al. (2002) *Genes & Dev* 16, 948-958; Paul et al. (2002) *Nature Biotechnol.* 20, 505-508; Sui et al. (2002) *Proc. Natl. Acad. Sci. USA* 99, 5515-5520; and Yu et al.

(2002) *Proc. Natl. Acad. Sci. USA* 99, 6047-6052. Nanoparticle methods such as those described by Schiffelers et al. (2004) *Nucleic Acid Res.* 32:e149 and fusion protein methods such as described by Song et al. (2005) *Nature Biotechnol.* 23:709-717 are also useful.

For further guidance concerning inhibitory RNAs, see e.g., Lau et al. (2003) *Scientific American*, pp. 34-41; McManus et al. (2002) *Nature Reviews Genetics* 3, 737-747; and Dykxhoorn et al. (2003) *Nature Reviews Molecular Cell Biology* 4, 457-467. For further guidance regarding methods of designing and preparing siRNAs, testing them for efficacy, and using them in methods of RNA interference (both in vitro and in vivo), see, e.g., Allshire (2002) *Science* 297, 1818-1819; Volpe et al. (2002) *Science* 297, 1833-1837; Jenuwein (2002) *Science* 297, 2215-2218; Hall et al. (2002) *Science* 297, 2232-2237; Hutvagner et al. (2002) *Science* 297, 2056-60; McManus et al. (2002) *RNA* 8, 842-850; Reinhart et al. (2002) *Gene & Dev.* 16, 1616-1626; Reinhart et al. (2002) *Science* 297, 1831; Fire et al. (1998) *Nature* 391, 806-811, Moss (2001) *Curr Biol* 11, R772-5, Brummelkamp et al. (2002) *Science* 296, 550-3; Bass (2001) *Nature* 411 428-429; and Elbashir et al. (2001) *Nature* 411, 494-498; U.S. Pat. No. 6,506,559; US patent application 20030206887; and PCT applications WO99/07409, WO99/32619, WO 00/01846, WO 00/44914, WO00/44895, WO01/29058, WO01/36646, WO01/75164, WO01/92513, WO 01/29058, WO01/89304, WO01/90401, WO02/16620, and WO02/29858.

Ribozymes and siRNAs can take any of the forms, including modified versions, described above for antisense nucleic acid molecules.

In one embodiment, an interfering nucleic acid is a double-stranded RNA (e.g., an siRNA), one of whose strands comprises (or consists essentially of) one of the sequences represented by SEQ ID NOS:1-6, or an active variant thereof, or a complement of one of those sequences.

Active variants (e.g., length variants, including fragments; and sequence variants) of the nucleic acid-based inhibitors discussed above are included in the invention. An "active" variant is one that retains a measurable amount of an activity (such as the ability to inhibit expression) of the inhibitor from which it is derived.

With regard to length variants, an antisense nucleic acid or siRNA may be of any length that is effective for inhibition of a gene of interest. Typically, an antisense nucleic acid is between about 6 and about 50 nucleotides (e.g., between about 10 and 30 nucleotides, or at least about 12, 15, 20, 25, 30, 35, 40, 45 or 50 nt), and may be as large as about 100 to about 200 nucleotides, or larger. Antisense nucleic acids having about the same length as the gene or coding sequence to be inhibited may be used. The length of an effective siRNA is generally between about 19 bp and about 29 bp in length, (e.g., about 19, 21, 23, 25, 27 or 29 bp), with shorter and longer sequences being acceptable. Generally, siRNAs are shorter than about 30 bp, to prevent eliciting interferon effects. For example, an active variant of an siRNA having, for one of its strands, the sequence of SEQ ID NO:1, SEQ ID NO:2, SEQ ID NO:3, SEQ ID NO:4, SEQ ID NO:5 or SEQ ID NO:6 can lack base pairs from either, or both, of the ends of that double stranded RNA; or it can comprise additional base pairs at either, or both, ends of the double stranded RNA, provided that the total of length of the siRNA is between about 19 and about 29 bp, inclusive. One embodiment of the invention is an siRNA, one of whose strands consists essentially of a sequence represented by SEQ ID NO:1, SEQ ID NO:2, SEQ ID NO:3, SEQ ID NO:4, SEQ ID NO:5 or SEQ ID NO:6.

The term "consists essentially of," when used in the context of biopolymers, refers to a sequence which is intermediate between the specific number of residues (amino acids or nucleotides) encompassed by the term "consisting of" and the longer unspecified length encompassed by the term "comprising." Residues in addition to the residues encompassed by "consisting of" language do not affect the basic and novel characteristics (e.g., in the present case, the ability to inhibit VEGF-A or VEGF-A receptor expression and/or activity) of the molecule encompassed by the "consisting of" language.

As for sequence variants, in general it is preferable that an inhibitory nucleic acid, such as an antisense molecule, a ribozyme (the recognition sequences), or an siRNA, comprises a strand that is complementary (100% identical in sequence) to a sequence of a gene that it is designed to inhibit. However, 100% sequence identity between the nucleic acid and the target gene is not required to practice the present invention. Thus, the invention has the advantage of being able to tolerate naturally occurring sequence variations that might be expected due to genetic mutation, strain polymorphism, or evolutionary divergence. Alternatively, the variants may be artificially generated. Nucleic acid sequences with, e.g., small insertions, deletions, and single point mutations relative to the target sequence can be effective for inhibition.

The degree of sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than about 90% sequence identity (e.g., about 95%, 98% or 99%), or even 100% sequence identity, between the inhibitory nucleic acid and the portion of the target gene is preferred.

Alternatively, an active variant of an inhibitory nucleic acid of the invention is one that hybridizes to the sequence it is intended to inhibit under conditions of high stringency. For example, the duplex region of an siRNA may be defined functionally as a nucleotide sequence that is capable of hybridizing with a portion of the target gene transcript under high stringency conditions (e.g., 400 mM NaCl, 40 mM PIPES pH 6.4, 1 mM EDTA, 70° C. hybridization for 12-16 hours, or equivalent conditions), followed generally by washing.

A skilled worker can readily test a candidate siRNA or antisense variant molecule to determine if it is inhibitory.

As used herein, an "isolated" RNA or DNA is one that is in a form not found in its original environment or in nature, e.g., more concentrated, more purified, separated from at least one other component with which it is naturally associated, in a buffer, etc.

In another embodiment, the inhibitory agent inhibits an activity of the VEGF-A or a VEGF-A receptor. Examples of such inhibitors of activity (antagonists) include, e.g., an antibody specific for VEGF-A or VEGF-A receptor, a peptide or oligonucleotide which binds to the polypeptide of interest and effectively eliminates its function, or a small molecule pharmaceutical agent. Another potential antagonist is a closely related protein which binds to a VEGF receptor but inhibits its function rather than activating it. For example, an antagonist of VEGFR2 receptor could be a protein that is closely related to VEGFR2, but is an inactive form of the polypeptide and thereby prevents the action of VEGFR2. Examples of these antagonists include a negative dominant mutant of the VEGFR2 polypeptide, wherein one chain of the heterodimeric form of VEGFR2 is dominant and is mutated such that biological activity is not retained. An example of a negative dominant mutant includes a truncated version of a dimeric VEGFR2 which is capable of interacting with another dimer to form wild type VEGFR2, but the resulting homo-dimer is inactive and fails to exhibit characteristic VEGFR2 activity.

One aspect of the invention is an antibody which is generated against a protein molecule or a peptide fragment of VEGF-A or a VEGF-A receptor. As used herein, the term "antibody" is used in the broadest sense and encompasses single monoclonal antibodies, polyclonal antibodies, chimeric antibodies, humanized antibodies, single-chain antibodies and antibody fragments (e.g., Fab, F(ab'), Fv). Antibodies are designed to block the activity of VEGF-A or a VEGF-A receptor, e.g. as it relates to the stimulation of hyperplastic epithelium in sinonasal polyp tissue. The terms a "blocking" antibody or a "neutralizing" antibody, as used herein, means an antibody that can inhibit the function of a defined target of interest. The antibodies can be produced by standard antibody technologies (e.g., monoclonal antibody technologies) and can be humanized if successful in blocking the VEGF-A or VEGF-A receptor activity. If desired, candidate antibodies first can be shown in vitro to suppress VEGF-A or VEGF-A receptor activity, and then tested in vivo using a conventional animal model. Those antibodies that successfully inhibit VEGF-A or VEGF-A receptor activity can be further processed to be humanized and ready for use in humans. A preferred antibody of the invention is highly specific (immunospecific) for VEGF-A or a VEGF-A receptor.

Guidance for producing antibodies (or other agents) specific for VEGF, NP-1 and VEGF receptors is provided, e.g., in the following US patents and patent publications. These and other references cited herein which provide guidance for performing methods related to the present invention are incorporated by reference herein in their entirety.

U.S. Pat. No. 5,730,977 Anti-VEGF human monoclonal antibody

U.S. Pat. No. 5,840,301 Methods of use of chimerized, humanized, and single chain antibodies specific to VEGF receptors U.S. Pat. No. 5,874,542 Single chain antibodies specific to VEGF receptors U.S. Pat. No. 6,342,219 Antibody compositions for selectively inhibiting VEGF U.S. Pat. No. 6,884,879 Anti-VEGF antibodies U.S. Pat. No. 7,335,357 Antagonists of neuropilin receptor function and use thereof U.S. Pat. No. 7,375,193 Anti-VEGF antibodies U.S. Pat. No. 7,531,172 Methods of treating diseases with a VEGF antagonist U.S. Pat. No. 7,534,878 Composition and method of RNAi therapeutics for treatment of cancer and other neovascularization diseases U.S. Pat. No. 7,576,189 Antibodies to human vascular endothelial growth factor 2 and methods of using the same 20060115477 Neuropilin-1 inhibitors 20080213268 Neuropilin Antagonists Another class of agents that inhibit the function of VEGF-A or a VEGF-A receptor are small molecules which bind to and occupy the active site of the polypeptide, thereby making the catalytic suite inaccessible to substrate which the normal biological activity is prevented. Examples of small molecules include, e.g., small peptides or peptide-like molecules, and small organic compounds, which can include both synthetic compounds and naturally occurring compounds.

A number of inhibitors of the expression or the activity of VEGF-A or a VEGF-A receptor have been proposed and/or developed for the treatment of conditions which are mediated by VEGF other than chronic inflammatory respiratory disorders. Such conditions include, e.g., anti-tumor therapies, treatment of macular degeneration, and of other conditions mediated by angiogenesis. It is expected that such agents would also be effective against chronic inflammatory respiratory disorders such as CRSwNP. It might be necessary to modify the formulations, dosages and routes of administration of these agents in order to optimize the treatment of chronic inflammatory respiratory disorders. Suitable modifications would be evident to a skilled worker, using routine, conventional procedures. For example, suitable formulations are described in Remington's Pharmaceutical Sciences, 18th ed., Mack Publishing Company, 1990.

Among the agents that have been developed for treating other indications are the following: an RNA aptamer, such as pegaptanib; a partial or full-length antibody, such as ranibizumab or bevacizumab; a VEGF receptor decoy, such as VEGF Trap (see, e.g., U.S. Pat. No. 7,541,172); small interfering RNA-based therapies, such as a microRNA or an siRNA, including the siRNAs described herein, microRNAs, bevasiranib, or AGN211745; a tyrosine kinase inhibitor, such as vatalanib, pazopanib, TG100801, TG101095, AG013958 or AL39324; or a blocking peptide. For example, one can use a blocking peptide against the VEGF receptors NP1 and/or VEGFR2, such as described in Barr et al. (2005) *Br J Cancer* 92, 328-333.

A number of considerations are generally taken into account in designing delivery systems, routes of administration, and formulations for inhibitory agents of the invention. The appropriate delivery system for an inhibitory agent of the invention will depend upon its particular nature, the particular clinical application, and the site of drug action.

Among the methods which have been used successfully to deliver siRNAs are, e.g., plasmid vectors; retrovirus vectors, including oncoretrovirus vectors and lentivirus vectors; and hydrodynamic "high pressure" delivery.

In one embodiment of the invention, when treating a subject, an inhibitory agent is administered by systemic intravenous (IV) or by a local intranasal route, such as an intranasal spray, a metered-dose inhaler, a nebulizer, or a dry powder inhaler. Formulations for delivery by a particular method (e.g., solutions, buffers, and preservatives, as well as droplet or particle size for intranasal administration) can be optimized by routine, conventional methods that are well-known in the art. For inhibitory agents that are in the form of aerosol formulations to be administered via inhalation, the aerosol formulations can be placed into pressurized acceptable propellants, such as dichlorodifluoromethane, propane, nitrogen or the like.

The dose of an agent of the invention, or composition thereof, administered to an animal, particularly a human, in the context of the present invention should be sufficient to effect at least a detectable amount of a therapeutic response in the individual over a reasonable time frame (e.g., an anti-inflammatory- or antiproliferative-effective amount). The exact amount of the dose will vary from subject to subject, depending on the species, age, weight and general condition of the subject, the severity or mechanism of any disorder being treated, the particular agent or vehicle used, its mode of administration and the like. The dose used to achieve a desired effect in vivo will be determined by the potency of the particular agent employed, the pharmacodynamics associated with the agent in the host, the severity of the disease state of infected individuals, as well as, in the case of systemic administration, the body weight and age of the individual. The size of the dose also will be determined by the existence of any adverse side effects that may accompany the particular inhibitory agent, or composition thereof, employed. It is generally desirable, whenever possible, to keep adverse side effects to a minimum.

Dosages for administration of an inhibitory agent of the invention can be in unit dosage form, such as a tablet or capsule. The term "unit dosage form" as used herein refers to physically discrete units suitable as unitary dosages for human and animal subjects, each unit containing a predetermined quantity of an inhibitor of the invention, alone or in combination with other therapeutic (e.g., anti-inflammatory) agents, calculated in an amount sufficient to produce the desired effect in association with a pharmaceutically acceptable diluent, carrier, or vehicle.

The specifications for the unit dosage forms of the present invention depend on the particular agent of the invention, or composition thereof, employed and the effect to be achieved, as well as the pharmacodynamics associated with each polypeptide, or composition thereof, in the host. In some embodiments, the dose administered is an "anti-inflammatory effective amount or an "anti-proliferative effective amount."

One skilled in the art can easily determine the appropriate dose, schedule, and method of administration for the exact formulation of the composition being used, in order to achieve the desired response in the individual patient.

One embodiment of the invention is a kit useful for any of the methods disclosed herein. Such a kit can comprise one or more isolated inhibitors of the invention. A device, composition, or other means for administering the inhibitor to the nasal tract can also be included. A kit suitable for a therapeutic treatment in a subject may further comprise a pharmaceutically acceptable carrier and, optionally, a container or packaging material. Among other uses, kits of the invention can be used in experiments, e.g. to study mechanisms by which VEGF acts as an epithelial cell mitogen, etc. A skilled worker will recognize components of kits suitable for carrying out any of the methods of the invention.

Optionally, the kits comprise instructions for performing the method, and/or a notice in the form prescribed by a governmental agency regulating the manufacture, use or sale of pharmaceuticals or biological products (such as the FDA), which notice reflects approval by the agency of manufacture, use or sale for human administration. In addition, agents in a kit of the invention may comprise other therapeutic compounds, for combination therapy. Other optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form for use as therapeutics, or in single reaction form for diagnostic use.

In the foregoing and in the following examples, all temperatures are set forth in uncorrected degrees Celsius; and, unless otherwise indicated, all parts and percentages are by weight.

EXAMPLES

I. Methods

Human Subjects

All subjects studied were enrolled after obtaining informed consent under a Johns Hopkins Medicine Institutional Review Board-approved human subjects research protocol. The CRSwNP patients were defined by historical, endoscopic, and radiographic criteria, and by meeting the definition of the American Academy of Otolaryngology-Head and Neck Surgery (AAO-HNS) Chronic Rhinosinusitis Task Force. Specifically, CRS alone patients had continuous symptoms of rhinosinusitis as defined by the Task Force report for greater than 12 consecutive weeks, associated with computed tomography of the sinuses revealing isolated or diffuse sinus mucosal thickening and or air fluid level. CRSwNP subject was defined by endoscopic exam findings of polyps and post-treatment CT scan confirmation of persistent bilateral and diffuse paranasal sinus mucosal thickening. Surgery for CRSwNP patients was only performed if a patient's symptoms and radiographic findings failed to resolve despite at least 6 weeks of treatment with oral antibiotics, topical corticosteroids, decongestants, and/or mucolytic agents in accordance with the accepted standards of medical care. However, CRSwNP subjects, CRS alone, and normal control subjects who were chosen for these studies had no immediate preoperative steroids within 14 days prior to obtaining any specimen. In addition, CRSwNP subjects had no intranasal glucocorticoid exposure during the immediate one-month post-operative period. Normal control subjects were defined as those individuals failing to meet criteria for CRS as defined above and having no evidence of sinus disease. These subjects were normal healthy volunteers. Normal control sinus tissue was obtained as discarded sinus tissue from non-CRS patients who were undergoing endoscopic surgery for transphenoidal hypophysectomy or cerebrospinal fluid leak repair. As a secondary characteristics, atopic status was defined by puncture skin test positivity using 22 allergens as previously described (PS Creticos, In vivo provative testing for IgE-mediated disease. New York: Marcel Dekker; 1999). These include cat, dog, mouse and rat danders, short ragweed, mugwort, rye grass, Bermuda grass, oak, birch, dust mites (*Dermatophagoides pteronyssinus* and *Dermatophagoides farinae*), cockroach (*Blatella germanica, Periplaneta americana*, and *Blata orientalis*), and mold (*Alternaria alternata, Aspergillus fumigatus, Cladosporium herbarum, Curvularia, Dreschella, Fusarium*, and *Rhizopus* (ALK Laboratories). Phosphate buffered saline and histamine was used as negative and positive controls, respectively. The skin test response is measured 15 min after application on the forearm by puncture with a bifurcated needle. An imprint of the perimeter of the wheal and erythema will be made using 3M Transpore tape transferred onto a sheet of paper for permanent documentation. The two cross diameters were measured to quantitate the size of the wheal and the erythema. A positive test is defined as an average wheal diameter greater than or equal to 3 mm above the saline control. Subjects with asthma were defined as those who: 1) have a physician diagnosis of asthma as described by NHLBI expert panel 3 report (Expert panel report 3 (epr-3): Guidelines for the diagnosis and management of asthma-summary report 2007. *J Allergy Clin Immunol* 2007; 120: 594-138) where subjects who display FEV1/FVC ratio less than 0.7 measured prior to optimization of asthma control and either one of the following conditions following administration of a bronchodilator: (a)>12% improvement in FEV1 (or FVC) or (b) an absolute improvement of >0.2 L; and 2) have been placed on prescription medication for asthma (such as bronchodilators, inhaled steroids, or oral steroids). In addition, CRSwNP subjects with asthma were further classified with respect to level of asthma control by (1) FEV1 values measured within one month of enrollment and (2) number of exacerbations requiring oral systemic corticosteroid treatment to control asthma symptoms as defined by the NHLBI expert panel 3 report, referred to above.

Collection of nasal scrapings: Nasal epithelial cells were collected from the inferior nasal turbinate by curettage with a sterile nasal cytology brush (Wampole, Harrisburg, Pa.) and were rinsed twice in a sterile Eppendorf tube containing 5 ml of lactated Ringers solution as previously described (Kim et al. (2005) *Am J Respir Cell Mol Biol* 33, 280-289). The cells are centrifuged at 300×g for 5 min at room temperature. Each nasal scraping specimen yields 1-2×10$^6$ cells, of which >95% are epithelial cells by Wright stain cell count.

Collection of nasal lavage samples. Nasal lavage was collected according to previously described methods (Naclerio et al. (1983) *Am Rev Respir Dis* 128, 597-602). Lavages were performed with sterile saline solution prewarmed to 37° C. Briefly, 5 ml of saline was instilled into each nasal cavity a pipette with the head extended, while the patient holds his/her breath for 10 seconds. Then, the patient is asked to tilt his/her head forward to allow the saline to drip into a collection basin. The lavage fluid was processed by spinning at 3600 rpm for 15 minutes, aliquoted and frozen in –80° C. for detection of VEGF, other growth factors, and total protein.

Culture of PNEC: Epithelial cells cultured from nasal scrapings were cultured in bronchial epithelial basal medium (Biosource, Camarillo, Tex.) on collagen-coated plates as previously described (Kim et al. (2005, supra); Heinecke et al. (2008) *J Allergy Clin Immunol* 121, 1155-1160; Kim et al. (2000) *J Immunol* 165, 3384-3392). Cultures of PNEC routinely were 99-100% cytokeratin positive staining at the time of harvest. PNEC were routinely used for all in vitro studies at first or second passage only. For functional studies measuring cell growth and apoptosis, the cells were incubated for varying lengths of time with recombinant VEGF (R&D, Minneapolis, Minn., 100 ng/ml, (Conn et al. (1990) *Proc Natl Acad Sci USA* 87, 2628-2632), or antibody that has been previously shown to functionally block its target: anti-VEGF blocking antibody (R&D, 1 ug/ml), anti-NP-1 blocking antibody (Miltenyi, Biotech, Auburn, Calif., 1 ug/ml, (Wilgus et al. (2005) *Am J Pathol* 167, 1257-1266), anti-VEGFR1 blocking antibody (R&D 10 ug/ml (Ferrara et al. (1997) *Endocr Rev* 18, 4-25), anti-VEGFR2 blocking antibody (R&D, 1 ug/ml, (Giuliani et al. (2003) *Blood* 102, 638-645), recombinant EGF (R&D, 50 ng/ml, (Beck et al. (2006) *J Immunol* 177, 3344-3354), or irrelevant isotype control antibody (eBioscience, San Diego, Calif.).

Flow cytometry: The monoclonal antibodies against VEGF (R&D, Minneapolis, Minn.) and NP1 (Miltenyi Biotech, Auburn, Calif.) used for flow cytometry were analyzed as previously described with a FACS Calibur flow cytometer (Becton Dickinson, Mountain View, Calif.) using CellQuest software (Kim et al. (2005), Heinecke et al. (2008), and Kim et al. (2000), all supra.) The viability of PNEC at the time of cell harvest was assessed by propidium iodide exclusion. Fluorescence was determined on all cells for each sample after debris, dead cells and aggregates were excluded by forward angle and side scatter gating. Mean fluorescence intensity (MFI) was compared with control staining using an irrelevant isotype-matched mouse monoclonal antibody. For each sample, at least 10,000 events were collected, and histograms were generated. Data are usually expressed as means±SEM.

Immunohistochemistry: Surgical sinonasal tissue was immediately fixed in 4% formaldehyde in phosphate buffered saline (PBS, 4° C., 4 hr) and then rinsed with PBS. Antibody to VEGF (R&D), NP-1 (Miltenyi), VEGFR1 (R&D), VEGFR2 (R&D), phospho-VEGFR2 (Santa Cruz Biotechnology, Santa Cruz, Calif.), or irrelevant IgG isotype (eBioscience) control was performed as previously described (Kim et al. (2005), Heinecke et al. (2008), and Kim et al. (2000), all supra.). To assure that detection of positive staining was performed in a standardized and uniform manner between tissue samples, staining was routinely performed in sets of tissues using a specimen from each of the two patient groups. Each round of staining was exposed to diaminobenzidine for a fixed duration to the standardize time for color development. The slides were evaluated with a brightfield microscope (Olympus BX-50) equipped with a camera (Q-Imaging Retiga Exi or Spot ET-3 CCD camera) and a micrograph field of view of the entire stained section. Image Pro Lab imaging software (Microsoft) was used to analyze areas of positive staining in each digitized micrograph. All epithelial cells were selected (from the basement membrane to the luminal surface) as the region of interest (ROI) in each image of the immunohistochemically stained (e.g. VEGF) section. A standard size of ROI surface area was used and applied to all images. Simple bi-level thresholding, based on criteria for positive staining was set by a trained personnel who is blinded to the specimen phenotype. This threshold window was set and applied to all analyzed images; the number of nuclei was also counted in the ROI. The software measurement of the area of positive immunostaining and number of nuclei in the ROI are transferred to an Excel spreadsheet for statistical analysis and determination of the average intensity area per cell (total area of positive immunostaining divided by number of nuclei). The data are expressed as intensity of staining per cell.

ELISA assay for growth factors: VEGF, EGF, and TGFβ1 from nasal lavages and cell supernatants were measured using ELISA kits from R&D according to manufacturers instructions. The minimum detectable concentration of was typically 5.0 pg/ml. Assay of each sample was performed in triplicate. Data are expressed per ug of total protein that was measured by Bradford assay (Bio-Rad, Hercules, Calif.).

Determination of PNEC growth to culture confluence: Two hundred thousand cells/well were plated onto collagen coated 6 well plates. Attainment of culture confluency was assessed under 40× power phase contrast light microscopy. An estimate of confluency was determined by averaging inspection of 5 separate fields: 0, 90, 180, 270 degree and center of each well. Confluency was defined when a minimum average of 90% has been reached. Each sample assay was performed in triplicate and the analysis blinded to the subject group.

Cyquant cell proliferation assay: Cell proliferation was assayed using the Cyquant cell proliferation assay (Molecular Probes). Cells were seeded at 5×10$^3$ cells/well and grown to 50% confluence in 96-well plates in serum-free bronchial EC growth medium (Cambrex), deprived of EGF for 24 hrs before challenge to synchronize cell growth, and subsequently stimulated according to the experimental protocols. As per the manufacturer's instructions, at the end of the experiment, the cell supernatants were aspirated and the cells were lifted by trypsinization. Cell lysis was performed by two sequential freeze-thaw cycles. Standard curves were executed with each run of the assay according to manufacturers instruction. Cells were then incubated for 5 min at room temperature with Cyquant lysis buffer containing the Cyquant-GR fluorescent dye. Fluorescence was measured using a Cytofluor 4000 fluorescence reader (Applied Biosystems (Life Technologies). Each experimental condition was assessed in quadruplicates.

siRNA transfection: PNEC was grown to 75% confluence and transfected with indicated concentration of target gene NP1 (100 nM), negative control, or rhodamine-tagged control siRNA (Qiagen, Valencia, Calif.) using RNAimax transfection reagent made up in OptiMem buffer (1:1 volume) as directed by vendor (all reagents from Invitrogen). PNEC were then exposed to siRNA/RNAimax in cell culture media without antibiotics (1:3) for 24 hours at 37° C. Viability is monitored by light microscopy. Transfection efficiency was assessed by measuring average % of rhodamine positive cells per field×4 sampled fields at 10× and 40× magnification using fluorescent microscopy.

Statistical Analysis. All data are expressed as mean±SEM. Comparison between the phenotypic classes and control groups was analyzed using Kruskal Wallis Test. Comparison of in vitro quantitative data between multiple treatment conditions was determined using ANOVA and post hoc Bonferroni Test.

asthma) and leukotriene antagonists (indicated for asthma or rhinitis), were continued through the study. The specific monoclonal antibodies used in this assay (R&D Systems) have been shown to detect all soluble human VEGF (including VEGF165 and VEGF121), EGF, and TGFβ1, respectively. Results in FIG. 1 Panel A demonstrate that subjects with CRSwNP display significantly greater than 7 fold higher levels of VEGF protein in nasal lavages (177±35 pg/ug protein) compared to normal control subjects (24±3 pg/ug) or CRS subjects without sinonasal polyposis (25±2 pg/ug). In addition, removal of polyps and achievement of quiescent disease in CRSwNP subjects resulted in a dramatic reduction of VEGF levels comparable to that of normal control values (see FIG. 1 Panel B). Total protein levels in nasal lavages did

TABLE 1

Characteristics of Human Subjects

| Subject | Phenotype | Gender | Age | Skin Test | Medications at time of enrollment | Asthma | FEV1/FVC | pre FEV1 (liters) | post FEV1 (liters, % improvement) | oral corticosteroid dose per year |
|---|---|---|---|---|---|---|---|---|---|---|
| 1 | CRSwNP | M | 55 | − | | − | 0.85 | 3.79 | 3.83 (1%) | 0 |
| 2 | CRSwNP | M | 43 | + | ICS/LABA, antihistamines | + | 0.64 | 4.37 | 5.02 (16%) | 2 |
| 3 | CRSwNP | F | 20 | + | ICS/LABA, antihistamines, montelukast, albuterol | + | 0.7 | 3.2 | 3.78 (18%) | 6 |
| 4 | CRSwNP | M | 46 | + | ICS/LABA, antihistamines, montelukast, albuterol | + | 0.65 | 2.83 | 3.20 (13%) | 4 |
| 5 | CRSwNP | M | 80 | − | ICS/LABA, montelukast | + | 0.55 | 2.65 | 3.00 (13%) | 5 |
| 6 | CRSwNP | F | 32 | − | | − | 0.87 | 2.2 | 2.1 (0%) | 0 |
| 7 | CRSwNP | M | 40 | − | ICS/LABA | + | 0.57 | 3.85 | 4.08 (6%) | 1 |
| 8 | CRSwNP | F | 50 | − | ICS/LABA | + | 0.68 | 1.83 | 2.1 (15%) | 8 |
| 9 | CRS | F | 68 | − | antihistamines | | | | | |
| 10 | CRS | M | 46 | − | antihistamines, montelukast (for rhinitis) | | | | | |
| 11 | CRS | M | 73 | − | | | | | | |
| 12 | CRS | M | 66 | − | | | | | | |
| 13 | CRS | M | 43 | − | | | | | | |
| 14 | CRS | F | 29 | + | antihistamines, montelukast (for rhinitis) | | | | | |
| 15 | Control | M | 35 | − | | | | | | |
| 16 | Control | F | 58 | − | | | | | | |
| 17 | Control | M | 27 | − | | | | | | |
| 18 | Control | M | 30 | − | | | | | | |
| 19 | Control | F | 24 | − | | | | | | |

ICS = inhaled corticosteroid, LABA = long-acting beta agonist

II. Results

A. VEGF is Elevated in Nasal Lavages of CRSwNP

To examine the role of growth factors in upper airway remodeling observed in sinonasal polyposis, we compared the levels of VEGF, EGF, and TGFβ1 in nasal lavage aspirates from subjects with CRSwNP, CRS alone and normal control patient groups. Patient characteristics are given in Table 1. All subjects had a negative history of glucocorticoid usage (either intranasal or oral) at least 2 weeks prior. In addition, CRSwNP subjects had no glucocorticoid exposure during the immediate one-month post-operative period. Antihistamines were withheld 48 hours prior to skin testing and then resumed as medically indicated. All other medications, as listed in Table 1, including inhaled corticosteroids (indicated for not differ significantly between the 3 patient groups. In contrast to VEGF, there was no significant difference in the level of EGF measured in nasal these lavages between the 3 patient groups. Additionally, we failed to detect any measurable soluble TGFβ1 in nasal lavage aspirates.

Examination of secondary characteristics of CRSwNP subjects revealed that only 3/8 CRSwNP subjects were skin test positive. However, the majority of the CRSwNP subjects (6/8) examined had asthma. Furthermore, 5/8 CRSwNP subjects had poorly controlled asthma as defined by (1) FEV1<60% predicted or (2) at least 2 doses per year of oral corticosteroid treatment for asthma exacerbations.

B. VEGF is Overexpressed In Vivo and In Vitro in CRSwNP

Figure 2:
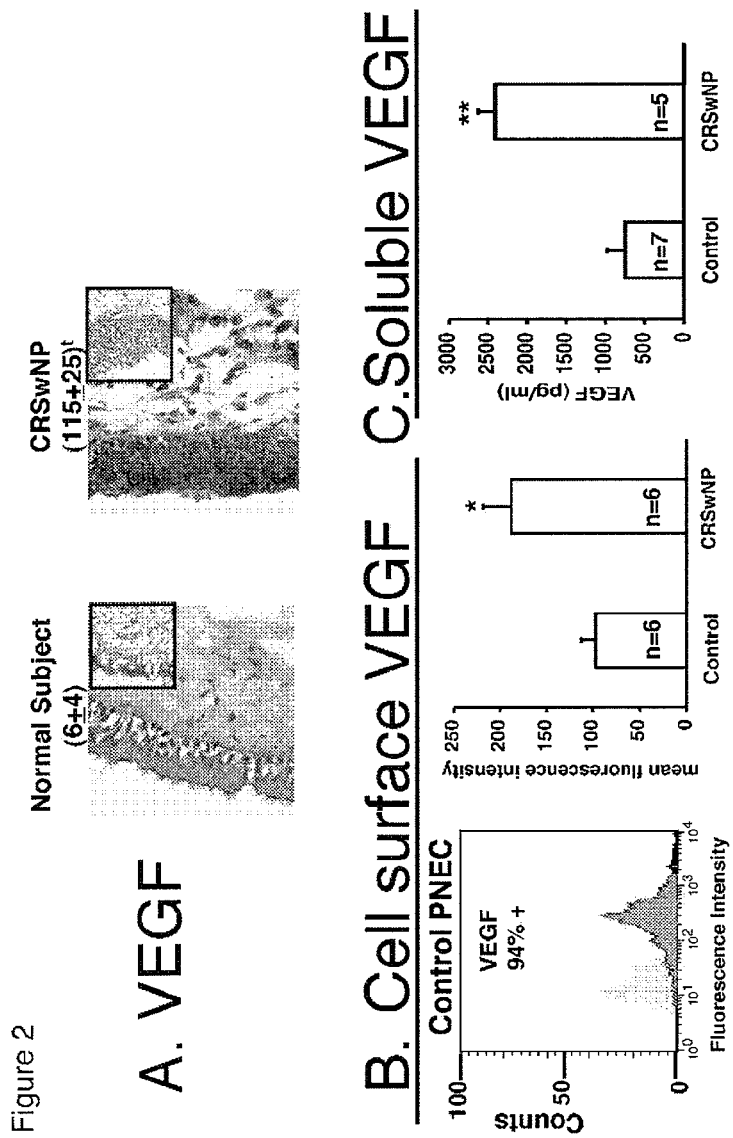
FIG. 2 shows that VEGF is over expressed by epithelial cells in sinonasal tissue.
Figure 3:
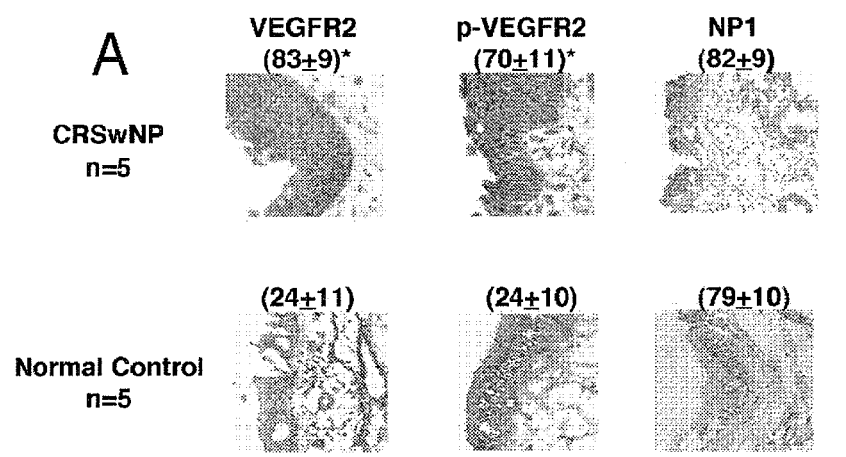
FIG. 3 shows that receptors for VEGF are abundantly expressed by epithelial cells in sinonasal tissue.
Figure 3:
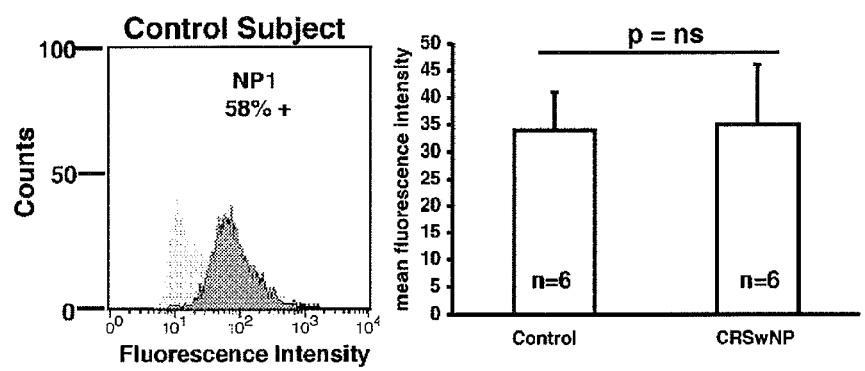

To confirm the presence of VEGF on epithelium in sinonasal polyps, immunohistochemical staining was performed on sinus tissue surgical samples using monoclonal antibodies against VEGF, and isotype control IgG. Sinonasal tissue from CRSwNP (maxillary sinus polyp) and normal control subjects (maxillary or sphenoid sinus) were tested. The staining intensity of digitized images of epithelial cells was objectively assessed by Image Pro software (Microsoft) and expressed as intensity units per epithelial cell using similar sized sampling areas. Firstly, FIG. 2A (and in FIG. 3) shows that epithelial cell hyperplasia, which is characteristic of CRSwNP, is uniquely present in CRSwNP, and absent from normal control subjects. Data show that VEGF was detected in representative human sinonasal tissue. The irrelevant IgG isotype negative control with secondary antibody shown in the inset demonstrates no nonspecific brown staining in the epithelial layer in both subject groups. As additional controls, staining performed in the absence of primary or secondary antibody yielded no significant signal. The intensity of staining within the epithelium varied between subject groups and the sinonasal polyp from CRSwNP subject demonstrated significantly increased staining intensity for VEGF especially within the epithelial cell layer as compared to sinonasal tissue from maxillary sinuses of control subjects ($p<0.012$). VEGF staining was observed in the epithelial cell layer, but not exclusively.

Since we found VEGF to be highly expressed on epithelial cells in vivo, we wanted to know if VEGF was detectable on the surface of nasal epithelial cells in vitro. VEGF is known to exist on the cell surface residing within an extracellular pool. In addition, VEGF is known to exist in a membrane bound form. The results shown in FIG. 2B (left) display flow cytometric findings using specific monoclonal antibodies to VEGF on nasal epithelial cells taken from inferior turbinates which were expanded in cell culture from a normal control subject. The anti-VEGF antibody used detects all isoforms of VEGF, including membrane bound VEGF189. The results demonstrate fairly unimodal detection of robust levels of cell surface expression of VEGF (94% positive) on PNEC from a normal control subject. FIG. 2B (middle) compares VEGF cell surface expression on PNEC taken from inferior turbinates from control and CRSwNP subjects. The data demonstrate that cell surface expression of VEGF from CRSwNP is increased by ~2 fold ($p<0.05$). VEGF is also known to be secreted by cells in the form of two soluble isoforms: VEGF165 and VEGF121. To examine whether PNEC from CRSwNP subjects produce elevated levels of soluble VEGF, we compared soluble VEGF (both VEGF165 and VEGF121) released into cell supernatants of PNEC from CRSwNP and control subjects. Wells from a 6-well plate were seeded with identical cell numbers of PNEC from individual subject donors and grown to 90% confluence. Cell supernatants were assayed for VEGF using ELISA. The results in FIG. 2C demonstrate that PNEC from CRSwNP subjects expressed, produced and released greater than 3 fold higher levels of soluble VEGF into the cell supernatant as compared to PNEC from normal control subjects ($p<0.02$). These data demonstrate that both soluble and cell surface VEGF is over expressed by PNEC from CRSwNP subjects.

C. VEGFR2, Phospho-VEGFR2, and NP1 are Abundantly Expressed by Epithelial Cells in Sinonasal Tissue.

Because VEGF was found to be so abundantly present in epithelium of sinonasal polyp tissue, we hypothesized that VEGF has a biological function on these cells. We hypothesized that the receptors for VEGF are also present on nasal epithelium. VEGFR2 is known to exhibit robust tyrosine kinase activity and auto- and transphosphorylation when activated by VEGF ligand binding. To examine whether activation of the VEGF signaling pathway occurs in sinonasal epithelium in vivo, we looked for the presence of phosphorylation of VEGFR2 by performing immunostaining for VEGFR2 and phospho-VEGFR2. FIG. 3A demonstrates that VEGFR2 was detected in human sinonasal tissue from CRSwNP subjects, but barely detectable in normal control subjects ($p<0.04$). Additionally, there was markedly elevated staining of phospho-VEGFR2 in polyps of subjects with CRSwNP as compared to specimens from normal control subjects ($p<0.04$). Interestingly, we detected robust constitutive staining of neuropilin-1 (NP1), the co-receptor for VEGF, in sinonasal epithelium from both patient groups. These studies are the first to report expression of NP1 on human airway epithelial cells. In vitro studies, shown in FIG. 3B, demonstrated that cell surface NP1 is expressed at high constitutive levels by PNEC (58% positive) derived from control subjects. Furthermore, both in vivo and in vitro expression of NP1 appears to be unaffected by disease phenotype. These data show that, not only is the ligand VEGF abundantly present in diseased sinonasal epithelium, but that at least one of the receptors which is necessary for signaling is also present in active form. In addition, NP1 has been newly identified to be abundantly expressed on airway epithelial cells of sinonasal tissue in both patient groups.

D. PNEC from CRSwNP Subjects Display Elevated Growth Rates In Vitro

Figure 4:
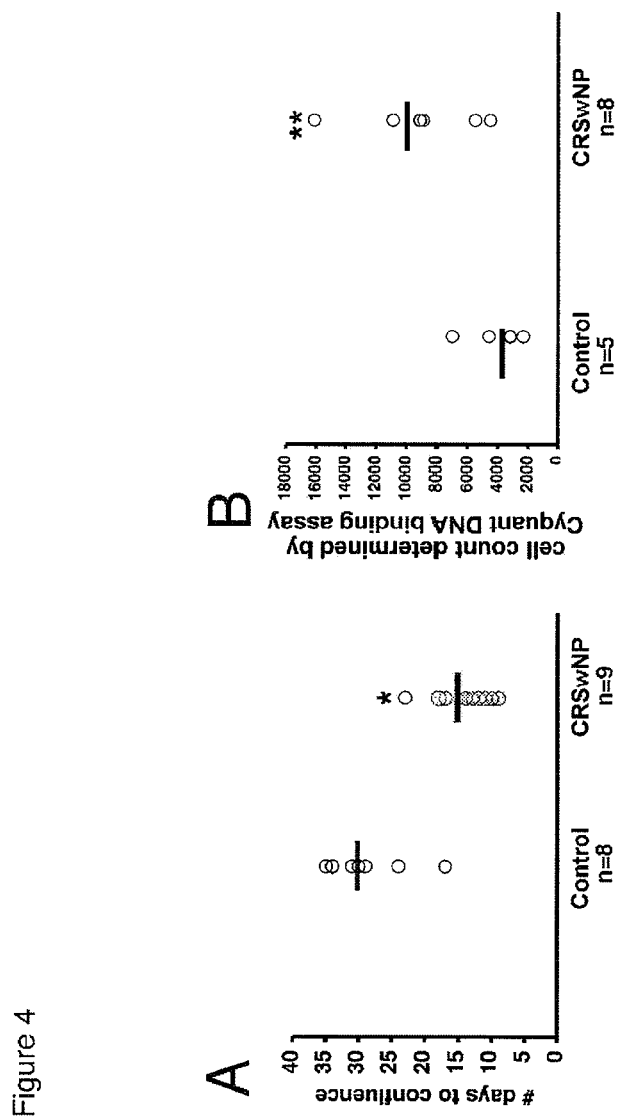
FIG. 4 shows that primary nasal epithelial cells (PNEC) from CRSwNP subjects display faster growth rates in vitro.

During the course of expanding PNEC in culture from nasal scrapings, we observed that epithelial cells harvested from CRSwNP subject displayed a faster rate of growth as compared to normal control cells, consistent with their hyperplastic histologic appearance. Therefore we undertook efforts to systematically examine the growth and survival of nasal cells derived from CRSwNP subjects and compare them to nasal epithelial cells derived from controls. We standardized culture conditions to optimize recovery of cells by minimizing time from harvest to seeding as well as the initial cell seeding concentration and assessed the number of days to culture confluency. The results FIG. 4A demonstrate that sinonasal epithelial cells derived from CRSwNP have a 2.3 fold increase in rate of cell growth to confluency as compared to normal control PNEC, when grown under identical seeding concentrations and conditions ($p<0.008$). To examine this further, we directly quantitated net cell growth using Cyquant dye fluorometric quantification of DNA (FIG. 4B). After 96 hours in culture, PNEC from inferior turbinates of CRSwNP subjects displayed a greater than 2 fold faster growth rate as compared to PNEC from control subjects ($p<0.005$). In CRSwNP subjects, PNEC obtained directly from the polyps by nasal brushing (cell count at 96 hours $10584\pm1249$, n=5) demonstrated similar growth rates to PNEC harvested from the inferior turbinate (see FIG. 4 Panel B, $9162\pm1331$, n=8) and demonstrated elevated growth rates compared to PNEC from control subjects ($p<0.006$, $4049\pm919$, n=5). Because elevated growth rate of epithelial cells from CRSwNP subjects was similarly observed in cells harvested from either polyps or inferior turbinates, comparison of in vitro PNEC behavior between CRSwNP and control subjects was performed using PNEC from inferior turbinates so that matched comparison of cell types could be made.

E. VEGF Drives Human Nasal Epithelial Cell Growth

Figure 5:
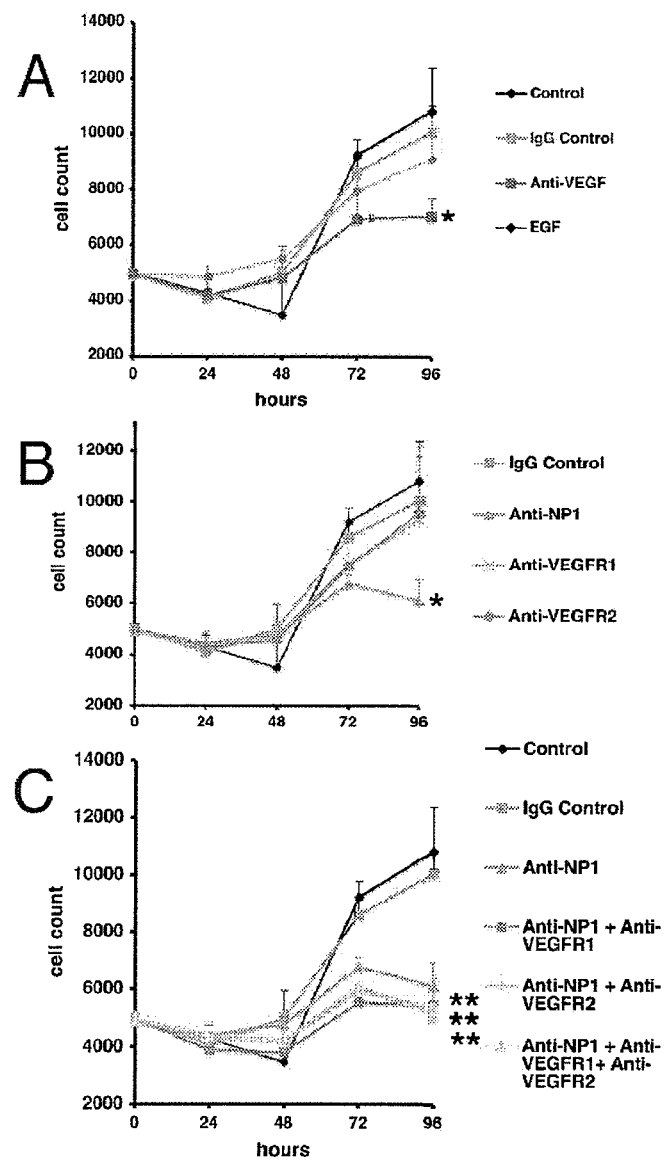
FIG. 5 shows that sinonasal epithelial cell growth is VEGF dependent.

Given the excessive levels of VEGF from sinonasal epithelium derived from CRSwNP, we hypothesized that VEGF may be acting in an autocrine fashion to increase the growth rate of epithelium from CRSwNP. To address this notion, we examined the effect of functional blocking antibodies to VEGF and to components of VEGF signaling pathway on proliferation rates of PNEC in vitro. Synchronization of the cell cycle was first performed by withdrawal of basal EGF from the media. All conditions had no exogenous VEGF supplementation. FIG. 5A shows that exposure of blocking antibody to VEGF ligand for 96 hours resulted results in a 34% inhibition of cell growth (p<0.05). Exposure to blocking antibody against VEGFR1 or VEGFR2 alone resulted in a modest 12% inhibition in cell proliferation rates. However, exposure to functional blocking antibody against co-receptor NP1 resulted in a 43% inhibition of cell growth (FIG. 5B) (p<0.05). The combination of blocking antibody to NP1 and anti-VEGFR1 and for anti-VEGFR2 antibody resulted in a greater decline in cell proliferation to 50% (FIG. 5C, p<0.02). Exposure to IgG control antibody had no effect. Thus the effect of exposure to multiple blocking antibodies to VEGF receptors was additive. In addition, exposure to recombinant EGF had no significant effect on cell growth up to 96 hours. The results of this analysis were highly reproducible in that the standard deviation of quadruplicate measurements obtained with this assay was small (<10% of measured values). In addition, the standard deviation between the experiments (n=5 donor subjects) ranged between 12-27% of the mean growth rates. Cell proliferation at 96 hours for each condition was also assessed using BrdU incorporation (Calbiochem) and resulted in identical patterns of cell growth. These results demonstrate that VEGF functions in an autocrine manner to promote epithelial cell growth.

F. VEGF Inhibits Apoptosis Through NP1

Figure 6:
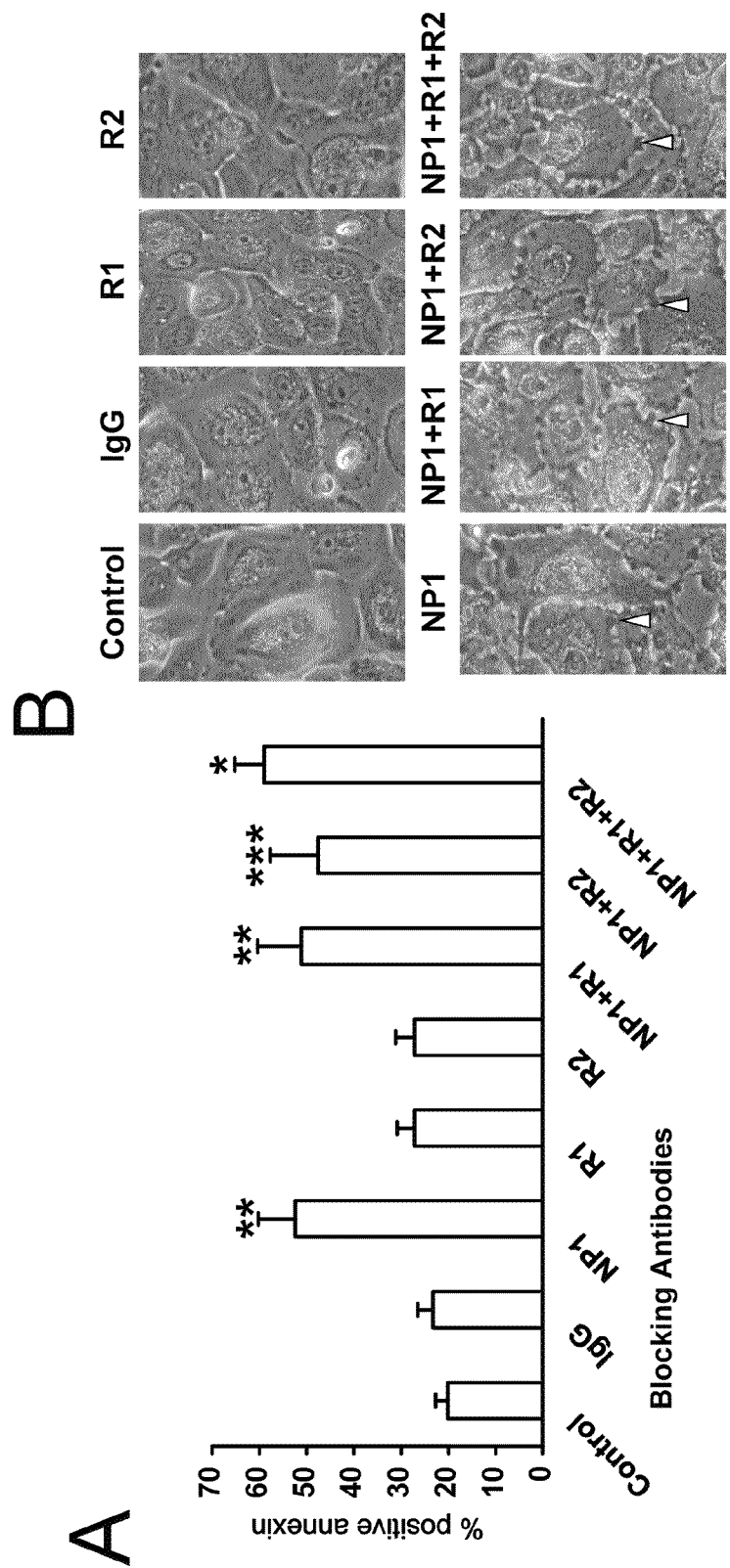
FIG. 6 shows that functional blocking of NP1 results in apoptosis. PNEC from CRSwNP subjects (n=5) were grown to 90% confluence and incubated for 48 h with blocking antibodies to NP1 (1 ug/ml), VEGFR1 (R1, 10 ug/ml), VEGFR2 (R2, 1 ug/ml), IgG control (1 ug/ml), or media control and processed for flow cytometric analysis of annexin V FITC staining (R&D). Results in the FIG. 6A are expressed as mean+/−SEM of % cells staining positive for annexin.

To examine whether VEGF may also function as a prosurvival factor, we examined the effect of functional blocking antibodies to components of VEGF pathway on induction of apoptosis of PNEC in vitro. Apoptosis was determined by flow cytometric detection of annexin V-FITC staining. FIG. 6A shows that 48 hour exposure to blocking antibody to NP1 resulted in a significant 2.5 fold increase in apoptosis of PNEC from CRSwNP subjects (p<0.02). Exposure to blocking antibody to receptor VEGFR1 or VEGFR2 resulted in no significant increase in apoptosis of PNEC. The combination of blocking antibody to NP1 with anti-VEGFR1 and/or anti-VEGFR2 antibodies resulted in the same level of apoptosis observed with anti-NP1 alone (p<0.01, p<0.02 and p<0.05, respectively). FIG. 6B shows the matching light microscopic appearance of cells under blocking antibody conditions. Cells exposed to anti-NP1 or the combination of anti-NP1 with anti-VEGFR1 and/or anti-VEGFR2 demonstrated significant cell membrane blebs indicative of morphologic evidence of increased cell death, as compared to control conditions or of cells exposed to IgG control antibody, or to blocking antibody to receptors VEGFR1 or VEGFR2 alone. These results demonstrate that VEGF functions to inhibit apoptosis in PNEC through NP1.

G. VEGF Functions to Autoregulate its Own Expression in PNEC

Figure 7:
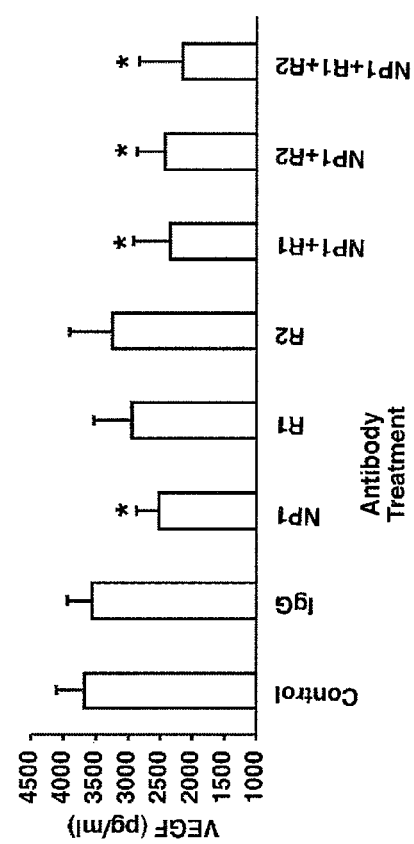
FIG. 7 shows that functional blocking of NP1 results in the inhibition of autocrine VEGF expression by PNEC. PNEC from CRSwNP subjects (n=3) were incubated for 48 h with blocking antibodies to NP1 (1 ug/ml), VEGFR1 (R1, 10 ug/ml), VEGFR2 (R2, 1 ug/ml), IgG control (1 ug/ml) or media control. Then cell supernatants were harvested and assayed for VEGF by ELISA as described in Methods. *$p<0.05$ vs Control condition by ANOVA and post hoc Bonferroni Test.

We proposed that an additional key function of VEGF from nasal epithelial cells in CRSwNP is to regulate autocrine expression of itself. To test this, we examined the effect of blocking VEGF receptor function on soluble VEGF produced and secreted by PNEC in vitro. VEGF levels in cell supernatants were measured by ELISA as described in Methods. Firstly, FIG. 7 shows that PNEC from CRSwNP produce a remarkable level of constitutive soluble VEGF in the nanomolar range. In addition, FIG. 7 shows that exposure of PNEC from CRSwNP subjects to blocking antibodies against VEGFR1 or VEGFR2 alone resulted in minimal change (20% and 12% decrease) in soluble VEGF from cell supernatents. However, exposure to anti-NP1 resulted in an enhanced 33% significant inhibition of soluble VEGF expressed by PNEC (p<0.05). Addition of anti-VEGFR1 and/or anti-VEGFR2 to anti-NP1 produced no further inhibition of soluble VEGF expression (42%, 36%, and 34% decline respectively, p<0.05 for each condition). Thus receptor blockade of VEGF function results in inhibition of autocrine VEGF production in PNEC.

To explore this further, we examined effect of silencing of NP1 by siRNA knockdown on VEGF expression. To this end, we developed optimal conditions for siRNA knockdown of NP1 in PNEC from normal control subjects. Our conditions optimized transfection efficiency to greater that 90%, as assessed by control siRNA tagged with rhodamine and fluorescence microscopy. As shown in FIG. 8B, all PNEC examined in culture were successfully transfected with siRNA tagged with rhodamine. All transfection conditions were carried out in the absence of exogenous mitogenic stimuli. Cell viability was >90% (FIG. 8B). Three independent nonoverlapping NP1 siRNA sequences were used in parallel to transfect 6 well plates of PNEC as described in Methods. The three sequences used were those represented by SEQ ID NOs 1-6.

Figure 8:
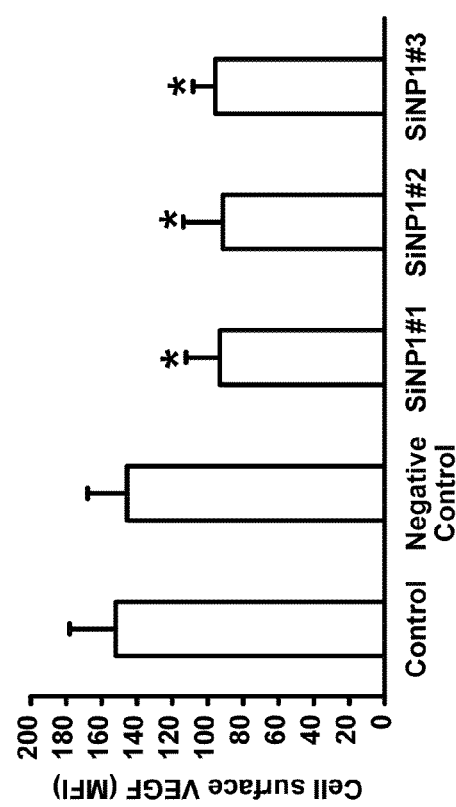
FIG. 8 shows that siRNA knockdown of NP1 results in inhibition of autocrine VEGF expression by PNEC. PNEC from CRSwNP subjects were transfected with three nonoverlapping siRNA sequences against NP1 or scrambled negative control for 24 hours as described in Methods. Untransfected media control was also used (Control).
Figure 8:
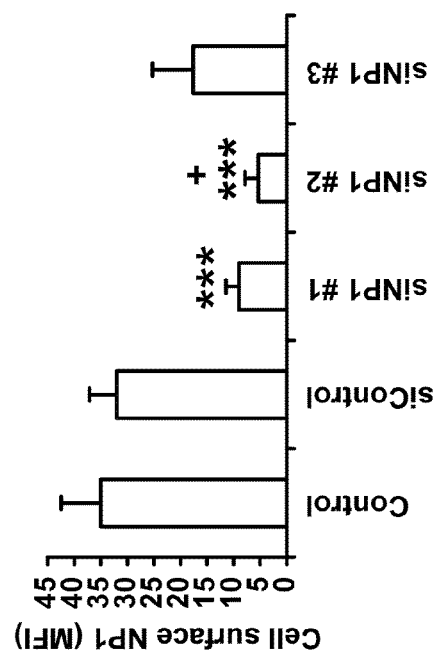
Figure 8:
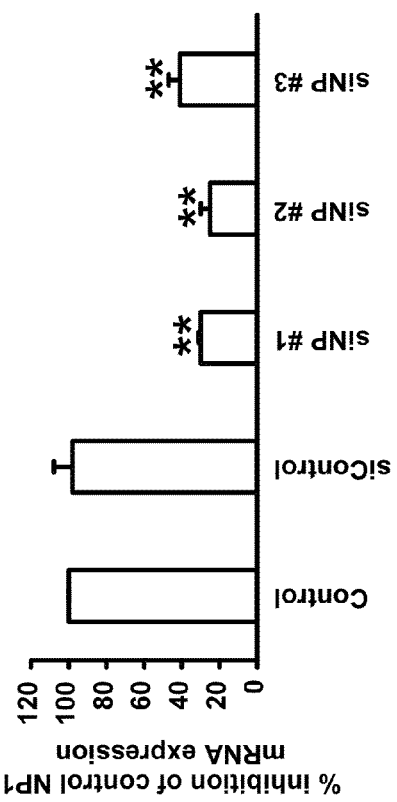

As a control, nonspecific moderate GC content scrambled siRNA was also used. Knockdown of target genes were verified by mRNA analysis using realtime PCR for NP1 and by assessing cell surface expression using flow cytometry. FIG. 8C shows that transfection of PNEC with 3 separate siRNA sequences for NP1 resulted in 70%, 75%, and 60% knockdown of mRNA for NP1 (p<0.02 vs media control for each siRNA sequence tested). This was confirmed by flow cytometric analysis of cell surface NP1 that demonstrated 75% (p<0.05 for siRNA 1) and 86% (p<0.05 for siRNA 2), and 60% (p<0.4 for siRNA 3) silencing of NP1 protein expression (FIG. 8 Panel D), showing significant knockdown by 2 of the 3 siRNA sequences tested. Scrambled negative control siRNA had no effect on mRNA levels of target genes. In addition, cell surface HLA-ABC expression was used as an irrelevant target control to monitor for nonspecific effects and was found to be unchanged (n=3). Also, absolute levels of housekeeping gene GAPDH were unchanged pre- and post-exposure to siRNA. The results in FIG. 8A shows that effective siRNA knockdown of NP1 in PNEC resulted in 37% significant inhibition of cell surface VEGF expression, similar to results obtained using antibody blockade of NP1 to inhibit autocrine VEGF expression (FIG. 7). These results further support the autoregulatory role of VEGF to upregulate its own expression through NP1.

H. Discussion

This study presents several novel observations directly relevant to the diagnosis and pathophysiology of chronic sinusitis with nasal polyps. This evidence can be summarized as follows. In addition to confirming previous observations that VEGF is over abundantly produced by the upper airways in CRSwNP subjects, we have found that: (1) VEGF levels in nasal lavage correlate with disease phenotype, being elevated in only those sinusitis patients with polyposis; (2) The co-receptor for VEGF, NP1, is highly expressed in nasal airway epithelial cells; (3) Sinonasal epithelium from CRSwNP subjects display an intrinsically increased growth rate in vitro as compared to cultured epithelial cells from normal control subjects, mimicking their in vivo behavior; (4) The increase in growth rate of the epithelial cells derived from CRSwNP subjects can be reversed by blocking antibodies targeted against either VEGF or NP1, the co-receptor for VEGF; (5) VEGF not only promotes cell growth, but also inhibits apoptosis in epithelial cells; (6) VEGF functions to autoregulate its own production in a positive feed forward manner through NP1, in non-neoplastic primary human airway epithelial cells. These results indicate that nasal epithelial VEGF can serve as a useful "biomarker" for this disease, and that its actions promote the development of epithelial cell hyperplasia, one of the key features of polyposis observed in CRSwNP. This biomarker provides a specific and sensitive test to diagnose the disease and to follow its course through time.

We found that the soluble forms of VEGF (121 and 165) measured in nasal lavage are increased specifically in subjects with CRSwNP and demonstrated that over expression of soluble VEGF in nasal lavage specifically correlates with presence of polyposis. By contrast, growth factors EGF and TGFβ1, were not elevated in CRSwNP nasal lavage aspirates. The failure to detect differences in EGF and TGFβ1 in nasal lavage may indicate that these other growth factors may not be secreted into the airway lumen or may function locally within the tissue. VEGF measured in nasal lavage aspirates are a reflection of the VEGF produced and released from the sinonasal airway tissues, the source of which could be epithelial, endothelial, or from inflammatory cell origin. Our immunohistochemical analysis of sinonasal tissue supports the conclusion that that the epithelium is a major source of VEGF production in the nasal sinus. The results represent composite staining of VEGF within the epithelial layer from all subcellular areas including cell surface VEGF bound tightly to the extracellular matrix, cell surface VEGF bound to its receptors, and VEGF within the epithelial cell. It is well known that endoscopic sinus surgery is not curative for hyperplastic polyposis, as polyp recurrence ultimately ensues. Endoscopic sinus surgery that resulted in temporary reduction of polyp load normalized VEGF production in CRSwNP subjects postoperatively, indicating that polyps are the major source of the increased VEGF in this disease. All CRSwNP subjects were controlled for absence of intranasal or oral steroids within 2 weeks of obtaining nasal lavage and throughout the one month post-operative period. Medications such as antihistamines and leukotriene antagonists taken by these subjects did not affect the level of VEGF in nasal lavage. That VEGF in nasal lavage appears to track with the presence of polyps indicates that it is a useful biomarker of hyperplastic polyposis with respect to both disease phenotype and disease activity.

These studies also emphasize that CRS is a heterogeneous disease. CRS subjects without polyposis displayed a distinctly different phenotype as compared to CRSwNP subjects in that they express lower levels of VEGF in nasal lavage, similar to normal control subjects. Phenotypic characterization of the CRSwNP subjects show that the majority, but not all, of these patients also have asthma (6/8 subjects), consistent with previously published studies (60-63). Furthermore, our data indicate that most of these patients (5/8) displayed poorly controlled asthma, requiring repeated courses of oral corticosteroids for treatment of asthma exacerbations. These data suggest that the CRSwNP phenotype correlates with presence of asthma.

A substantive finding presented here is that the nasal epithelial cells from CRSwNP subjects retained their capacity to over express VEGF and maintain their pathological phenotype in vitro when cultured at low passage number (P1 or P2). Both soluble and cell surface VEGF is over expressed by PNEC from CRSwNP subjects as compared to normal control PNEC. In addition these cells show distinctly elevated spontaneous growth rate to culture confluency and proliferation rates as compared to PNEC from normal control subjects, mimicking their in vivo hyperplastic behavior. This is analogous to recent observations that bronchial epithelial cells isolated from asthmatic airways can maintain their "abnormal" phenotype when cultured in vitro. The results from nasal lavages obtained pre- and post-surgery indicate that, on a mass basis, the bulk of soluble VEGF associated with CRSwNP is derived from the polyp tissue. The nasal epithelial cells taken from CRSwNP subjects, however, were obtained from epithelial cell brushings of the inferior turbinate within the nasal cavity (similar to PNEC from control subjects), not from the polyp tissue. Therefore, the pathological abnormality we describe here, a VEGF-over expressing hyperplastic epithelium, is related generally to the PNEC and not specifically with the polyp. Without wishing to be bound by any particular mechanism, it is suggested that this may provide a clue as to why surgical removal of polyps may provide temporary relief of polyposis and reduction of soluble VEGF in nasal lavage, but does not cure the disease. The recurrence of the polyps at some period of time post-surgically may be due to the underlying abnormality of the PNEC. These observations also do not preclude the possibility that the nasal epithelial cells present post-operatively (and pre-operatively) in CRSwNP subjects possess the capacity for over expression of non-soluble forms of VEGF, with autocrine binding and function, which may not be readily detected by ELISA. Indeed, we observed elevated levels of non-soluble, cell surface VEGF on PNEC from CRSwNP subjects (see FIG. 2). Further studies are needed to address the precise roles of the various isoforms of VEGF in this disease. Regardless, VEGF represents an important growth factor-related biomarker for sinonasal polyposis identified by our studies.

The data obtained from blocking antibodies indicates that VEGF is the growth factor responsible for this hyperplastic behavior. When the cells were treated with either anti-VEGF or anti-NP1 antibodies, the growth rate was normalized. This occurred the absence of exposure to exogenous VEGF. These data indicate that elevation in VEGF is more than merely a biomarker for this disease, but may also be pivotal in driving and maintaining a key pathological feature of the disease, epithelial hyperplasia. To our knowledge, this is the first report of VEGF functioning in an autocrine manner to control non-neoplastic human epithelial cell growth. This observation was unexpected.

We found expression of the receptor VEGFR2 in sinonasal polyp tissue. Moreover we demonstrated expression of activated form of this receptor, phospho-VEGFR2, on nasal epithelial cells from diseased polyp tissue. These studies confirm previous findings of the expression of VEGF and VEGFR2 on upper airway epithelium. VEGFR2 is known to mediate proliferative effects in the endothelial cell. Its presence in a phosphorylated and presumably activated form within epithelium of hyperplastic sinonasal polyp tissues in situ suggests that VEGF mediates biologically significant function in sinonasal epithelial cells.

Without wishing to be bound by any particular mechanism, it is suggested that the NP1 cell surface receptor acts in the present context via one or more of the following functions that have been previously reported: NP1 functions as a potent endothelial cell mitogen and regulates vasculature formation. NP1 is thought to function to increase the binding affinity of VEGF to VEGFR2, by serving as a docking site for ligand binding. NP1 occurs in a wide variety of tissues, including epithelial cells and tumors. Our finding that blocking antibodies targeted against NP1 virtually mimicked the inhibitory effect of blocking VEGF ligand itself supports our conclusion that activation of NP1 is essential for the VEGF-mediated increase in epithelial cell proliferation seen in CRSwNP subjects.

Again without wishing to be bound by any particular mechanism, it is suggested that the increase in cell growth observed with CRSwNP epithelium may be explained by a decrease in cell death due to the presence of a survival factor such as autocrine VEGF. Since both VEGF and NP1 activation have been shown to have anti-apoptotic function, we sought to determine whether VEGF contributes to cell survival by inhibiting apoptosis. The results in FIG. 6 suggest that VEGF functions to inhibit apoptosis through activation of NP1. Several studies have demonstrated that NP1 mediates VEGF-induced human breast cancer cell survival in the absence of VEGFR1 and VEGFR2. Barr et al has shown that in a breast cancer cell line that expresses constitutive VEGF and NP1 but lack VEGF receptor expression, NP1 blockade using a peptide antagonist induces tumor cell apoptosis (Barr et al. (2005) *Br J Cancer* 92, 328-333). Thus VEGF has a potential to act as a pro-survival factor on cells expressing NP1 in the absence of VEGFR1 and VEGFR2, a concept at least consistent with findings presented here.

In addition to implicating VEGF as an epithelial cell mitogen, we asked whether VEGF could function in an autocrine feedback manner to autoregulate its own expression in PNEC. Blockade of NP1 by antibody neutralization resulted in inhibition of VEGF production. These results were corroborated by effective siRNA silencing of NP1 in PNEC, which resulted in inhibition of VEGF production. In addition to the novel role of VEGF as an autocrine epithelial cell mitogen, to our knowledge, this is the first report of VEGF functioning in an autocrine manner to regulate its own expression in non-neoplastic, non-transformed primary human airway epithelial cells.

In summary, we have shown that VEGF can serve as a biomarker for sinonasal polyposis and have demonstrated a novel role for VEGF as an epithelial cell mitogen and prosurvival factor that functions in a positive feed forward manner. In addition, we have identified that this function is dependent on NP1, which we report as being constitutively expressed in human upper airway epithelial cells. Given the central role of the epithelium in orchestrating innate and adaptive immune responses of the airways, it is expected that treatment with inhibitors of VEGF, as demonstrated here with respect to CRSwNP, will also be applicable to the treatment of diseases such as asthma, as well.

III. Further Confirmation that Inhibition of the Expression or Activity of VEGF-A or a VEGF-A Receptor can Inhibit Epithelial Cell Mitogenesis in Airway Cells, and/or that it can be Used to Treat Subjects with Chronic Inflammatory Respiratory Disorders.

Inhibitory agents that are specific for one or more of the genes listed in Table 2, or proteins encoded by them, will be tested to confirm the expected result that inhibition of their expression and/or their activity inhibits the proliferation of epithelial cells, e.g., airway epithelial cells.

A. Rates of apoptosis from PNEC derived from patients will be exposed to inhibitors, and quantitated and compared using flow cytometric determination of annexin V fluoroscein isothionate (FITC) staining of PNEC grown under standardized conditions in vitro.

B. Measurement of autocrine VEGF production will be performed by ELISA assay for VEGF.

C. In the polyp tissue assay, we are able to grow and preserve intact human diseased polyp tissue in culture ex vivo. We will expose the polyp tissue cultures to the inhibitors and assay for cell growth and cell survival, using quantitative immunohistochemical PCNA staining and TUNEL staining, respectively.

The methods used to carry out these assays are conventional and well-known in the art.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including US provisional applications U.S. provisional applications 61/111,767, filed Nov. 6, 2008, 61/143,488, filed Jan. 9, 2009, and 61/242,158, filed Sep. 14, 2009 and in the figures are hereby incorporated in their entirety by reference.

We claim:

1. A method for treating a human subject having chronic rhinosinusitis by inhibiting the proliferation of an epithelial cell, comprising contacting the cell with:
    an effective amount of an antibody or an antigen binding fragment thereof that binds to human neuropilin-1, and optionally
    an effective amount of an antibody or an antigen binding fragment thereof that binds to human vascular endothelial growth factor-A, and/or
    an effective amount of antibody or an antigen binding fragment thereof that binds to human VEGF receptor 1, and/or
    an effective amount of an antibody or an antigen binding fragment thereof that binds to human VEGF receptor 2.

2. The method of claim 1, wherein the epithelial cell is in said subject, and the effective amount of the antibody or an antigen binding fragment thereof is administered to said subject.

3. The method of claim 1, wherein the chronic rhinosinusitis is chronic rhinosinusitis with nasal polyposis.

4. The method of claim 1, wherein the antibody or an antigen binding fragment thereof that binds to human neuropilin-1, and antibody or an antigen binding fragment thereof that binds to human vascular endothelial growth factor-A and/or human VEGF receptor 1, and/or human VEGF receptor 2 are administered by a systemic intravenous (IV) route.

5. The method of claim 1, wherein the antibody or an antigen binding fragment thereof that binds to human neuropilin-1, and antibody or an antigen binding fragment thereof that binds to human vascular endothelial growth factor-A and/or human VEGF receptor 1, and/or human VEGF receptor 2 are administered by an intranasal route.

6. The method of claim 1, wherein the antibody or an antigen binding fragment thereof that binds to human VEGF-A is selected from the group consisting of ranibizumab and bevacizumab.

7. A method for treating a human subject having chronic rhinosinusitis with nasal polyposis comprising administering to the subject an effective amount of an antibody or an antigen binding fragment thereof that binds to human neuropilin-1.

* * * * *